(12) United States Patent
Godart et al.

(10) Patent No.: US 9,352,030 B2
(45) Date of Patent: *May 31, 2016

(54) *MYCOBACTERIUM* ANTIGENIC COMPOSITION

(75) Inventors: Stéphane André Georges Godart, Rixensart (BE); Amina Laanan, Rixensart (BE); Dominique Ingrid Lemoine, Rixensart (BE)

(73) Assignee: GlaxoSmithKline Biologicals, S.A., Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/993,736

(22) PCT Filed: Dec. 14, 2011

(86) PCT No.: PCT/EP2011/072817
§ 371 (c)(1), (2), (4) Date: Jun. 13, 2013

(87) PCT Pub. No.: WO2012/080370
PCT Pub. Date: Jun. 21, 2012

(65) Prior Publication Data
US 2013/0287809 A1  Oct. 31, 2013

Related U.S. Application Data

(60) Provisional application No. 61/422,723, filed on Dec. 14, 2010.

(51) Int. Cl.
*A61K 39/04* (2006.01)

(52) U.S. Cl.
CPC .................................. *A61K 39/04* (2013.01)

(58) Field of Classification Search
None
See application file for complete search history.

(56) References Cited

U.S. PATENT DOCUMENTS

| | | | |
|---|---|---|---|
| 6,869,607 B1 | 3/2005 | Buschle et al. | |
| 7,927,818 B2* | 4/2011 | Felgner et al. | 435/7.1 |
| 8,067,016 B2* | 11/2011 | Skeiky et al. | 424/248.1 |
| 8,071,747 B2* | 12/2011 | Skeiky et al. | 536/23.7 |
| 8,110,200 B2* | 2/2012 | Skeiky et al. | 424/248.1 |
| 8,110,201 B2* | 2/2012 | Skeiky et al. | 424/248.1 |
| 8,470,338 B2 | 6/2013 | Coler et al. | |
| 8,557,247 B2* | 10/2013 | Lemoine | 424/184.1 |
| 9,056,913 B2 | 6/2015 | Coler et al. | |
| 2003/0014240 A1 | 1/2003 | Navoni et al. | |
| 2009/0035360 A1 | 2/2009 | Lemoine | |
| 2009/0285847 A1* | 11/2009 | Felgner et al. | 424/190.1 |
| 2009/0291062 A1 | 11/2009 | Fraunhofer et al. | |
| 2012/0087976 A1 | 4/2012 | Henderickx et al. | |
| 2012/0093921 A1 | 4/2012 | Henderickx et al. | |
| 2013/0280289 A1* | 10/2013 | Godart et al. | 424/190.1 |
| 2013/0287809 A1* | 10/2013 | Godart et al. | 424/190.1 |
| 2015/0231224 A1 | 8/2015 | Coler et al. | |

FOREIGN PATENT DOCUMENTS

| | | |
|---|---|---|
| WO | 9709428 A2 | 3/1997 |
| WO | 9709429 A2 | 3/1997 |
| WO | 9951748 A2 | 10/1999 |
| WO | 0124820 | 4/2001 |
| WO | 0198460 A2 | 12/2001 |
| WO | 03070187 A2 | 8/2003 |
| WO | 2006117240 A2 | 11/2006 |
| WO | WO 2009/088255 | 7/2009 |
| WO | WO 2010/142685 | 12/2010 |
| WO | WO 2010/142686 | 12/2010 |
| WO | 2012004820 | 1/2012 |

OTHER PUBLICATIONS

Wang et al, Microbiol. Immunol., 2008, 52:224-230.*
Mustfa et al, Infection and Immunity, Aug. 2006, 74/8:4566-4572.*
Leroux-Roels et al, Clinical and Vaccine Immunology, Nov. 2010, 17/11:1763-1771.*
Hawridge et al, Paediatric Respiratory Reviews, 2011, 12:46-51.*
Grange et al, Tuberculosis, 2011, 91:179-185.*
Dillon et al, Infection and Immunity, Jun. 1999, 67/6:2941-2950.*
Skeiky et al, J. Immunology, 2004, 172:7618-7628.*
Reed et al, PNAS, Feb. 17, 2009, 106/7:2301-2306.*
Leroux-Roels, et al., "Evaluation of the safety and immunogenicity of two antigen concentrations of the Mtb72F/AS02(A) candidate tuberculosis vaccine in purified protein derivative-negative adults", Clinical and Vaccine Immunology, 17(11):1763-1771, American Society for Microbiology, 2010.
Al-Attiyah R et al; In Vitro Cellular Immune Responses to Comple and Newly Defined Recombinant Antigens of *Mycobacterium tuberculosis*; Clinical & Amp; Experimental Immunology, Aug. 2004; vol. 138 No. 1, pp. 139-144.
Brandt et al; The Protective Effect of the *Mycobacterium bovis* BCG Vaccine in Increased by coadministration with the *Mycobacterium tuberculosis* 72-Kilodalton Fusion polyprotein MTB72F in M. tuberculosis infected guniea pigs; Infection and Immunity, Nov. 4; vol. 72, No. 11, pp. 6622-6632.
Dillon D et al; Molecular Characterization and Human T-Cell Responses to a Member of a Novel *Mycobacterium tuberculosis* MTB39Gene Family; Infection and Immunity; Jun. 1999, vol. 67 No. 6; pp. 2941-2950.
Reed S et al; Defined Tuberculosis Vaccine, MTB72F/ASO2A, Evidence of Protection in Cynomulgus Monkeys Proceedings of the National academy of Sciences; 2009; vol. 106 No. 7; pp. 2301-2306.
Reed S et al; Tuberculosis Vaccine Development From Mouse to Man; Microbes and Infection; May 2005; vol. 7 No. 5-6, pp. 922-931.

(Continued)

*Primary Examiner* — Nita M Minnifield

(74) *Attorney, Agent, or Firm* — Eric J. Kron

(57) ABSTRACT

Immunogenic compositions comprising an Rv1196 related antigen, wherein the conductivity of the composition is 13 mS/cm or lower, or the concentration of salts of the composition is 130 mM or lower, and their use in medicine, are provided.

16 Claims, 18 Drawing Sheets

(56) References Cited

OTHER PUBLICATIONS

Skeiky Y et al ; Cloning, Expression and Immunological Evaluation of two Putative Secreted Serine Protease Antigens of *Mycobacterium tuberculosis*; Infection and Immunity; 1999 ; vol. 67, No. 8; pp. 3998-4007.

Skeiky Y et al; Differental Immune Responses and Protective Efficacy Induced by Components of a Tuberculosis Polyprotein Vaccine, MTB72F, Delivered as naked DNA or Recombinant Protein; Journal of Immunology; 2004; vol. 172 No. 12; pp. 7618-7628.

Vekemans J et al ; Immune Responses to *Mycobacterial* Antigens in Gambian Population; Implications of Vaccines and Immunodiagnostic test design; Infection and Immunity; Jan. 2004; vol. 72, No. 1; pp. 381-388.

Von Eschen K et al ; The Candidate Tuberculosis Vaccine MTB72F/ASO2A; Tolerability and Immunogencity in Humans; Human Vaccines; 2009 ; vol. 5 No. 7; pp. 475-482.

Nair S et al; "The PPE18 of *Mycobacterium tuberculosis* Interacts with TLR2 and Activates IL-10 Induction in Macrophage"; Journal of Immunology, 2009; vol. 183 No. 10, pp. 6269-6281.

Aulton, Michael et al; Pharmaceutics: The Science of Dosage form design, 2da. Ed. Elsevier Ltd., Philadel[hia 2002, pp. 25 and 77.

Day et al., "Induction and Regulation of T-Cell Immunity by the Novel Tuberculosis Vaccine M72/AS01 in South African Adults", Am J Respir Crit Care Med, vol. 188, No. 4, pp. 492-502.

Garcon et al, "GlaxoSmithKline Adjuvant Systems in Vaccines: Concepts, Achievements and Perspectives", Expert Reviews in Vaccines, vol. 6, No. 5, pp. 723-739.

Leroux-Roels et al., Improved CD4+ T Cell Responses to *Mycobacterium tuberculosis* in PPD-Negative Adults by M72/AS01 as compared to the M72/AS02 and Mtb72F/AS02 tuberculosis candidate vaccine formulation: A randomized trial, Vaccine, 2013, vol. 31, No. 17, pp. 2196-2206.

Montoya et al., "A Randomized, Controlled Dose-Finding Phase II Study of the M72/AS01 Candidate Tuperculosis Vaccine in Healthy PPD-Positive Adults", Journal of Clinical Immunology, 2013, Initial Publication DOI 10.10071 Ds10875-013-9949-3).

Montoya, J., et al., "Tropical Medicine and International Health", vol. 14, Suppl. 2, p. 42, Abstract T3P2-07, Sep. 2009.

\* cited by examiner

MYCOBACTERIUM ANTIGENIC COMPOSITION

This application is the US National Stage of International Application No. PCT/EP2011/072817, filed 14 Dec. 2011, which claims benefit of the filing date of U.S. Provisional Application No. 61/422,723, filed 14 Dec. 2010, which is incorporated herein by reference in its entirety.

FIELD OF THE INVENTION

The present invention relates to immunogenic compositions comprising an Rv1196 related antigen and having a low ionic strength. The present invention also relates to such immunogenic compositions which further comprise one or more immunostimulants. Methods for the preparation of such immunogenic compositions and related kits are also provided.

BACKGROUND OF THE INVENTION

Tuberculosis (TB) is a chronic infectious disease caused by infection with *Mycobacterium tuberculosis* and other *Mycobacterium* species. It is a major disease in developing countries, as well as an increasing problem in developed areas of the world. More than 2 billion people are believed to be infected with TB bacilli, with about 9.4 million new cases of TB and 1.7 million deaths each year. 10% of those infected with TB bacilli will develop active TB, each person with active TB infecting an average of 10 to 15 others per year. While annual incidence rates have peaked globally, the number of deaths and cases is still rising due to population growth (World Health Organisation *Tuberculosis Facts* 2010).

The mycobacterial protein Rv1196 (described, for example, by the name Mtb39a in Dillon et al *Infection and Immunity* 1999 67(6): 2941-2950) or fragments or derivatives thereof are protein antigens of potential benefit for the treatment or prevention of tuberculosis. Rv1196 is highly conserved, with 100% sequence identity across H37Rv, C, Haarlem, CDC1551, 94-M4241A, 98-R6041NH-RIF-EM, KZN605, KZN1435, KZN4207, KZNR506 strains, the F11 strain having a single point mutation Q30K. Rv1196 is a component of the fusion protein antigens Mtb72f and M72 (described, for example, in international patent application WO2006/117240).

The formulation of protein antigens is extremely important in order to ensure immunogenicity is maintained. Immunostimulants are sometimes used to improve the immune response raised to any given antigen. However, the inclusion of adjuvants into an immunogenic composition increases the complexity of preparation of the components as well as the complexity of distribution and formulation of the composition. The preparation of each of the adjuvant components as well as the antigenic component must be considered by formulators. In particular, the compatibility of the antigenic component with the adjuvant component should be considered. This is particularly the case where lyophilised antigens or antigenic preparations are intended to be reconstituted with an adjuvant preparation. In such a circumstance, it is important that the buffer of the adjuvant preparation is suitable for the antigen and that immunogenicity or solubility of the antigen is not affected by the adjuvant.

SUMMARY OF THE INVENTION

The present inventors have identified for the first time that Rv1196 related antigens are particularly sensitive to the presence of salts. Without being limited by theory, it is believed Rv1196 related antigens are detrimentally impacted by a phenomenon known as "salting out" which may be defined as the precipitation of a protein from its solution by interaction with salts, such as sodium chloride. The present inventors have found that these antigens aggregate and precipitate at a concentration of sodium chloride as low as 150 mM. Consequently, the stability of immunogenic compositions comprising Rv1196 related antigens can surprisingly be improved by a reduction in the concentration of sodium chloride.

Accordingly, the present invention provides an immunogenic composition comprising an Rv1196 related antigen, wherein the conductivity of the composition is 13 mS/cm or lower.

Additionally provided is an immunogenic composition comprising an Rv1196 related antigen, wherein the concentration of salts in said composition is 130 mM or lower.

The present invention also provides an immunogenic composition comprising an Rv1196 related antigen, wherein the concentration of sodium chloride in said composition is 130 mM or lower.

BRIEF DESCRIPTION OF SEQUENCE IDENTIFIERS

Figure 1:
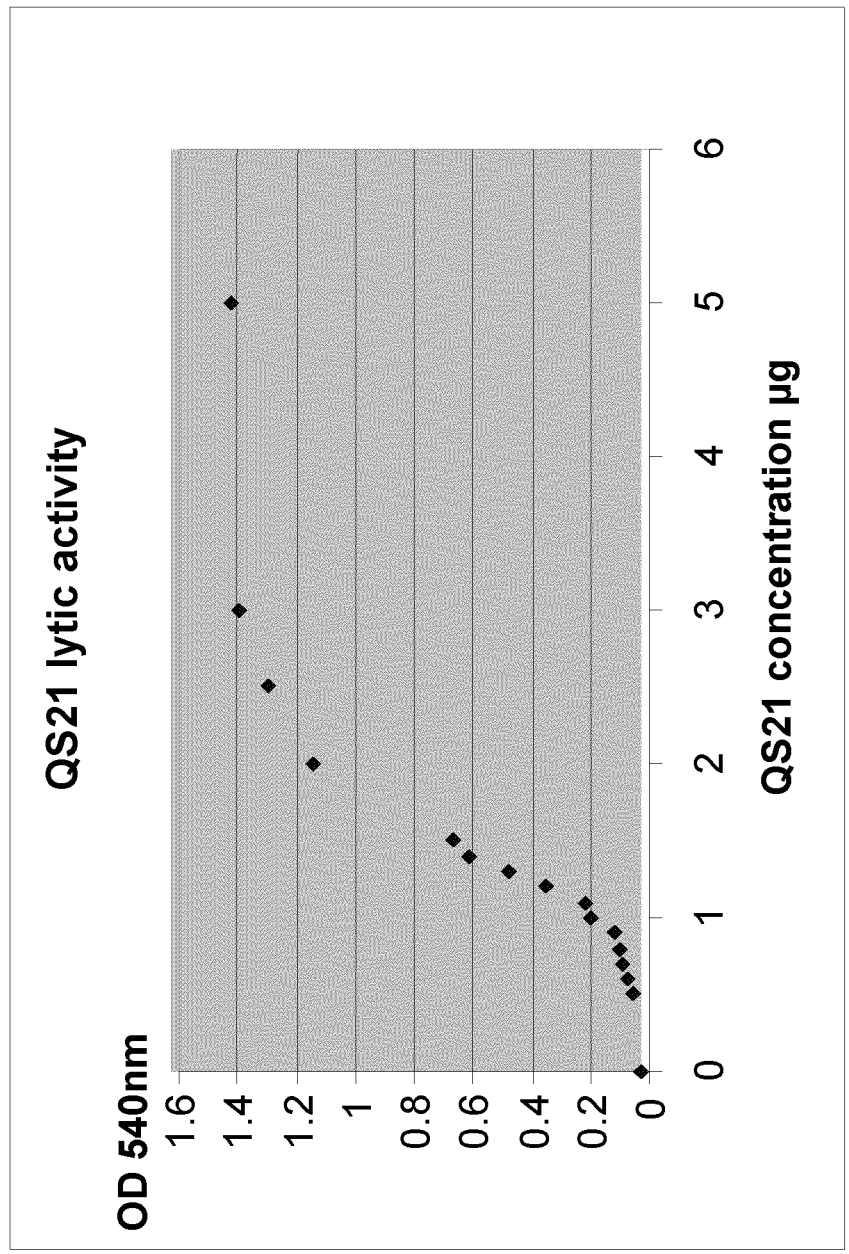
FIG. 1. QS21 lytic activity curve

SEQ ID No: 1 Amino acid sequence for the Rv1196 protein from *Mycobacterium tuberculosis* H37Rv SEQ ID No: 2 Nucleotide sequence encoding the Rv1196 protein from *Mycobacterium tuberculosis* H37Rv SEQ ID No: 3 Amino acid sequence for the Rv1196 protein from *Mycobacterium tuberculosis* F11

SEQ ID No: 4 Nucleotide sequence encoding the Rv1196 protein from *Mycobacterium tuberculosis* F11

SEQ ID No: 5 Amino acid sequence for the M72 protein

SEQ ID No: 6 Nucleotide sequence encoding the M72 protein
SEQ ID No: 7 Amino acid sequence for the M72 protein with two N-terminal His residues
SEQ ID No: 8 Nucleotide sequence encoding the M72 protein with two N-terminal His residues
SEQ ID No: 9 Amino acid sequence for the Mtb72f protein
SEQ ID No: 10 Nucleotide sequence encoding the Mtb72f protein
SEQ ID No: 11 Amino acid sequence for the Mtb72f protein with six N-terminal His residues
SEQ ID No: 12 Nucleotide sequence encoding the Mtb72f protein with six N-terminal His residues
SEQ ID No: 13 Nucleotide sequence for CpG Oligo 1 (CpG 1826)
SEQ ID No: 14 Nucleotide sequence for CpG Oligo 2 (CpG 1758)
SEQ ID No: 15 Nucleotide sequence for CpG Oligo 3
SEQ ID No: 16 Nucleotide sequence for CpG Oligo 4 (CpG 2006)
SEQ ID No: 17 Nucleotide sequence for CpG Oligo 5 (CpG 1686)

DETAILED DESCRIPTION OF THE INVENTION

In a first aspect, the present invention provides an immunogenic composition comprising an Rv1196 related antigen, wherein the conductivity of the composition is 13 mS/cm or lower. In particular, the present invention provides immunogenic compositions comprising an Rv1196 related antigen, wherein the conductivity of the immunogenic composition is 12 mS/cm or lower, for example 10 mS/cm or lower, 8 mS/cm or lower, 6 mS/cm or lower, 5 mS/cm or lower, 4 mS/cm or lower, or 3 mS/cm or lower. In a particular embodiment the conductivity of the immunogenic composition is 2.5 mS/cm or lower, such as 2.25 mS/cm or lower, or 2.0 mS/cm or lower. In a further specific embodiment the conductivity of the immunogenic composition is 1.5 to 2.5 mS/cm.

In a second aspect, the present invention provides an immunogenic composition comprising an Rv1196 related antigen, wherein the concentration of salts in said composition is 130 mM or lower. In particular, the present invention provides immunogenic compositions comprising an Rv1196 related antigen, wherein the concentration of salts in said composition is 100 mM or lower, for example 90 mM or lower, 80 mM or lower, 70 mM or lower, 60 mM or lower, 50 mM or lower, or 40 mM or lower. In a particular embodiment the concentration of salts in said composition is 35 mM or lower, such as 30 mM or lower, or 25 mM or lower. In a further specific embodiment the concentration of salts in said composition is 20 to 40 mM, such as 25 to 35 mM.

In a third aspect, the present invention provides an immunogenic composition comprising an Rv1196 related antigen, wherein the concentration of sodium chloride is 130 mM or lower. In particular, the present invention provides immunogenic compositions comprising an Rv1196 related antigen, wherein the concentration of sodium chloride is 100 mM or lower, for example 90 mM or lower, 80 mM or lower, 70 mM or lower, 60 mM or lower, 50 mM or lower, 40 mM or lower, 30 mM or lower, 20 mM or lower or 15 mM or lower. In a particular embodiment the concentration of sodium chloride in the immunogenic composition is 10 mM or lower, such as 7.5 mM or lower. Suitably the concentration of sodium chloride in the immunogenic composition or is at or below 5 mM. In a further specific embodiment, the immunogenic composition is essentially free of sodium chloride. By essentially free is meant that the concentration of sodium chloride is at or very near to zero mM (such as 3 mM or less, 2 mM or less or 1 mM or less).

Suitably, the concentration of $CaCl_2$ in the immunogenic compositions will be 40 mM or lower, 30 mM or lower, 20 mM or lower, 15 mM or lower or 10 mM or lower.

Suitably, the concentration of $MgSO_4$ in the immunogenic compositions will be 80 mM or lower, 60 mM or lower, 40 mM or lower, 30 mM or lower, 20 mM or lower or 10 mM or lower.

Suitably, the total concentration of $NH_4^+$, $Mg^{2+}$ and $Ca^{2+}$ ions in the immunogenic compositions will be 80 mM or lower, 60 mM or lower, 40 mM or lower, 30 mM or lower, 20 mM or lower or 10 mM or lower.

The immunogenic compositions of the invention will be aqueous preparations.

The conductivity of an immunogenic composition of the invention can be measured using techniques known in the art, for example using a dedicated conductivity meter or other instrument with the capability to measure conductivity. One suitable instrument is the Zetasizer Nano ZS from Malvern Instruments (UK).

The skilled person can readily test for the concentration of both sodium ($Na^+$) and chloride ($Cl^-$) ions using known techniques and kits. For example, sodium can be determined using a kit such as the Sodium Enzymatic Assay Kit (Catalogue Number: BQ011EAEL) from Biosupply. Chloride can be determined using a kit such as Chloride Enzymatic Assay Kit (Catalogue Number: BQ006EAEL) from Biosupply.

Tuberculosis (TB) is a chronic infectious disease caused by infection with *Mycobacterium tuberculosis* and other *Mycobacterium* species. It is a major disease in developing countries, as well as an increasing problem in developed areas of the world. More than 2 billion people are believed to be infected with TB bacilli, with about 9.4 million new cases of TB and 1.7 million deaths each year. 10% of those infected with TB bacilli will develop active TB, each person with active TB infecting an average of 10 to 15 others per year. While annual incidence rates have peaked globally, the number of deaths and cases is still rising due to population growth (World Health Organisation Tuberculosis Facts 2010).

*Mycobacterium tuberculosis* infects individuals through the respiratory route. Alveolar macrophages engulf the bacterium, but it is able to survive and proliferate by inhibiting phagosome fusion with acidic lysosomes. A complex immune response involving CD4+ and CD8+ T cells ensues, ultimately resulting in the formation of a granuloma. Central to the success of *Mycobacterium tuberculosis* as a pathogen is the fact that the isolated, but not eradicated, bacterium may persist for long periods, leaving an individual vulnerable to the later development of active TB.

Fewer than 5% of infected individuals develop active TB in the first years after infection. The granuloma can persist for decades and is believed to contain live *Mycobacterium tuberculosis* in a state of dormancy, deprived of oxygen and nutrients. However, recently it has been suggested that the majority of the bacteria in the dormancy state are located in non-macrophage cell types spread throughout the body (Locht et al, *Expert Opin. Biol. Ther.* 2007 7(11):1665-1677). The development of active TB occurs when the balance between the host's natural immunity and the pathogen changes, for example as a result of an immunosuppressive event (Anderson P *Trends in Microbiology* 2007 15(1):7-13; Ehlers S *Infection* 2009 37(2):87-95).

A dynamic hypothesis describing the balance between latent TB and active TB has also been proposed (Cardana P-J

*Inflammation & Allergy—Drug Targets* 2006 6:27-39; Cardana P-J *Infection* 2009 37(2):80-86).

Although an infection may be asymptomatic for a considerable period of time, the active disease is most commonly manifested as an acute inflammation of the lungs, resulting in tiredness, weight loss, fever and a persistent cough. If untreated, serious complications and death typically result.

Tuberculosis can generally be controlled using extended antibiotic therapy, although such treatment is not sufficient to prevent the spread of the disease. Actively infected individuals may be largely asymptomatic, but contagious, for some time. In addition, although compliance with the treatment regimen is critical, patient behaviour is difficult to monitor. Some patients do not complete the course of treatment, which can lead to ineffective treatment and the development of drug resistance.

Multidrug-resistant TB (MDR-TB) is a form which fails to respond to first line medications. 3.3% of all TB cases are MDR-TB, with an estimated 440,000 new MDR-TB cases occurring each year. Extensively drug-resistant TB (XDR-TB) occurs when resistance to second line medications develops on top of resistance to first line medications. The virtually untreatable XDR-TB has been confirmed in 58 countries (World Health Organisation *Tuberculosis Facts* 2010).

Even if a full course of antibiotic treatment is completed, infection with *M. tuberculosis* may not be eradicated from the infected individual and may remain as a latent infection that can be reactivated. In order to control the spread of tuberculosis, an effective vaccination programme and accurate early diagnosis of the disease are of utmost importance.

Currently, vaccination with live bacteria is the most widely used method for inducing protective immunity. The most common *Mycobacterium* employed for this purpose is *Bacillus* Calmette-Guerin (BCG), an avirulent strain of *M. bovis* which was first developed over 60 years ago. However, the safety and efficacy of BCG is a source of controversy—while protecting against severe disease manifestation in children, BCG does not prevent the establishment of latent TB or the reactivation of pulmonary disease in adult life. Additionally, some countries, such as the United States, do not vaccinate the general public with this agent.

Several of the proteins which are strongly expressed during the early stages of *Mycobacterium* infection have been shown to provide protective efficacy in animal vaccination models. However, vaccination with antigens which are highly expressed during the early stages of infection may not provide an optimal immune response for dealing with later stages of infection. Adequate control during latent infection may require T cells which are specific for the particular antigens which are expressed at that time. Post-exposure vaccines which directly target the dormant persistent bacteria may aid in protecting against TB reactivation, thereby enhancing TB control, or even enabling clearance of the infection. A vaccine targeting latent TB could therefore significantly and economically reduce global TB infection rates.

Subunit vaccines based on late stage antigens could also be utilised in combination with early stage antigens to provide a multiphase vaccine. Alternatively, early and/or late stage antigens could be used to complement and improve BCG vaccination (either by boosting the BCG response or through the development of advanced recombinant BCG strains).

The protein antigen Rv1196 is of potential benefit for the treatment or prevention of tuberculosis. Rv1196 is described, for example, by the name Mtb39a in Dillon et al *Infection and Immunity* 1999 67(6): 2941-2950). The Rv1196 protein is highly conserved, with 100% sequence identity across H37Rv, C, Haarlem, CDC1551, KZN605, KZN1435 and KZN4207 strains, the F11 strain having a single point mutation (Q30K).

The protein antigens Mtb72f and M72 are fusion proteins comprising Rv1196 and are of potential benefit for the treatment or prevention of tuberculosis. Mtb72f has been shown to provide protection in a number of animal models (see, for example: Brandt et al *Infect. Immun.* 2004 72(11):6622-6632; Skeiky et al *J. Immunol.* 2004 172:7618-7628; Tsenova et al *Infect. Immun.* 2006 74(4):2392-2401; Reed et al PNAS 2009 106(7):2301-2306). Mtb72f has also been the subject of clinical investigations (Von Eschen et al 2009 *Human Vaccines* 5(7):475-482). M72 is an improved antigen which incorporates a single serine to alanine mutation relative to Mtb72f, resulting in improved stability characteristics. M72 related antigens have also been shown to be of value in a latent TB model (international patent application WO2006/117240).

As used herein the term 'Rv1196 related antigen' refers to the Rv1196 protein provided in SEQ ID No: 1 or an immunogenic derivative thereof. As used herein the term "derivative" refers to an antigen that is modified relative to the reference sequence. Immunogenic derivatives are sufficiently similar to the reference sequence to retain the immunogenic properties of the reference sequence and remain capable of allowing an immune response to be raised against the reference sequence. A derivative may, for example, comprise a modified version of the reference sequence or alternatively may consist of a modified version of the reference sequence.

The Rv1196 related antigen may for example contain fewer than 1000 amino acid residues, such as fewer than 900 amino acid residues, in particular fewer than 800 amino acid residues.

T cell epitopes are short contiguous stretches of amino acids which are recognised by T cells (e.g. CD4+ or CD8+ T cells). Identification of T cell epitopes may be achieved through epitope mapping experiments which are known to the person skilled in the art (see, for example, Paul, *Fundamental Immunology*, 3rd ed., 243-247 (1993); Beiβbarth et al *Bioinformatics* 2005 21 (Suppl. 1):i29-i37). In a diverse out-bred population, such as humans, different HLA types mean that particular epitopes may not be recognised by all members of the population. As a result of the crucial involvement of the T cell response in tuberculosis, to maximise the level of recognition and scale of immune response, an immunogenic derivative of Rv1196 is desirably one which contains the majority (or suitably all) T cell epitopes intact.

The skilled person will recognise that individual substitutions, deletions or additions to the Rv1196 protein which alters, adds or deletes a single amino acid or a small percentage of amino acids is an "immunogenic derivative" where the alteration(s) results in the substitution of an amino acid with a functionally similar amino acid or the substitution/deletion/addition of residues which do not substantially impact the immunogenic function.

Conservative substitution tables providing functionally similar amino acids are well known in the art. In general, such conservative substitutions will fall within one of the amino-acid groupings specified below, though in some circumstances other substitutions may be possible without substantially affecting the immunogenic properties of the antigen. The following eight groups each contain amino acids that are typically conservative substitutions for one another:
 1) Alanine (A), Glycine (G);
 2) Aspartic acid (D), Glutamic acid (E);
 3) Asparagine (N), Glutamine (Q);
 4) Arginine (R), Lysine (K);
 5) Isoleucine (I), Leucine (L), Methionine (M), Valine (V);

6) Phenylalanine (F), Tyrosine (Y), Tryptophan (W);
7) Serine (S), Threonine (T); and
8) Cysteine (C), Methionine (M)
(see, e.g., Creighton, Proteins 1984).

Suitably such substitutions do not occur in the region of an epitope, and do not therefore have a significant impact on the immunogenic properties of the antigen.

Immunogenic derivatives may also include those wherein additional amino acids are inserted compared to the reference sequence. Suitably such insertions do not occur in the region of an epitope, and do not therefore have a significant impact on the immunogenic properties of the antigen. One example of insertions includes a short stretch of histidine residues (e.g. 2-6 residues) to aid expression and/or purification of the antigen in question.

Immunogenic derivatives include those wherein amino acids have been deleted compared to the reference sequence. Suitably such deletions do not occur in the region of an epitope, and do not therefore have a significant impact on the immunogenic properties of the antigen.

The skilled person will recognise that a particular immunogenic derivative may comprise substitutions, deletions and additions (or any combination thereof).

The terms "identical" or percentage "identity," in the context of two or more polypeptide sequences, refer to two or more sequences or sub-sequences that are the same or have a specified percentage of amino acid residues that are the same (i.e., 70% identity, optionally 75%, 80%, 85%, 90%, 95%, 98% or 99% identity over a specified region), when compared and aligned for maximum correspondence over a comparison window, or designated region as measured using one of the following sequence comparison algorithms or by manual alignment and visual inspection. This definition also refers to the compliment of a test sequence. Optionally, the identity exists over a region that is at least 250 amino acids in length, such as 300 amino acids or 350 amino acids. Suitably, the comparison is performed over a window corresponding to the entire length of the reference sequence (as opposed to the derivative sequence).

For sequence comparison, one sequence acts as the reference sequence, to which the test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percentage sequence identities for the test sequences relative to the reference sequence, based on the program parameters.

A "comparison window", as used herein, refers to a segment in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerised implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984)).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (website at www.ncbi.nlm.nih.gov/). This algorithm involves first identifying high scoring sequence pairs (HSPS) by identifying short words of length W in the query sequence, which either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find longer HSPS containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (N) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

In any event, immunogenic derivatives of a polypeptide sequence will have essentially the same activity as the reference sequence. By essentially the same activity is meant at least 50%, suitably at least 75% and especially at least 90% activity of the reference sequence in an in vitro restimulation assay of PBMC or whole blood with specific antigens (e.g. restimulation for a period of between several hours to up to two weeks, such as up to one day, 1 day to 1 week or 1 to 2 weeks) that measures the activation of the cells via lymphoproliferation, production of cytokines in the supernatant of culture (measured by ELISA, CBA etc) or characterisation of T and B cell responses by intra and extracellular staining (e.g. using antibodies specific to immune markers, such as CD3, CD4, CD8, IL2, TNF-alpha, IFN-gamma, CD40L, CD69 etc) followed by analysis with a flowcytometer. Suitably, by essentially the same activity is meant at least 50%, suitably at least 75% and especially at least 90% activity of the reference sequence in a T cell proliferation and/or IFN-gamma production assay.

Suitably the Rv1196 related antigen will comprise, such as consist of, a sequence having at least 70% identity to SEQ ID No: 1, such as at least 80%, in particular at least 90%, especially at least 95%, for example at least 98%, such as at least 99%.

A specific example of an Rv1196 related antigen is Rv1196 from *Mycobacterium tuberculosis* strain H37Rv, as provided in SEQ ID No: 1. Consequently, in one embodiment of the invention the Rv1196 related antigen is a protein comprising SEQ ID No: 1. In a second embodiment of the invention the Rv1196 related antigen is a protein consisting of SEQ ID No: 1.

A further example of an Rv1196 related antigen is Rv1196 from *Mycobacterium tuberculosis* strain F11, as provided in SEQ ID No: 3. In one embodiment of the invention the Rv1196 related antigen is a protein comprising SEQ ID No: 3. In a second embodiment of the invention the Rv1196 related antigen is a protein consisting of SEQ ID No: 3.

Typical Rv1196 related antigens will comprise, such as consist of, an immunogenic derivative of SEQ ID No: 1 having a small number of deletions insertions and/or substitutions. Examples are those having deletions of up to 5 residues at 0-5 locations, insertions of up to 5 residues at 0-5 five locations and substitutions of up to 20 residues.

Other immunogenic derivatives of Rv1196 are those comprising, such as consisting of, a fragment of SEQ ID No: 1 which is at least 250 amino acids in length, such as at least 300 amino acids in length or at least 350 amino acids in length.

Additional immunogenic derivatives of Rv1196 are those comprising, such as consisting of, a fragment of SEQ ID No: 3 which is at least 250 amino acids in length, such as at least 300 amino acids in length, at least 350 amino acids in length or at least 380 amino acids in length.

Rv1196 related antigens may be prepared by methods previously described (e.g. Dillon et al *Infection and Immunity* 1999 67(6): 2941-2950; WO2006/117240), those provided in the Examples, or methods analogous thereto.

The immunogenic compositions may comprise one or more further antigenic components. Such additional antigenic components need not themselves be sensitive to the presence of salts in the composition.

Additional antigenic components may be intended to strengthen or complement the immune responses solicited by the Rv1196 related antigen in the field of tuberculosis prevention and therapy or additional antigens could be associated with other pathogens and are intended for administration with the Rv1196 related antigen for reasons of convenience. Where a number of antigenic components are present within the formulation, these may be provided in the form of individual polypeptides or fusion proteins. In some circumstances additional antigenic components may be provided as a polynucleotide (or polynucleotides).

Particular immunogenic derivatives of the Rv1196 protein include fusion proteins comprising a sequence having at least 70% identity to SEQ ID No: 1, such as at least 80%, in particular at least 90%, especially at least 95%, for example at least 98%, such as at least 99%.

Exemplary fusion proteins containing an Rv1196 protein include: M72 (SEQ ID No: 5) and variants thereof such as those with additional His residues at the N-terminus (e.g. two His residues, as provided in SEQ ID No: 7; or a polyhistidine tag of five or particularly six His residues, which may be used for nickel affinity purification); Mtb72f (SEQ ID No: 9) which contains the original serine residue that has been mutated in M72, as are Mtb72f proteins with additional His residues at the N-terminus (e.g. two H is residues; or a polyhistidine tag of five or particularly six His residues, which may be used for nickel affinity purification).

In certain embodiments the Rv1196 related antigen comprises, such as consists of, a sequence having at least at least 90% identity to SEQ ID No: 5, especially at least 95%, for example at least 98%, such as at least 99%. In other embodiments the Rv1196 related antigen comprises, such as consists of, a sequence having at least at least 90% identity to SEQ ID No: 7, especially at least 95%, for example at least 98%, such as at least 99%.

It is well known that for parenteral administration solutions should have a pharmaceutically acceptable osmolality to avoid cell distortion or lysis. A pharmaceutically acceptable osmolality will generally mean that solutions will have an osmolality which is approximately isotonic or mildly hypertonic. Suitably the immunogenic compositions of the present invention will have an osmolality in the range of 250 to 750 mOsm/kg, for example, the osmolality may be in the range of 250 to 550 mOsm/kg, such as in the range of 280 to 500 mOsm/kg.

Osmolality may be measured according to techniques known in the art, such as by the use of a commercially available osmometer, for example the Advanced® Model 2020 available from Advanced Instruments Inc. (USA).

An "isotonicity agent" is a compound that is physiologically tolerated and imparts a suitable tonicity to a formulation to prevent the net flow of water across cell membranes that are in contact with the formulation.

Generally, sodium chloride (NaCl) is used as a tonicity agent. The present inventors have shown for the first time that that Rv1196 related antigens are particularly sensitive to "salting out", a process whereby the proteins in solution aggregate or coagulate when in solutions containing high concentrations of salt. Consequently, alternative means are provided for ensuring the immunogenic compositions of the invention have a pharmaceutically acceptable osmolality.

In a particular embodiment there are provided immunogenic compositions further comprising a non-ionic tonicity agent. A non-ionic tonicity agent for use in an immunogenic composition will itself need to be pharmaceutically acceptable, e.g. suitable for use in humans, as well as being compatible with the Rv1196 related antigen and further compatible with other components such as the immunostimulant(s).

In one embodiment of the present invention, suitable non-ionic tonicity agents are polyols, sugars (in particular sucrose, fructose, dextrose or glucose) or amino acids such as glycine. In one embodiment the polyol is a sugar alcohol, especially a C3-6 sugar alcohol. Exemplary sugar alcohols include glycerol, erythritol, threitol, arabitol, xylitol, ribitol, sorbitol, mannitol, dulcitol and iditol. In a specific example of this embodiment, a suitable non-ionic tonicity agent is sorbitol. The skilled person will recognise that an appropriate osmolality may be attained through the use of a mixture of different tonicity agents. In a particular embodiment of the invention the non-ionic tonicity agent in the compositions of the invention incorporates sucrose and/or sorbitol.

In one embodiment, a suitable concentration of polyol within the immunogenic composition is between about 2.5 and about 15% (w/v), in particular between about 2.5 and about 10% (w/v) for example between about 3 and about 7% (w/v), such as between about 4 and about 6% (w/v). In a specific example of this embodiment, the polyol is sorbitol.

In another embodiment, the immunogenic composition comprises sucrose and sorbitol. In such circumstances the immunogenic composition may suitably contain between about 2.5 and about 15% (w/v) of sucrose and between about 2.5 and about 15% (w/v) of sorbitol, in particular between about 2.5 and about 10% (w/v) of sucrose and between about 2.5 and about 10% (w/v) of sorbitol, for example, between about 3 and about 7% (w/v) of sucrose and between about 3 and about 7% (w/v) of sorbitol, such as between about 4 and about 6% (w/v) of sucrose and between about 4 and about 6% (w/v) of sorbitol.

The pH of the immunogenic compositions should be suitable for parenteral administration. Typically the pH will be in the range of 6.0 to 9.0. Suitably the pH will be in the range 7.0 to 9.0, especially 7.25 to 8.75, such as 7.5 to 8.5, in particular pH 7.75 to 8.25. A pH of about 8.0 is of particular interest.

The pH may be controlled by the use of buffers, including for example Tris or phosphate buffers.

In a particular embodiment of the invention, the immunogenic composition comprises one or more immunostimulants.

In one embodiment, the immunostimulant may be a saponin. A particularly suitable saponin for use in the present invention is Quil A and its derivatives. Quil A is a saponin preparation isolated from the South American tree *Quillaja saponaria* Molina and was first described by Dalsgaard et al. in 1974 ("Saponin adjuvants", Archiv. für die gesamte Virusforschung, Vol. 44, Springer Verlag, Berlin, p 243-254) to have adjuvant activity. Purified fractions of Quil A have been isolated by HPLC which retain adjuvant activity without the toxicity associated with Quil A (WO88/09336), for example QS7 and QS21 (also known as QA7 and QA21). QS21 is a natural saponin derived from the bark of *Quillaja saponaria* Molina, which induces CD8+ cytotoxic T cells (CTLs), Th1 cells and a predominant IgG2a antibody response. QS21 is a preferred saponin in the context of the present invention.

In a suitable form of the present invention, the saponin adjuvant within the immunogenic composition is a derivative of *saponaria* Molina Quil A, in particular an immunologically active fraction of Quil A, such as QS17 or QS21, suitably QS21.

Desirably, QS21 is provided in a less reactogenic composition where it is quenched with an exogenous sterol, such as cholesterol for example. Several particular forms of less reactogenic compositions wherein QS21 is quenched with cholesterol exist. In a specific embodiment, the saponin/sterol is in the form of a liposome structure (such as described in WO96/33739, Example 1). In this embodiment the liposomes suitably contain a neutral lipid, for example phosphatidylcholine, which is suitably non-crystalline at room temperature, for example egg yolk phosphatidylcholine, dioleoyl phosphatidylcholine (DOPC) or dilauryl phosphatidylcholine. The liposomes may also contain a charged lipid which increases the stability of the lipsome-QS21 structure for liposomes composed of saturated lipids. In these cases the amount of charged lipid is suitably 1-20% w/w, such as 5-10%. The ratio of sterol to phospholipid is 1-50% (mol/mol), suitably 20-25%.

Suitable sterols include β-sitosterol, stigmasterol, ergosterol, ergocalciferol and cholesterol. In one particular embodiment, the immunogenic composition comprises cholesterol as sterol. These sterols are well known in the art, for example cholesterol is disclosed in the Merck Index, 11th Edn., page 341, as a naturally occurring sterol found in animal fat.

Where the active saponin fraction is QS21, the ratio of QS21:sterol will typically be in the order of 1:100 to 1:1 (w/w), suitably between 1:10 to 1:1 (w/w), and especially 1:5 to 1:1 (w/w). Suitably excess sterol is present, the ratio of QS21:sterol being at least 1:2 (w/w). In one embodiment, the ratio of QS21:sterol is 1:5 (w/w). The sterol is suitably cholesterol.

In another embodiment, the immunogenic composition comprises an immunostimulant which is a Toll-like receptor 4 (TLR4) agonist. By "TLR agonist" it is meant a component which is capable of causing a signaling response through a TLR signaling pathway, either as a direct ligand or indirectly through generation of endogenous or exogenous ligand (Sabroe et al, J Immunol 2003 p 1630-5). A TLR4 agonist is capable of causing a signaling response through a TLR-4 signaling pathway. A suitable example of a TLR4 agonist is a lipopolysaccharide, suitably a non-toxic derivative of lipid A, particularly monophosphoryl lipid A or more particularly 3-de-O-acylated monophoshoryl lipid A (3D-MPL).

3D-MPL is sold under the name MPL by GlaxoSmithKline Biologicals N.A. and is referred throughout the document as MPL or 3D-MPL see, for example, U.S. Pat. Nos. 4,436,727; 4,877,611; 4,866,034 and 4,912,094. 3D-MPL primarily promotes CD4+ T cell responses with an IFN-gamma (Th1) phenotype. 3D-MPL can be produced according to the methods disclosed in GB2220211A. Chemically it is a mixture of 3-de-O-acylated monophosphoryl lipid A with 3, 4, 5 or 6 acylated chains. In the compositions of the present invention small particle 3D-MPL may be used to prepare the immunogenic composition. Small particle 3D-MPL has a particle size such that it may be sterile-filtered through a 0.22 um filter. Such preparations are described in WO94/21292. Suitably, powdered 3D-MPL is used to prepare the immunogenic compositions of the present invention.

Other TLR4 agonists which can be used are alkyl glucosaminide phosphates (AGPs) such as those disclosed in WO98/50399 or U.S. Pat. No. 6,303,347 (processes for preparation of AGPs are also disclosed), suitably RC527 or RC529 or pharmaceutically acceptable salts of AGPs as disclosed in U.S. Pat. No. 6,764,840. Some AGPs are TLR4 agonists, and some are TLR4 antagonists.

Other suitable TLR4 agonists are as described in WO2003/011223 and in WO2003/099195, such as compound I, compound II and compound III disclosed on pages 4-5 of WO2003/011223 or on pages 3-4 of WO2003/099195 and in particular those compounds disclosed in WO2003/011223 as ER803022, ER803058, ER803732, ER804053, ER804057m ER804058, ER804059, ER804442, ER804680 and ER804764. For example, one suitable TLR-4 agonist is ER804057.

In a particular embodiment, the immunogenic composition comprises both a saponin and a TLR4 agonist. In a specific example, the immunogenic composition comprises QS21 and 3D-MPL.

A TLR-4 agonist, such as a lipopolysaccharide, such as 3D-MPL, can be used at amounts between 1 and 100 ug per human dose of the immunogenic composition. 3D-MPL may be used at a level of about 50 ug, for example between 40 to 60 ug, suitably between 45 to 55 ug or between 49 and 51 ug or 50 ug. In a further embodiment, the human dose of the immunogenic composition comprises 3D-MPL at a level of about 25 ug, for example between 20 to 30 ug, suitable between 21 to 29 ug or between 22 to 28 ug or between 23 and 27 ug or between 24 and 26 ug, or 25 ug.

A saponin, such as QS21, can be used at amounts between 1 and 100 ug per human dose of the immunogenic composition. QS21 may be used at a level of about 50 ug, for example between 40 to 60 ug, suitably between 45 to 55 ug or between 49 and 51 ug or 50 ug. In a further embodiment, the human dose of the immunogenic composition comprises QS21 at a level of about 25 ug, for example between 20 to 30 ug, suitable between 21 to 29 ug or between 22 to 28 ug or between 23 and 27 ug or between 24 and 26 ug, or 25 ug.

Where both TLR4 agonist and saponin are present in the immunogenic composition, then the weight ratio of TLR4 agonist to saponin is suitably between 1:5 to 5:1, suitably between 1:2 to 2:1, such as about 1:1. For example, where 3D-MPL is present at an amount of 50 ug or 25 ug, then suitably QS21 may also be present at an amount of 50 ug or 25 ug, respectively, per human dose of the immunogenic composition. Certain immunogenic compositions of the present invention comprise QS21 and 3D-MPL, at an amount of between 1 and 100 ug of each per human dose, such as at an amount of between 10 and 75 ug of each per human dose. Immunogenic compositions of the present invention may suitably comprise QS21 and 3D-MPL, at an amount of between 15 and 35 ug of each per human dose, such as at an amount of between 20 and 30 ug of each per human dose.

In one embodiment, the immunostimulant is a TLR9 agonist, for example as set out in WO2008/142133. In a specific example, said TLR9 agonist is an immunostimulatory oligonucleotide, in particular an oligonucleotide containing an unmethylated CpG motif. Such oligonucleotides are well known and are described, for example, in WO96/02555, WO99/33488 and U.S. Pat. No. 5,865,462. Suitable TLR9 agonists for use in the immunogenic compositions described herein are CpG containing oligonucleotides, optionally containing two or more dinucleotide CpG motifs separated by at least three, suitably at least six or more nucleotides. A CpG motif is a cytosine nucleotide followed by a guanine nucleotide.

In one embodiment the internucleotide bond in the oligonucleotide is phosphorodithioate, or possibly a phosphorothioate bond, although phosphodiester and other internucleotide bonds could also be used, including oligonucleotides with mixed internucleotide linkages. Methods for producing phosphorothioate oligonucleotides or phosphorodithioate are described in U.S. Pat. No. 5,666,153, U.S. Pat. No. 5,278,302 and WO95/26204. Oligonucleotides comprising different internucleotide linkages are contemplated, e.g. mixed phosphorothioate phophodiesters. Other internucleotide bonds which stabilise the oligonucleotide may be used.

Examples of CpG oligonucleotides suitable for inclusion in the immunogenic compositions described herein have the following sequences. In one embodiment, these sequences contain phosphorothioate modified internucleotide linkages.

```
OLIGO 1 (SEQ ID No: 9):
TCC ATG ACG TTC CTG ACG TT
(CpG 1826)

OLIGO 2 (SEQ ID No: 10):
TCT CCC AGC GTG CGC CAT
(CpG 1758)

OLIGO 3 (SEQ ID No: 11):
ACC GAT GAC GTC GCC GGT GAC GGC ACC ACG

OLIGO 4 (SEQ ID No: 12):
TCG TCG TTT TGT CGT TTT GTC GTT
(CpG 2006)

OLIGO 5 (SEQ ID No: 13):
TCC ATG ACG TTC CTG ATG CT
(CpG 1668)
```

Alternative CpG oligonucleotides may comprise the sequences above in that they have inconsequential deletions or additions thereto.

In one embodiment the immunostimulant is a tocol. Tocols are well known in the art and are described in EP0382271. In a particular embodiment, the tocol is alpha-tocopherol or a derivative thereof such as alpha-tocopherol succinate (also known as vitamin E succinate).

The present invention also provides a process for making an immunogenic composition of the invention comprising the steps:
  a. lyophilising an Rv1196 related antigen; and
  b. reconstituting the lyophilised Rv1196 related antigen of step a) with an aqueous solution wherein the conductivity of the solution is 13 mS/cm or lower.

In certain embodiments the conductivity of the aqueous solution is 12 mS/cm or lower, for example 10 mS/cm or lower, 8 mS/cm or lower, 6 mS/cm or lower, 5 mS/cm or lower, 4 mS/cm or lower, or 3 mS/cm or lower. In a particular embodiment the conductivity of the aqueous solution is 2.5 mS/cm or lower, such as 2.25 mS/cm or lower, or 2.0 mS/cm or lower.

Suitably, the conductivity of the aqueous solution is such that when the lyophilised antigen is reconstituted the resulting solution has a conductivity of 13 mS/cm or lower, such as 12 mS/cm or lower, for example 10 mS/cm or lower, 8 mS/cm or lower, 6 mS/cm or lower, 5 mS/cm or lower, 4 mS/cm or lower, or 3 mS/cm or lower. In a particular embodiment the conductivity of the resulting solution is 2.5 mS/cm or lower, such as 2.25 mS/cm or lower, or 2.0 mS/cm or lower.

Further provided is a process for making an immunogenic composition of the invention comprising the steps:
  a. lyophilising an RV1196 related antigen; and
  b. reconstituting the lyophilised Rv1196 related antigen of step a) with an aqueous solution wherein the concentration of salts in said solution is 130 mM or lower.

In certain embodiments the concentration of salts in said aqueous solution is 100 mM or lower, for example 90 mM or lower, 80 mM or lower, 70 mM or lower, 60 mM or lower, 50 mM or lower, or 40 mM or lower. In a particular embodiment the concentration of salts in said aqueous solution is 35 mM or lower, such as 30 mM or lower, or 25 mM or lower.

Suitably, the concentration of salts in the aqueous solution is such that when the lyophilised antigen is reconstituted the resulting solution has a concentration of salts of 130 mM or lower, such as 100 mM or lower, for example 90 mM or lower, 80 mM or lower, 70 mM or lower, 60 mM or lower, 50 mM or lower, or 40 mM or lower. In a particular embodiment the concentration of salts in the resulting solution is 35 mM or lower, such as 30 mM or lower, or 25 mM or lower.

Additionally provided is a process for making an immunogenic composition of the invention comprising the steps:
 a. lyophilising an Rv1196 related antigen; and
 b. reconstituting the lyophilised Rv1196 related antigen of step a) with an aqueous solution wherein the concentration of sodium chloride in said solution is 130 mM or lower.

In certain embodiments the concentration of sodium chloride in said aqueous solution is 100 mM or lower, for example 90 mM or lower, 80 mM or lower, 70 mM or lower, 60 mM or lower, 50 mM or lower, or 40 mM or lower. In a particular embodiment the concentration of salts in said aqueous solution is 35 mM or lower, such as 30 mM or lower, 20 mM or lower, or 15 mM or lower. Suitably the concentration of sodium chloride in the aqueous solution is at or below 5 mM.

Suitably, the concentration of sodium chloride in the aqueous solution is such that when the lyophilised antigen is reconstituted the resulting solution has a concentration of sodium chloride of 130 mM or lower, such as 100 mM or lower, for example 90 mM or lower, 80 mM or lower, 70 mM or lower, 60 mM or lower, 50 mM or lower, or 40 mM or lower. In a particular embodiment the concentration of sodium chloride in the resulting solution is 35 mM or lower, such as 30 mM or lower, or 25 mM or lower.

In one embodiment the aqueous solutions of step b) (above) comprise a saponin and/or a TLR4 agonist, for example QS21 and/or 3D-MPL. In a further embodiment the saponin and/or TLR4 agonist are in a liposomal formulation. In one embodiment, the aqueous solutions comprise a TLR4 agonist and a saponin in a liposomal formulation, and a non-ionic tonicity agent as described herein, such as a polyol. In particular the aqueous solutions may comprise sorbitol.

Also provided is a kit comprising:
 a. a lyophilised Rv1196 related antigen; and
 b. an aqueous solution wherein the conductivity of the solution is 13 mS/cm or lower.

In certain embodiments the conductivity of the aqueous solution is 12 mS/cm or lower, for example 10 mS/cm or lower, 8 mS/cm or lower, 6 mS/cm or lower, 5 mS/cm or lower, 4 mS/cm or lower, or 3 mS/cm or lower. In a particular embodiment the conductivity of the aqueous solution is 2.5 mS/cm or lower, such as 2.25 mS/cm or lower, or 2.0 mS/cm or lower.

Suitably, the conductivity of the aqueous solution is such that when the lyophilised antigen is reconstituted the resulting solution has a conductivity of 13 mS/cm or lower, such as 12 mS/cm or lower, for example 10 mS/cm or lower, 8 mS/cm or lower, 6 mS/cm or lower, 5 mS/cm or lower, 4 mS/cm or lower, or 3 mS/cm or lower. In a particular embodiment the conductivity of the resulting solution is 2.5 mS/cm or lower, such as 2.25 mS/cm or lower, or 2.0 mS/cm or lower.

Additionally provided is a kit comprising:
 a. a lyophilised Rv1196 related antigen; and
 b. an aqueous solution wherein the concentration of salts in said solution is 130 mM or lower.

In certain embodiments the concentration of salts in said aqueous solution is 100 mM or lower, for example 90 mM or lower, 80 mM or lower, 70 mM or lower, 60 mM or lower, 50 mM or lower, or 40 mM or lower. In a particular embodiment the concentration of salts in said aqueous solution is 35 mM or lower, such as 30 mM or lower, or 25 mM or lower.

Suitably, the concentration of salts in the aqueous solution is such that when the lyophilised antigen is reconstituted the resulting solution has a concentration of salts of 130 mM or lower, such as 100 mM or lower, for example 90 mM or lower, 80 mM or lower, 70 mM or lower, 60 mM or lower, 50 mM or lower, or 40 mM or lower. In a particular embodiment the concentration of salts in the resulting solution is 35 mM or lower, such as 30 mM or lower, or 25 mM or lower.

Further, there is provided a kit comprising:
 a. a lyophilised Rv1196 related antigen; and
 b. an aqueous solution wherein the concentration of sodium chloride in said solution is 130 mM or lower.

In certain embodiments the concentration of sodium chloride in said aqueous solution is 100 mM or lower, for example 90 mM or lower, 80 mM or lower, 70 mM or lower, 60 mM or lower, 50 mM or lower, or 40 mM or lower. In a particular embodiment the concentration of salts in said aqueous solution is 35 mM or lower, such as 30 mM or lower, 20 mM or lower, or 15 mM or lower. Suitably the concentration of sodium chloride in the solution is at or below 5 mM.

Suitably, the concentration of sodium chloride in the aqueous solution is such that when the lyophilised antigen is reconstituted the resulting solution has a concentration of sodium chloride of 130 mM or lower, such as 100 mM or lower, for example 90 mM or lower, 80 mM or lower, 70 mM or lower, 60 mM or lower, 50 mM or lower, or 40 mM or lower. In a particular embodiment the concentration of sodium chloride in the resulting solution is 35 mM or lower, such as 30 mM or lower, or 25 mM or lower.

Kits may be adapted to provide a single dose of the immunogenic composition, such as a single human dose, or multiple doses of the immunogenic composition.

The aqueous solutions used in kits of the invention may be any of the aqueous solutions as defined herein. In a specific embodiment of the invention, the aqueous solution comprises a TLR4 agonist and/or a saponin in the form of liposomes. In a particular embodiment, the TLR4 agonist is 3D-MPL and the saponin is QS21. The aqueous solutions used herein may comprise a tonicity agent, for example a polyol, such a sorbitol.

In respect of the above mentioned kits and methods for the production of immunogenic compositions of the invention, it may be noted that immunostimulant(s) and tonicity agent(s) if present may be colyophilised with the antigen or contained with the aqueous solution as desired. The aqueous solution may simply be water for injection and all other components of the immunogenic composition are colyophilised with the antigen. Typically, at least some immunostimulant(s) and tonicity agent(s) are provided in the aqueous solution, which is particularly appropriate if certain components are poorly compatible with lyophilisation such as liposomes. In one embodiment the aqueous solution comprises an immunostimulant. In a second embodiment the aqueous solution comprises a tonicity agent, e.g. a non-ionic tonicity agent, such as a polyol, in particular sorbitol. In a third embodiment the aqueous solution comprises an immunostimulant and a tonicity agent, such as a polyol, in particular sorbitol.

Kits may further comprise instructions directing the reconstitution of the lyophilised Rv1196 related antigen using the aqueous solution.

The immunogenic compositions according the invention may be used in medicine, in particular for the prophylaxis, treatment or amelioration of infection by mycobacteria, such as infection by *Mycobacterium tuberculosis*. The immunogenic compositions will generally be provided for administration to humans, though they may also be of value in veterinary medicine such as for administration to bovines.

There is provided the use of an immunogenic composition according to the invention in the manufacture of a medicament, in particular a medicament for the prophylaxis, treatment or amelioration of infection by mycobacteria, such as infection by *Mycobacterium tuberculosis*.

There is also provided a method for the prophylaxis, treatment or amelioration of infection by mycobacteria, such as infection by *Mycobacterium tuberculosis*, comprising the administration of a safe and effective amount of an immunogenic composition according to the present invention.

The immunogenic composition may be provided for the purpose of:
- treating active tuberculosis;
- prophylaxis of active tuberculosis, such as by administering to a subject who is uninfected, or alternatively a subject who has latent infection;
- treating latent tuberculosis;
- prophylaxis of latent tuberculosis, such as by administering to a subject who is uninfected; or
- preventing or delaying reactivation of tuberculosis, especially the delay of TB reactivation, for example by a period of months, years or even indefinitely.

The term "active infection" refers to an infection, e.g. infection by *M. tuberculosis*, with manifested disease symptoms and/or lesions, suitably with manifested disease symptoms.

The terms "inactive infection", "dormant infection" or "latent infection" refer to an infection, e.g. infection by *M. tuberculosis*, without manifested disease symptoms and/or lesions, suitably without manifested disease symptoms. A subject with latent infection will suitably be one which tests positive for infection, e.g. by PPD or T cell based assays, but which has not demonstrated the disease symptoms and/or lesions which are associated with an active infection.

The term "primary tuberculosis" refers to clinical illness, e.g., manifestation of disease symptoms, directly following infection, e.g. infection by *M. tuberculosis*. See, *Harrison's Principles of Internal Medicine*, Chapter 150, pp. 953-966 (16th ed., Braunwald, et al., eds., 2005).

The terms "secondary tuberculosis" or "postprimary tuberculosis" refer to the reactivation of a dormant, inactive or latent infection, e.g. infection by *M. tuberculosis*. See, *Harrison's Principles of Internal Medicine*, Chapter 150, pp. 953-966 (16th ed., Braunwald, et al., eds., 2005).

The term "tuberculosis reactivation" refers to the later manifestation of disease symptoms in an individual that tests positive for infection (e.g. in a tuberculin skin test, suitably in an in vitro T cell based assay) test but does not have apparent disease symptoms. Suitably the individual will not have been re-exposed to infection. The positive diagnostic test indicates that the individual is infected, however, the individual may or may not have previously manifested active disease symptoms that had been treated sufficiently to bring the tuberculosis into an inactive or latent state.

Suitability an immunogenic composition is administered to a subject who is uninfected or who has a latent infection by mycobacteria, such as infection by *Mycobacterium tuberculosis*.

The volume of immunogenic composition administered may vary depending upon a number of other factors, such as the specific delivery route, e.g. intramuscular, subcutaneous or intradermal. Typically, the volume administered in a single injection (the unit dose) for a human will be in the range of 50 ul to 1 ml, such as 100 ul to 750 ul, especially 400 to 600 ul, for example about 500 ul.

The quantity of Rv1196 related antigen contained within a single dose is dependent upon clinical needs but a single human dose will typically be in the range of 1 to 100 ug, such as 5 to 50 ug, for example 5 to 20 ug. A single human dose may contain about 10 ug of Rv1196 related antigen.

Suitably, compositions of the invention will be stable, in which is meant that during storage at 25° C. for a period of 24 hours antigenicity as measured by the techniques described herein remains at least 80% of the antigenicity before storage. Desirably, antigenicity will remain at least 85%, such as at least 90% and in particular at least 95% after storage at 25° C. for a period of 24 hours. For compositions of particular interest, at least 80% of the antigenicity of the composition, such as at least 85%, at least 90% and especially at least 95% remains after storage at 30° C. for a period of 24 hours.

The present invention will now be further described by means of the following non-limiting examples.

EXAMPLES

Example 1

Preparation of Adjuvant Composition ASA (Sorbitol)

An adjuvant composition was prepared which comprised 3-de-O-acylated monophosphoryl lipid A and QS21 in a liposomal formulation using sorbitol as a tonicity agent. This was prepared as follows:

A. Method of Preparation of Liposomes:

A mixture of lipid (DOPC), cholesterol and 3-de-O-acylated monophosphoryl lipid A in organic solvent was dried down under vacuum. An aqueous solution (phosphate buffered saline [100 mM NaCl, 50 mM Phosphate pH 6.1]) was then added and the vessel agitated until all the lipid was in suspension. This suspension was then prehomogenised with high shear mixer and then high pressure homogenised until the liposome size was reduced to around 90 nm±10 nm measured by DLS. Liposomes were then sterile filtered.

B. ASA Formulation:

Step 1: Dilution of Concentrated Liposomes $Na_2$/K Phosphate buffer 100 mM pH 6.1 when diluted 10 times was added to water for injection to reach a 10 mM phosphate buffer concentration in the final formulation. A 30% (w/v) sorbitol solution in water for injection (WFI) was then added to reach a concentration of 4.7% in the final formulation—this was stirred for 15 to 45 minutes at room temperature.

Concentrated liposomes (made of DOPC, cholesterol and 3D-MPL at 40 mg/ml, 10 mg/ml and 2 mg/ml respectively) were then added to the mix to reach a concentration of 100 ug/ml of 3D-MPL in the final formulation.

The mixture was subsequently stirred for 15 to 45 minutes at room temperature.

Step 2: QS21 Addition

Using a peristaltic pump, QS21 bulk stock was added to the diluted liposomes under magnetic stirring to reach a 100 ug/ml concentration in the final formulation. The mix was stirred for 15 to 45 minutes.

Final ASA (sorbitol) formulation contained 2 mg DOPC, 500 ug cholesterol, 100 ug 3D-MPL/ml and 100 ug QS21/ml, 4.7% sorbitol and 5 mM sodium chloride and 10 mM phosphate.

Step 3: pH was Checked to be 6.1±0.1
Step 4: Sterile Filtration
Sterile filtration was performed using a polyethersulfone (PES) filter from PALL Corporation.
Step 5: Storage at +2° C. to +8° C.

The adjuvant composition obtained, which comprised 3-de-O-acylated MPL and QS21 in a liposomal formulation and containing sorbitol as a tonicity agent (designated ASA (sorbitol)), was then stored at 4° C.

Example 2

Preparation of Adjuvant Composition ASA (150 mM NaCl)

An adjuvant composition was prepared which comprised 3-de-O-acylated monophosphoryl lipid A and QS21 in a liposomal formulation using sodium chloride as a tonicity agent.
A. Method of Preparation of Liposomes:
A mixture of lipid (DOPC), cholesterol and 3-de-O-acylated monophosphoryl lipid A (3D-MPL) in organic solvent was dried down under vacuum. Phosphate buffered saline (100 mM NaCl, 50 mM Phosphate pH 6.1) was then added and the vessel agitated until all the lipid was in suspension. This suspension was then prehomogenised with high shear mixer and then high pressure homogenised until the liposomes size was reduced to around 90 nm±10 nm measured by DLS. Liposomes were then sterile filtered on 0.22 um PES membrane.
B. ASA Formulation:
Step 1: Dilution of Concentrated Liposomes
Na$_2$/K Phosphate buffer 100 mM pH 6.45 when diluted 10 times and NaCl 1.5 M were added to water for injection to reach respectively 10 mM phosphate and NaCl 150 mM concentrations in the final formulation. This mixture was stirred for 5 minutes at room temperature. Concentrated liposomes (made of DOPC, cholesterol and 3D-MPL at 40 mg/ml, 10 mg/ml and 2 mg/ml respectively) were then added to the mix to reach a concentration of 100 ug/ml of 3D-MPL in the final formulation. The mixture was subsequently stirred for 5 to 15 minutes at room temperature.
Step 2: QS21 Addition
QS21 bulk stock was added to the diluted liposomes under magnetic stirring to reach a 100 ug/ml concentration in the final formulation. The mix was stirred at room temperature.
Step 3: ph was Checked so as to be 6.1±0.1.
Step 4: Sterile Filtration
Sterile filtration was performed using a polyethersulfone (PES) filter from PALL Corporation.
Step 5: Storage at +2° C. to +8° C.

Final composition of ASA (150 mM NaCl) was 2 mg DOPC, 500 ug cholesterol, 100 ug 3-de-O-acylated MPL, 100 ug QS21 per 1 ml, with 10 mM phosphate and 150 mM NaCl.

Example 3

QS21 Lytic Activity

QS21 is known to lyse red blood cells (RBC). The ASA (sorbitol) adjuvant composition prepared as in Example 1 was tested to ensure that QS21 lytic activity was quenched in the same way as was seen with the equivalent adjuvant composition comprising 150 mM NaCl (ASA (150 mM NaCl)).

QS21 lytic activity was measured by a haemolysis assay using chicken Red Blood cells (RBC). RBC were centrifuged at 550 g at 4° C. Supernatant was discarded. The pellet was carefully resuspended in PBS buffer to reach the initial volume and the same operation was repeated until supernatant was no longer red (generally 3 times). The pellet was stored at 4° C. for 3 to 4 days maximum if not used directly (and washed again the day it is used) or was diluted around 10 times in buffer if used the same day.

A QS21 dose range curve was prepared in ASA buffer (in salt or in sorbitol buffer following the ASA sample tested) extemporaneously and the adjuvant samples (containing a 50 ug or 90 ug equivalent of QS21 meaning the equivalent of 500 ul or 900 ul ASA) were prepared. Final volume was adjusted to 900 ul in standards and samples with adequate buffer (containing or not sorbitol as a function of the buffer of the sample tested). Due to its opalescence, ASA interferes with optical density (OD). ASA "blanks" were thus prepared and their OD was subtracted from the OD of ASA tested samples. Those blanks corresponded to the same ASA volume as the volume tested in samples, but adjusted to 1 ml with buffer. No RBC were added to these blanks. Standards and samples were then incubated with RBC (100 ul of diluted RBC added to 900 ul of standards and samples) for 30 minutes at room temperature (RT). Samples were then centrifuged 5 minutes at 900 g. Optical density at 540 nm was measured after centrifugation.

Determination of lytic activity was carried out by a limit test.
1. Limit of detection (LOD) was defined as the lowest concentration of QS21 leading to an OD:
Higher than the base level (OD>0.1)
Around three times higher than OD's buffer (the "0 ug" QS21)
In the ascendant part of the curve
Determined for each test.
2. QS21 lytic activity was held to be positive in the adjuvant samples if the OD for the adjuvant sample was greater than the OD$_{LOD}$).

| Example QS21 curve | | |
|---|---|---|
| ug QS21 | OD | QS21 quenched |
| 0 | 0.029 | NA |
| 0.5 | 0.052 | <LOD |
| 0.6 | 0.073 | <LOD |
| 0.7 | 0.091 | <LOD |
| 0.8 | 0.096 | <LOD |
| 0.9 | 0.12 | >98.2% |
| 1 | 0.195 | >98% |
| 1.1 | 0.212 | >97.8% |
| 1.2 | 0.348 | >97.6% |
| 1.3 | 0.479 | >97.4% |
| 1.4 | 0.612 | >97.2% |
| 1.5 | 0.669 | >97% |
| 2 | 1.139 | >96% |
| 2.5 | 1.294 | >95% |
| 3 | 1.391 | >94% |
| 5 | 1.416 | >90% |
| Adjuvant* | 0.03 | >98.2% |

*50 ug QS21 equivalent tested. 150 mM sodium chloride buffer.

The above data is shown graphically in FIG. 1.
The Limit of Detection in this assay is at 0.9 ug QS21, and OD of 0.12

The QS21 quenching in an adjuvant composition comprising 150 mM sodium chloride was estimated to be more than 98.2% for the equivalent of 50 ug QS21 tested. In the case of an equivalent of 90 ug tested, conclusion is more than 99%.

QS21 quenching was then compared with an equivalent adjuvant composition comprising sorbitol and only 5 mM sodium chloride. Data were generated after storage of the ASA at 4° C. or after accelerated stability (7 days at 37° C.).

For the ASA in sorbitol, the QS21 standard curve was realised in a sorbitol containing buffer.

| Sample | Timepoint | LOD | QS21 quenched |
|---|---|---|---|
| Adjuvant composition (ASA) 150 mM NaCl | T0 | <1.4 | >97.2% |
| | 7 days 37° C. | <0.9 | >98.2% |
| Adjuvant Composition (ASA) sorbitol, 5 mM NaCl | T0 | <2 | >97.8% |
| | 7 days 37° C. | <1 | >96% |
| | 11 months 4° C. | <2 | >97.8%* |

Equivalent of 50 ug QS21 tested except * equivalent of 90 ug QS21 tested.

It was concluded that QS21 was adequately quenched in a low sodium chloride buffer.

Example 4

MPL Congeners

Chemically, 3D-MPL is a mixture of 3-de-O-acylated monophosphoryl lipid A with mainly 4, 5 or 6 acylated chains. Each separate 3D-MPL molecule is called a congener. It is important that the congener composition remain constant, with no shift between the proportion of congeners. It is also important that any buffer used enables the congener composition to be the same as in the concentrated liposomes used to make the adjuvant composition.

Figure 2:
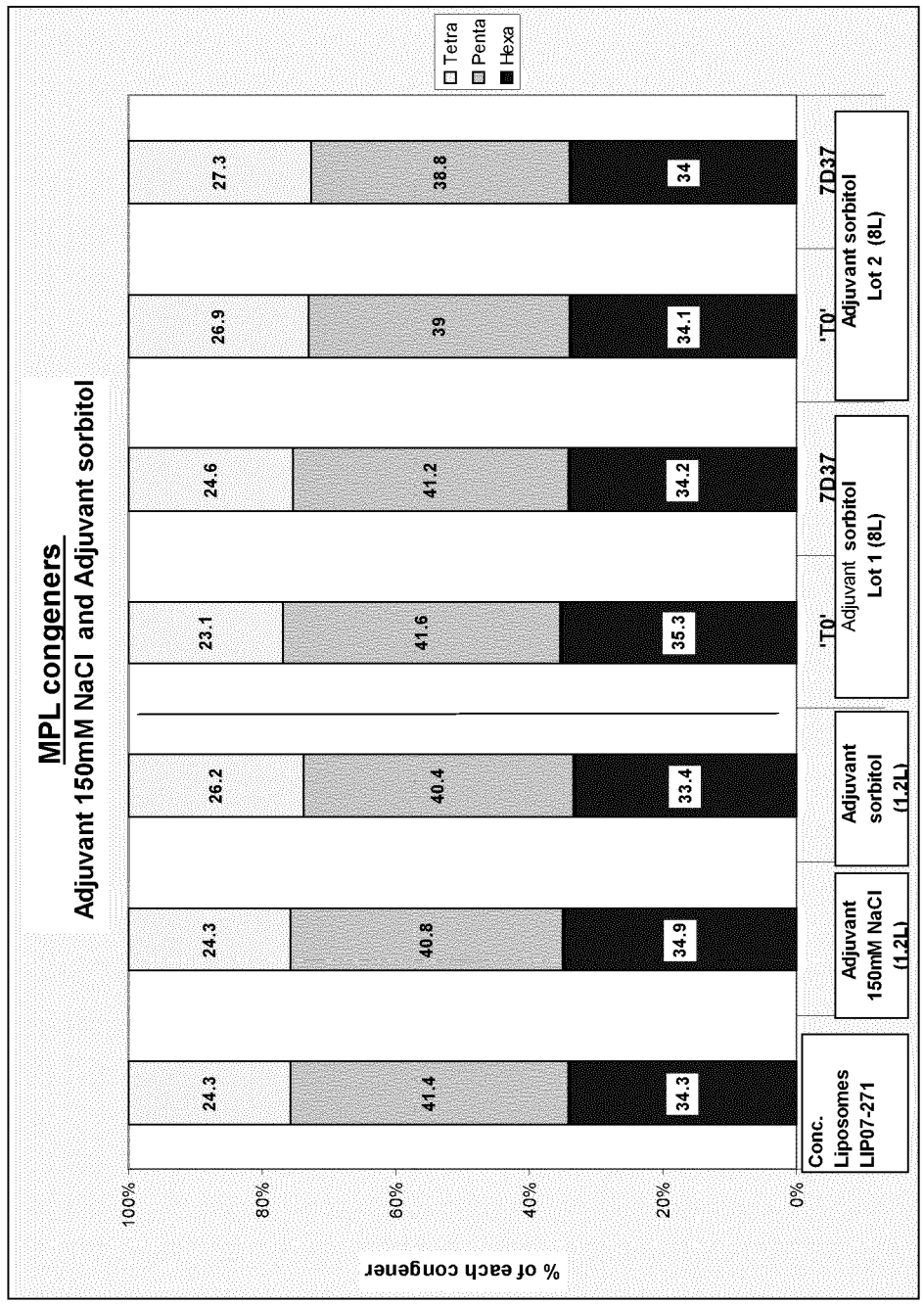
FIG. 2. Percentage of each 3D-MPL congener in the different ASA formulations
Figure 3:
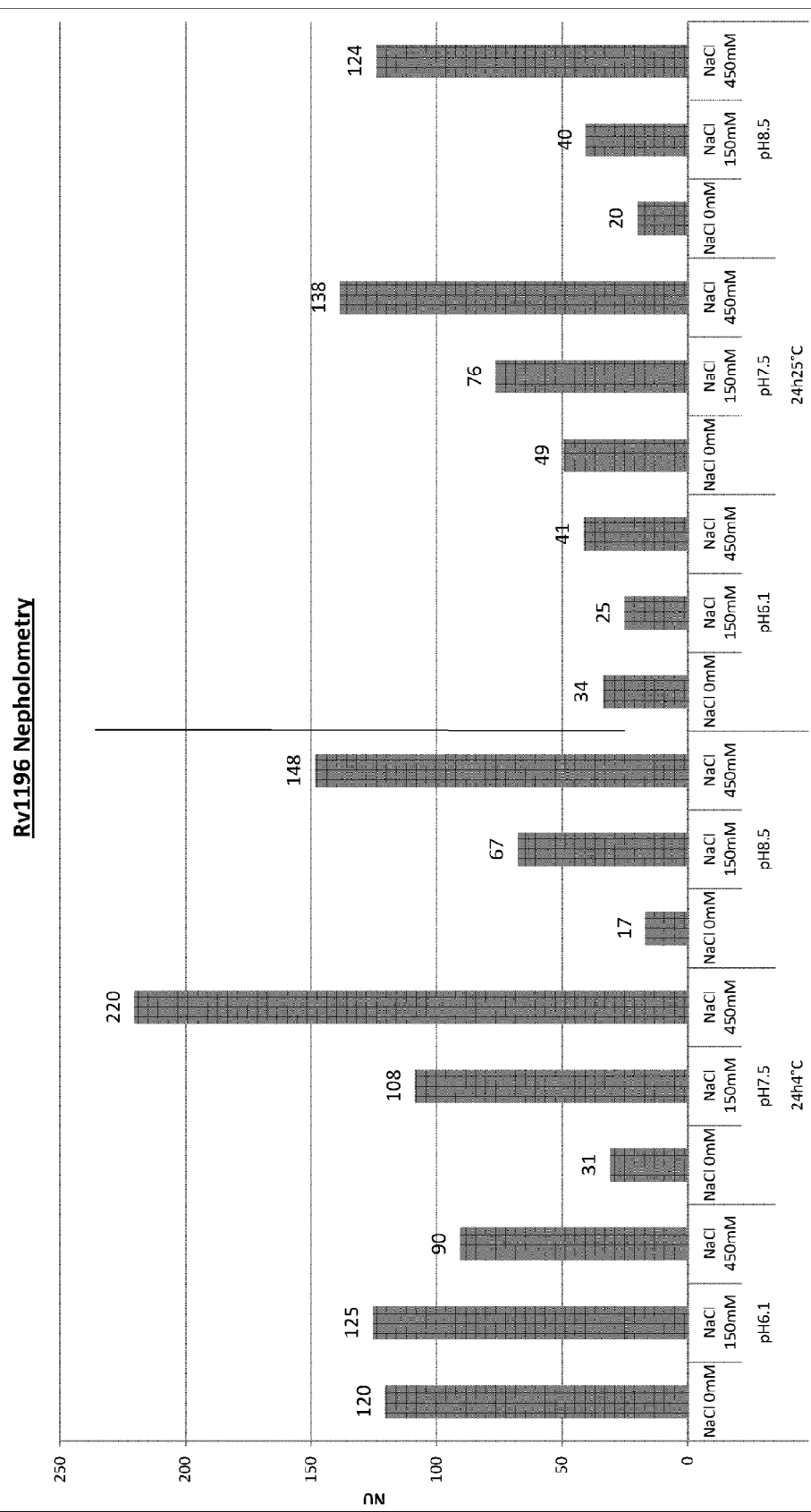
FIG. 3. Nepholometry of immunogenic compositions with varied pH and NaCl concentrations after storage FIG. 4. DLS of immunogenic compositions with varied pH and NaCl concentrations after storage FIG. 5. DLS of immunogenic compositions with varied pH and NaCl concentrations after storage FIG. 6. Nepholometry of immunogenic compositions with varied pH and NaCl concentrations after storage FIG. 7. Antigenic stability of immunogenic compositions with varied pH and NaCl concentrations following after storage FIGS. 8a-8d. SEC-HPLC analysis of immunogenic compositions with varied pH and NaCl concentrations after storage FIG. 9. Antigenicity of immunogenic compositions with varied pH and NaCl concentrations after storage FIG. 10. Conductivity of NaCl standard solutions FIG. 11. Induction of CD4 T cell responses in mice using immunogenic compositions of the invention FIG. 12. Induction of CD8 T cell responses in mice using immunogenic compositions of the invention FIG. 13. Nepholometry of immunogenic compositions with varied pH and NaCl concentrations after storage FIG. 14. DLS of immunogenic compositions with varied pH and NaCl concentrations after storage FIG. 15. Antigenicity of immunogenic compositions with varied NaCl concentrations after storage
Figure 4:
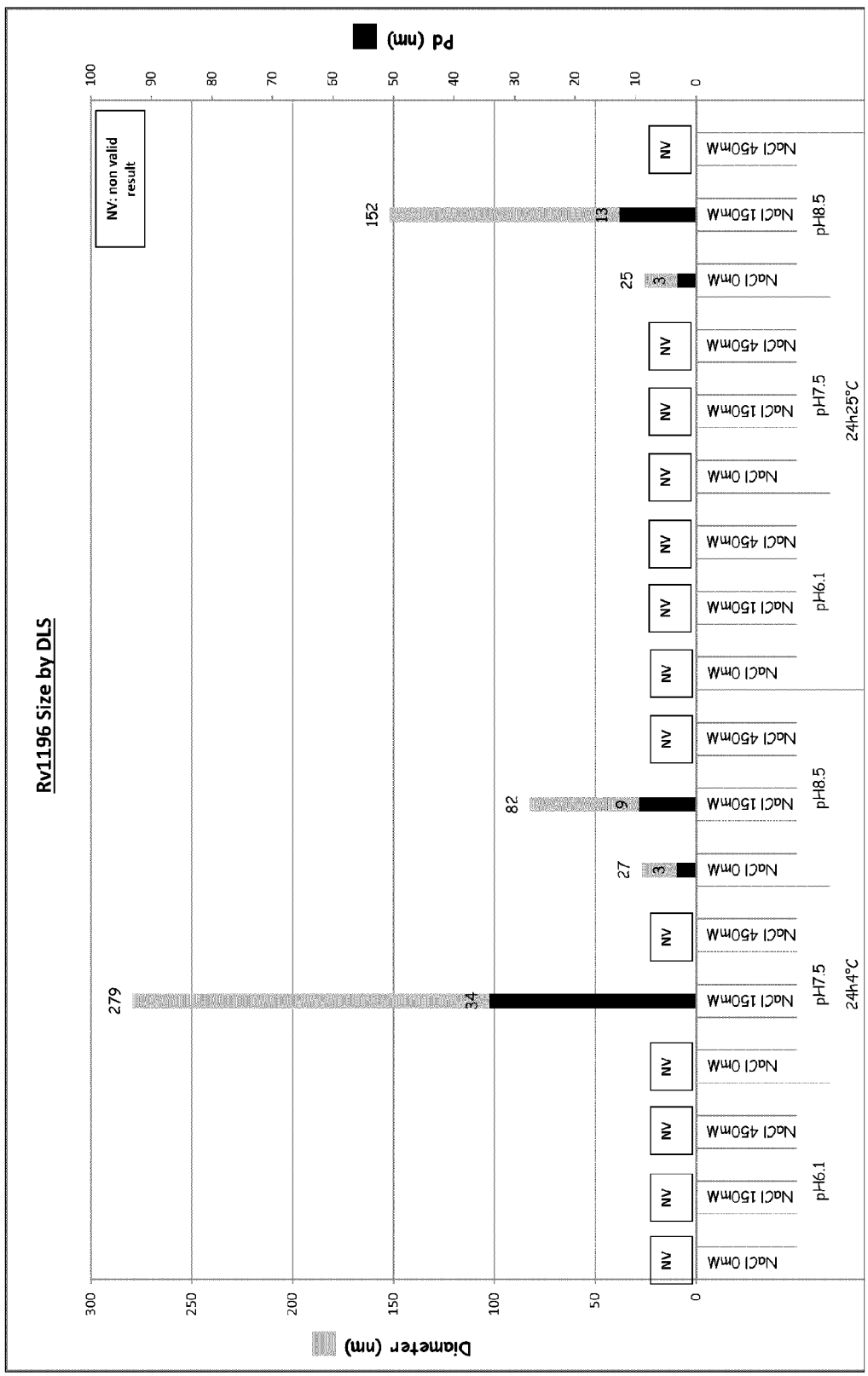

As shown on FIG. 2, the congener composition was examined in 3D-MPL concentrated liposomes (Conc. Liposomes LIP07-217, first column of FIG. 2), an adjuvant composition comprising 3D-MPL liposomes and QS21 in a 150 mM NaCl buffer (Adjuvant 150 mM NaCl, or ASA (150 mM NaCl), second column), and an adjuvant composition comprising 3D-MPL liposomes and QS21 in a sorbitol and 5 mM NaCl buffer (Adjuvant Sorbitol, or ASA (sorbitol), columns 3-7).

The congener composition was also examined in two lots of ASA (sorbitol) adjuvant at day 0 and 7 days after preparation and maintenance at 37° C. to ensure that there was no evolution over time (see final four columns of FIG. 2).

Relative distribution of tetra-, penta- and hexa-acylated congeners of MPL in concentrated liposomes or ASA (sorbitol) samples was determined by IP-HPLC-Fluo detection (ARD). Both standards and samples were derivatised with dansylhydrazine, which introduces a Fluo-active chromophore on the dissacharide backbone. The derivatised samples were analysed on a C18 reverse phase column using tetrabutylammonium hydroxide (TBAOH) as an ion pair reagent. Congeners containing the same numbers of fatty acyl groups were eluted in distinct groups (tetraacyl, pentaacyl, and hexaacyl).

Distribution of congeners is deduced by comparing the peak area of each group to the total peak area of all MPL congeners.

FIG. 2 shows the percentage of each congener. No significant difference in congener composition was found between adjuvant buffers, and the congener composition was consistent over time in the sorbitol buffer.

Example 5

Preparation of Adjuvant Composition ASA (Sorbitol-2)

An adjuvant composition was prepared which comprised 3-de-O-acylated monophosphoryl lipid A and QS21, at a reduced level relative to Example 1, in a liposomal formulation using sorbitol as a tonicity agent. This was prepared as follows:

The adjuvant was prepared by 1:1 dilution of ASA (sorbitol), prepared according to Example 1, with a solution containing 10 mM phosphate, 5 mM NaCl, 4.7% sorbitol at pH 6.1.

Final ASA (sorbitol-2) formulation contained 1 mg DOPC, 250 ug cholesterol, 50 ug 3D-MPL/ml and 50 ug QS21/ml, 4.7% sorbitol, 5 mM sodium chloride and 10 mM phosphate.

Example 6

Preparation of Adjuvant Composition ASA (Sorbitol-3)

An adjuvant composition was prepared which comprised 3-de-O-acylated monophosphoryl lipid A and QS21, at a reduced level relative to Example 1, in a liposomal formulation using sorbitol as a tonicity agent. This was prepared as follows:

A. Method of Preparation of Liposomes:

A mixture of lipid (DOPC), cholesterol and 3-de-O-acylated monophosphoryl lipid A in organic solvent was dried down under vacuum. An aqueous solution (phosphate buffered saline [100 mM NaCl, 50 mM Phosphate pH 6.1]) was then added and the vessel agitated until all the lipid was in suspension. This suspension was then prehomogenised with high shear mixer and then high pressure homogenised until the liposomes size was reduced to around 90 nm±10 nm measured by DLS. Liposomes were then sterile filtered.

B. ASA Formulation:

Step 1: Dilution of Concentrated Liposomes $Na_2$/K Phosphate buffer 100 mM pH 6.1 when diluted 10 times was added to water for injection to reach a 10 mM phosphate buffer concentration in the final formulation. A 30% (w/v) sorbitol solution in water for injection (VVFI) was then added to reach a concentration of 4.7% in the final formulation—this was stirred for 15 to 45 minutes at room temperature.

Concentrated liposomes (made of DOPC, cholesterol and 3D-MPL at 40 mg/ml, 10 mg/ml and 2 mg/ml respectively) were then added to the mix to reach a concentration of 50 ug/ml of 3D-MPL in the final formulation.

The mixture was subsequently stirred for 15 to 45 minutes at room temperature.

Step 2: QS21 Addition

Using a peristaltic pump, QS21 bulk stock was added to the diluted liposomes under magnetic stirring to reach a 50 ug/ml concentration in the final formulation. The mix was stirred for 15 minutes.

Final ASA formulation contained 1 mg DOPC, 250 ug cholesterol, 50 ug 3D-MPL/ml and 50 ug QS21/ml, 4.7% sorbitol and 2.5 mM sodium chloride, 10 mM phosphate.

Step 3: pH was Checked to be 6.1±0.1

Step 4: Sterile Filtration

Sterile filtration was performed using a polyethersulfone (PES) filter from PALL Corporation.

Step 5: Storage at +2° C. to +8° C.

The adjuvant composition obtained, which comprised 3-de-O-acylated MPL and QS21 in a liposomal formulation and containing sorbitol as a tonicity agent (designated ASA (sorbitol-3)), was then stored at 4° C.

Example 7

Preparation of Adjuvant Composition ASA (150 mM NaCl-2)

An adjuvant composition was prepared which comprised 3-de-O-acylated monophosphoryl lipid A and QS21, at a reduced level relative to Example 2, in a liposomal formulation using sodium chloride as a tonicity agent. This was prepared as follows:
A. Method of Preparation of Liposomes:
A mixture of lipid (DOPC), cholesterol and 3-de-O-acylated monophosphoryl lipid A (3D-MPL) in organic solvent was dried down under vacuum. Phosphate buffered saline (100 mM NaCl, 50 mM Phosphate pH 6.1) was then added and the vessel agitated until all the lipid was in suspension. This suspension was then prehomogenised with high shear mixer and then high pressure homogenised until the liposomes size was reduced to around 90 nm±10 nm measured by DLS. Liposomes were then sterile filtered on 0.22 um PES membrane.
B. ASA Formulation:
Step 1: Dilution of Concentrated Liposomes
$Na_2$/K Phosphate buffer 100 mM pH 6.45 when diluted 10 times and NaCl 1.5 M were added to water for injection to reach respectively 10 mM phosphate and NaCl 150 mM concentrations in the final formulation. This mixture was stirred for 5 minutes at room temperature. Concentrated liposomes (made of DOPC, cholesterol and 3D-MPL at 40 mg/ml, 10 mg/ml and 2 mg/ml respectively) were then added to the mix to reach a concentration of 50 ug/ml of 3D-MPL in the final formulation. The mixture was subsequently stirred for 5 to 15 minutes at room temperature.
Step 2: QS21 Addition
QS21 bulk stock was added to the diluted liposomes under magnetic stirring to reach a 50 ug/ml concentration in the final formulation. The mix was stirred at room temperature.
Step 3: ph was checked so as to be 6.1±0.1.
Step 4: Sterile Filtration
Sterile filtration was performed using a polyethersulfone (PES) filter from PALL Corporation.
Step 5: Storage at +2° C. to +8° C.
Final composition of ASA (150 mM NaCl-2) was 1 mg DOPC, 250 ug cholesterol, 50 ug 3-de-β-acylated MPL, 50 ug QS21 per 1 ml, 10 mM phosphate and 150 mM NaCl.

Example 8

Investigation of "Salting Out" in Compositions Comprising Rv1196 with Different Salt Concentrations at pH 6.1, 7.5 and 8.5

The impact of sodium chloride concentration and pH on Rv1196 antigen stability, as assessed by size, was investigated.

Method

Rv1196 protein (SEQ ID No: 1) was obtained from Corixa Corporation and was diluted to a concentration of 100 ug/ml in three different buffers (10 mM phosphate buffer at pH 6.1, 20 mM Tris buffer at pH 7.5 and 20 mM Tris buffer at pH 8.5) containing final sodium chloride concentrations of 0, 150 and 450 mM.

Samples were stored for 24 hours at 4° C. or 25° C. before analysis.

Nephlometry was performed using a Nepheloskan® Ascent, available from Thermo Fischer Scientific. Analysis was performed in UV transparent Costar® micro-plates available from Corning Inc (USA).

DLS was performed using a Dynapro Plate Reader from Wyatt Instruments. The instrument was operated using a laser wavelength of 830 nm and power of 50 mW. Scattered light was detected at 150° at a temperature of 22° C. The mean hydrodynamic diameter and polydispersity index (p1) are calculated by the instrument software.

Results

The findings of this experiment are presented in FIGS. 3 and 4.

Nephlometry demonstrates a general trend of deceased clarity with increasing salt concentration, indicating that Rv1196 is sensitive to salt concentration.

For the majority of DLS samples, instrumentation was unable to determine a specific particle size (shown as NV in FIG. 4). Nevertheless, where comparable data was obtained (i.e. pH 8.5 with 0 or 150 nM NaCl), it is clear that the concentration of sodium chloride impacts the measured particle size in Rv1196 immunogenic compositions.

Example 9

Preparation of Protein Antigens

M72 with Two N-Terminal his Residues (SEQ ID No: 7)

Construction of the M72 Expression Vector

A plasmid coding for the amino acid sequence of Mtb72f with an additional 6-His tag at the N-terminus was generated by the sequential linkage in tandem of the open reading frames (ORFS) encoding the C terminal fragment of Mtb32a to the full length ORF of Mtb39a followed at the C terminus with the N terminal portion of Mtb32a. This was accomplished by using sequence-specific oligonucleotides containing unique restriction sites (EcoRI and EcoRV) and devoid of the stop codons at the C terminal ends (in the case of the C terminal fragment of Mtb32a and Mtb39a) for polymerase chain reaction (PCR) of genomic DNA from the *M. tuberculosis* strain H37Rv. Using this vector as template, a mutation of Ser706 to Ala was performed by site-directed mutagenesis. The proper orientation of inserts as well as the mutation Ser706Ala was verified by DNA sequencing.

In order to obtain the vector coding for M72, which just has 2 His residues at the N terminus, four H is were deleted making use of a commercial site-directed mutagenesis system. After sequence verification, the M72 coding sequence was excised from the plasmid by enzymatic reaction, gel purified and ligated into a pET vector. The recombinant plasmid was then sequence verified. This plasmid codes for M72 under the control of a T7 promoter. Expression of T7 RNA polymerase is driven from a genomic integrant in the expression host and is induced using a lac operon-based system (lacl) and an IPTG chemical induction signal. The expression plasmid is provided with kanamycin resistance.

The plasmid coding for the M72 fusion protein under the control of a T7 promoter was transformed into the HMS174 (DE3) strain of *E. coli*, using an electroporation method. The coding sequence of the M72 insert and the flanking regions were sequenced on both strands and were found to be identical to the sequence determined from the original plasmid construct.

Fermentation

A vial of pelleted working seed was thawed at room temperature. A pre-dilution was prepared by mixing the working seed with 4.9 ml of pre-culture medium. 1 ml of the pre-dilution was used to inoculate the liquid pre-culture which consists of 400 ml of pre-culture medium supplemented with 50 mg/l kanamycin sulfate and 10 g/l glucose.

| Pre-culture medium composition | | |
|---|---|---|
| Ingredient | Concentration | |
| $KH_2PO_4$ | 14.83 g/l | |
| $K_2HPO_4$ | 1.65 g/l | |
| $(NH_4)_2SO_4$ | 5.82 g/l | |
| Yeast extract | 6.21 g/l | |
| Glycerol 87% (w/w) | 14.54 ml/l | |
| Metal and salt solution[1]: | 9.7 ml/l | |
| $FeCl_36H_2O$ | | 3.3 g/l |
| $MgSO_47H_2O$ | | 58 g/l |
| Micro element solution[2]: | | 116 ml/l |
| $ZnSO_47H_2O$ | | 7.65 g/l |
| $MnSO_4H_2O$ | | 5.28 g/l |
| $CuSO_45H_2O$ | | 1.1 g/l |
| $CoCl_26H_2O$ | | 1.1 g/l |
| $H_3BO_3$ | | 0.3 g/l |
| $Na_2MoO_42H_2O$ | | 2.64 g/l |
| HCl 4N | | 6.2 ml/l |
| Biotine and $CaCl_2$ solution[2]: | 0.97 ml/l | |
| Biotine | | 0.05 g/l |
| $CaCl_22H_2O$ | | 61.7 g/l | pH of the medium is adjusted to 6.5 with NaOH (25%) solution
The medium is filtered through 0.22 um
[1]pH adjusted to 1.50 with HCl (37%) solution; the solution is filtered through 0.22 um
[2]The solution is filtered through 0.22 um The pre-culture was incubated in a 2 liter shake flask at 30° C. under agitation (200 RPM) until the $OD_{650nm}$ reached a value between 2 and 4 (approximate incubation time: 16 hours). At that stage, a 72 liter (total volume) fermenter containing 45 liters of culture medium supplemented with 34 mg/l kanamycin sulfate was inoculated with 52 ml liquid pre-culture.

| Culture medium composition | | |
|---|---|---|
| Ingredient | Concentration | |
| $MgSO_47H_2O$ | 0.63 g/l | |
| $FeCl_36H_2O$ | 0.056 g/l | |
| Micro element solution[1]: | 1.91 ml/l | |
| $ZnSO_47H_2O$ | | 7.65 g/l |
| $MnSO_4H_2O$ | | 5.28 g/l |
| $CuSO_45H_2O$ | | 1.1 g/l |
| $CoCl_26H_2O$ | | 1.1 g/l |
| $H_3BO_3$ | | 0.3 g/l |
| $Na_2MoO_42H_2O$ | | 2.64 g/l |
| HCl 4N | | 6.2 ml/l |
| HCl 37% | 0.40 mL/L | |
| Yeast extract | 35 g/L | |
| $(NH_4)_2SO_4$ | 2.10 g/l | |
| $KH_2PO_4$ | 18.70 g/l | |
| Sodium glutamate | 2.5 g/l | |
| Glycerol 87% | 0.276 ml/l | |
| Glucose | 20 g/l | |
| Biotine solution[2]: | 0.22 ml/l | |
| Biotine | | 1 g/l |
| $CaCl_22H_2O$ | 0.21 g/l | |

The solution is filtered through 0.22 um
[1]The solution is filtered through 0.22 um
[2]pH adjusted to 11.0 with NaOH (25%) solution; the solution is filtered through 0.22 um During the growth phase, pH was maintained at 6.8±0.2 by periodic addition of 25% (v/v) $NH_4OH$ and 25% (v/v) $H_3PO_4$. After incubation for 16 hours at 30° C., fed-batch was started with feed medium.

| Feed medium composition | | |
|---|---|---|
| Ingredient | Concentration | |
| $MgSO_47H_2O$ | 1.98 g/l | |
| $FeCl_36H_2O$ | 0.178 g/l | |
| Micro element solution[1]: | 6.02 ml/l | |
| $ZnSO_47H_2O$ | | 7.65 g/l |
| $MnSO_4H_2O$ | | 5.28 g/l |
| $CuSO_45H_2O$ | | 1.1 g/l |
| $CoCl_26H_2O$ | | 1.1 g/l |
| $H_3BO_3$ | | 0.3 g/l |
| $Na_2MoO_42H_2O$ | | 2.64 g/l |
| HCl 4N | | 6.2 ml/l |
| HCl 37% | 1.24 ml/l | |
| Sodium glutamate | 5 g/l | |
| Yeast extract | 40 g/l | |
| Glycerol 87% | 590 ml/l | |
| Biotine solution[2]: | 2 ml/l | |
| Biotine | | 1 g/l |
| $CaCl_22H_2O$ | 0.66 g/l | |

The solution is filtered through 0.22 um
[1]The solution is filtered through 0.22 um
[2]pH adjusted to 11.0 with NaOH (25%) solution; the solution is filtered through 0.22 um The temperature was maintained at 30° C. for a further 2 hours, then raised to 37° C. until the end of fermentation. The air flow was constantly set to 75 l/min and the dissolved oxygen kept at 17% saturation by feedback control of the agitation and pressure. Small quantities of antifoam solution were added on demand automatically. By the time the $OD_{650nm}$ reached a value of 50 (±5), 1 mM Isopropyl-beta-D-thiogalactopyranoside (IPTG) was added in order to induce the expression of M72. Fermentation ended after 5 hours from the time point induction was started. The cell culture was cooled down to 15° C. under slight agitation and centrifuged (at 4° C.) to obtain cell pellets which were thereafter stored at −20° C. in aliquots.

Isolation of Inclusion Bodies

The cell pellets collected from the harvest were thawed at room temperature and disrupted in lysis buffer (10 mM Tris, 50 mM NaCl, pH 8.0) with a high pressure homogenizer. Thereafter the cell lysate wa centrifuged and the resulting cell pellets (or inclusion bodies, IBs) were washed with wash buffer containing urea, Tris and NaCl. The IBs were solubilised with solubilisation buffer containing 8 M urea and filtered through a 0.2 um membrane. This filtered solution was first purified by anion exchange chromatography using a Q Sepharose Fast Flow (QSFF) column. The elution of M72 takes place with a 6 M urea, 20 mM bis-Tris propane, 90 mM NaCl, pH 7.0 solution.

M72 collected was further purified by Hydroxyapatite chromatography (HA), from which it is eluted with a 6 M urea, 20 mM bis-Tris propane, 250 mM NaCl, pH 7.0 solution. The collected fraction was concentrated with a 30 kDa membrane cassette and diafiltered against 20 mM Tris, pH 7.5. M72 was then sterilised through a 0.22 um filter. The purified bulk was then aliquoted and stored at −70° C.

Example 10

Investigation of "Salting Out" in Compositions Comprising M72 with Different Salt Concentrations at pH 6.1, 7.5 and 8.5

The impact of sodium chloride concentration and pH on M72 antigen stability, as assessed by size and antigenicity, was investigated.

Method

Purified bulk antigen (M72 with two N-terminal His residues, SEQ ID No: 7, as prepared in Example 9) was diluted to a concentration of 100 ug/ml in three different buffers (10 mM phosphate buffer at pH 6.1, mM Tris buffer at pH 7.5 and 20 mM Tris buffer at pH 8.5) containing final sodium chloride concentrations of 0, 50, 150, 300 and 450 mM.

Samples were analysed immediately (T0), stored overnight at 4° C. before analysis (T0 O/N) or stored at 25° C. for 24 hours before analysis (T24h25° C.).

DLS was performed using a Malvern Zetasizer Nano ZS from Malvern Instruments (UK). The instrument was operated using a laser wavelength of 633 nm and power of 4 mW. Scattered light was detected at 173° at a temperature of 22° C. The Z-average diameter (Zav) and polydispersity index (p1) are calculated by the instrument software.

Nephlometry was performed using a Nepheloskan® Ascent, available from Thermo Fischer Scientific. Analysis was performed in UV transparent Costar® micro-plates available from Corning Inc (USA).

Antigenicity was quantified by a sandwich ELISA in which the antigen is captured by a M72-specific rabbit polyclonal antibody and subsequently revealed by a M72 (Mtb39)-specific mouse monoclonal antibody. All measured values are presented relative to the expected antigenicity based on the purified bulk protein used to prepare the tested formulations.

Results

Figure 5:
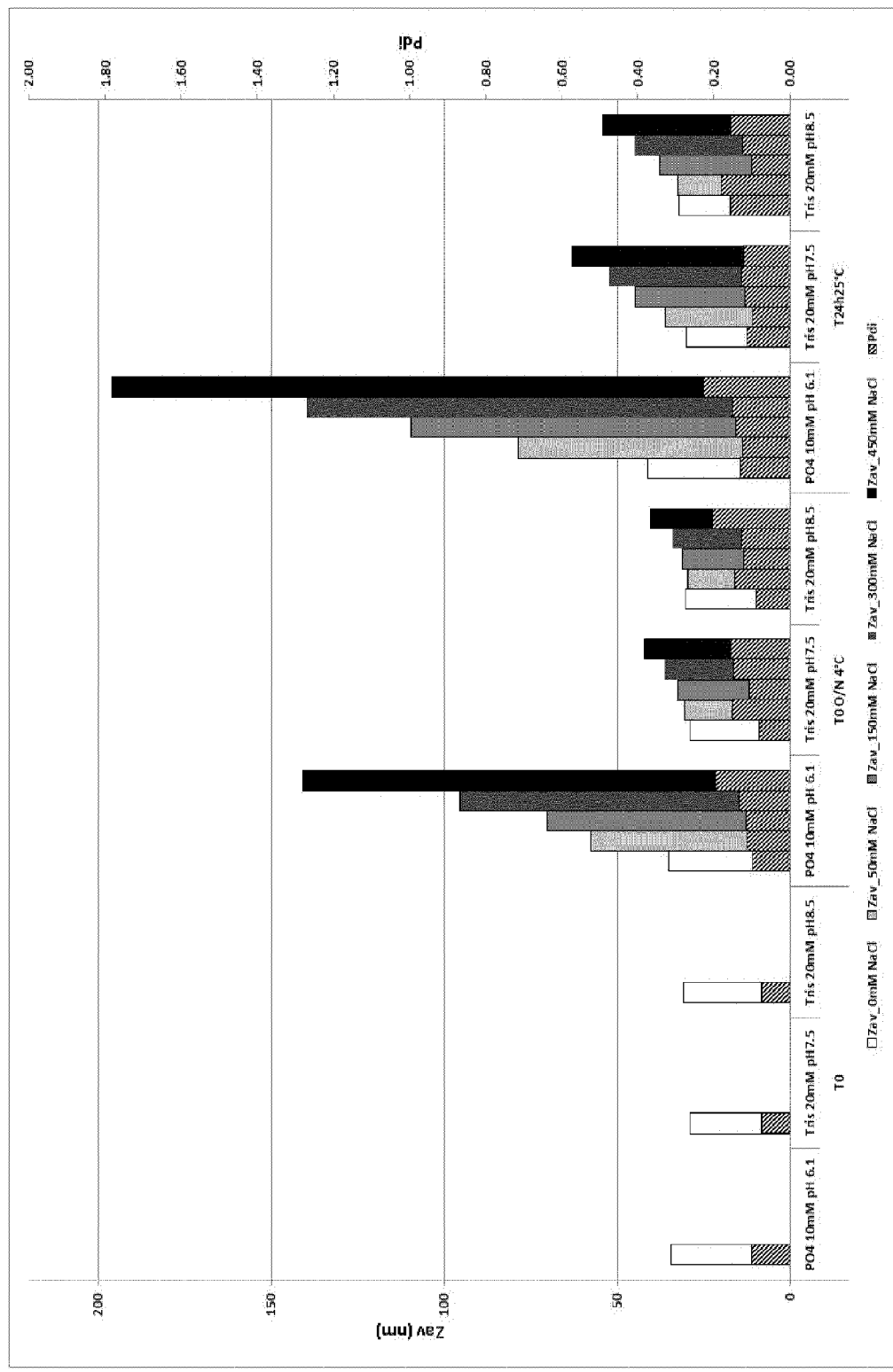
Figure 6:
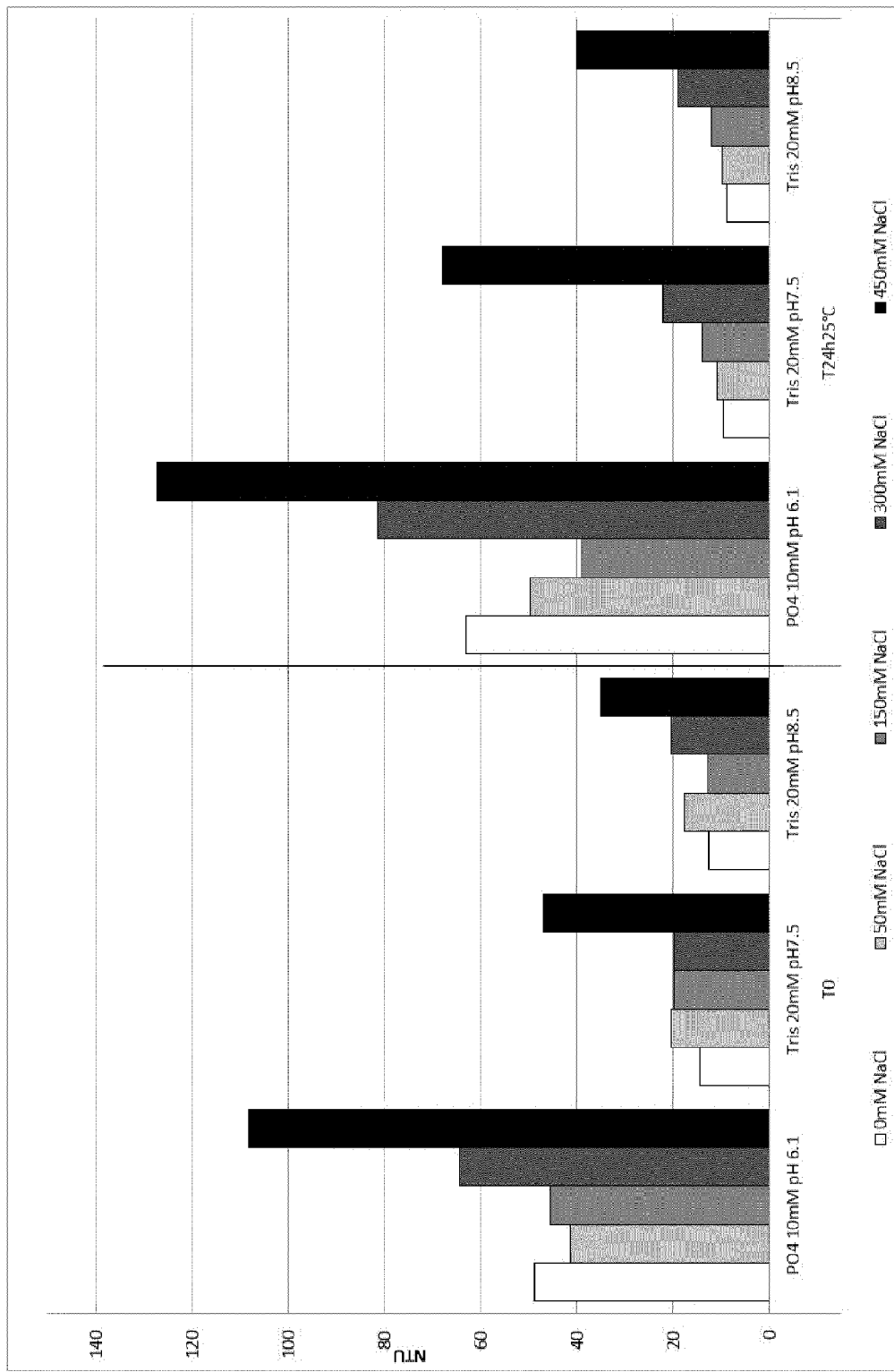
Figure 7:
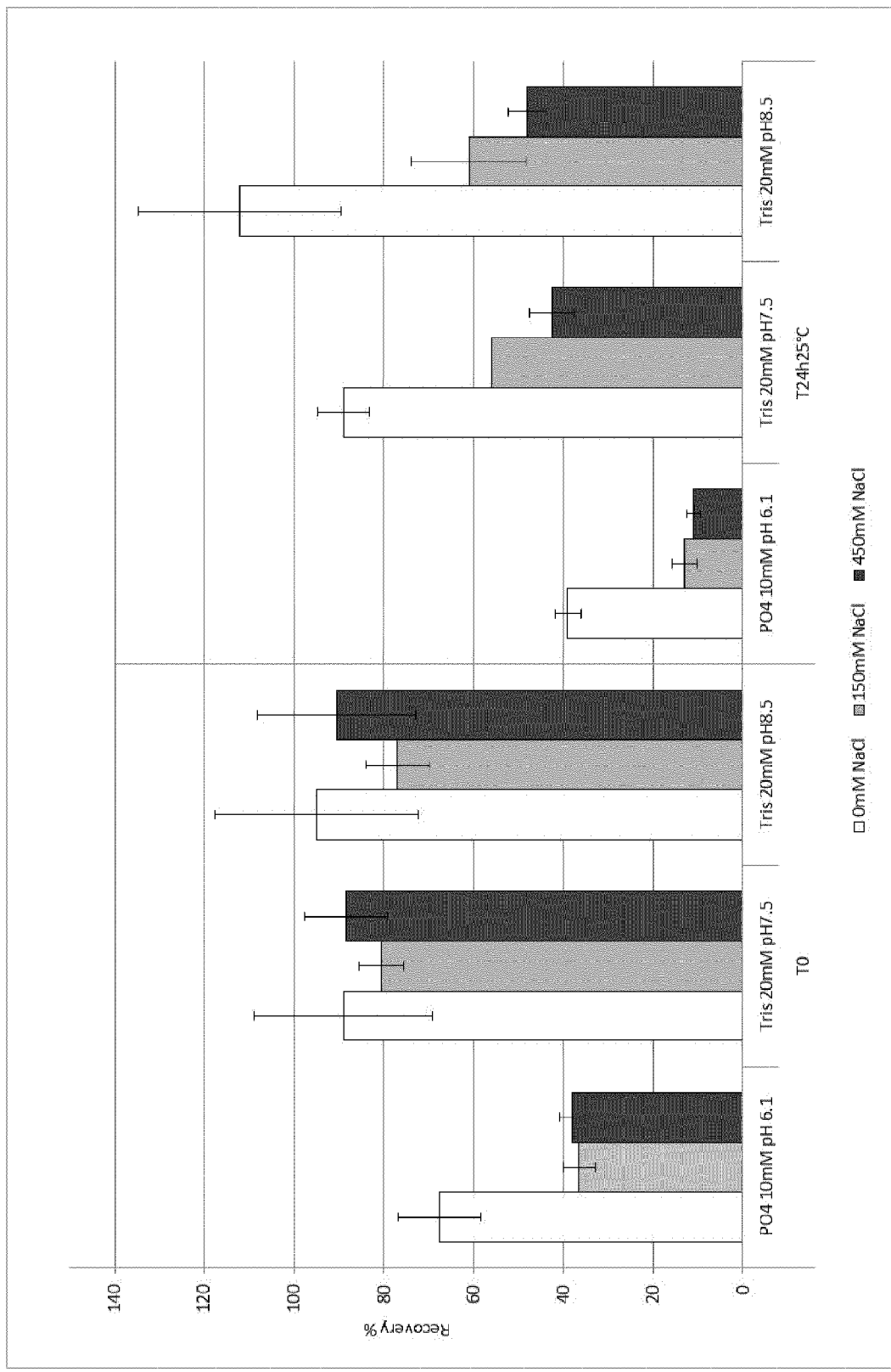
Figure 8A:
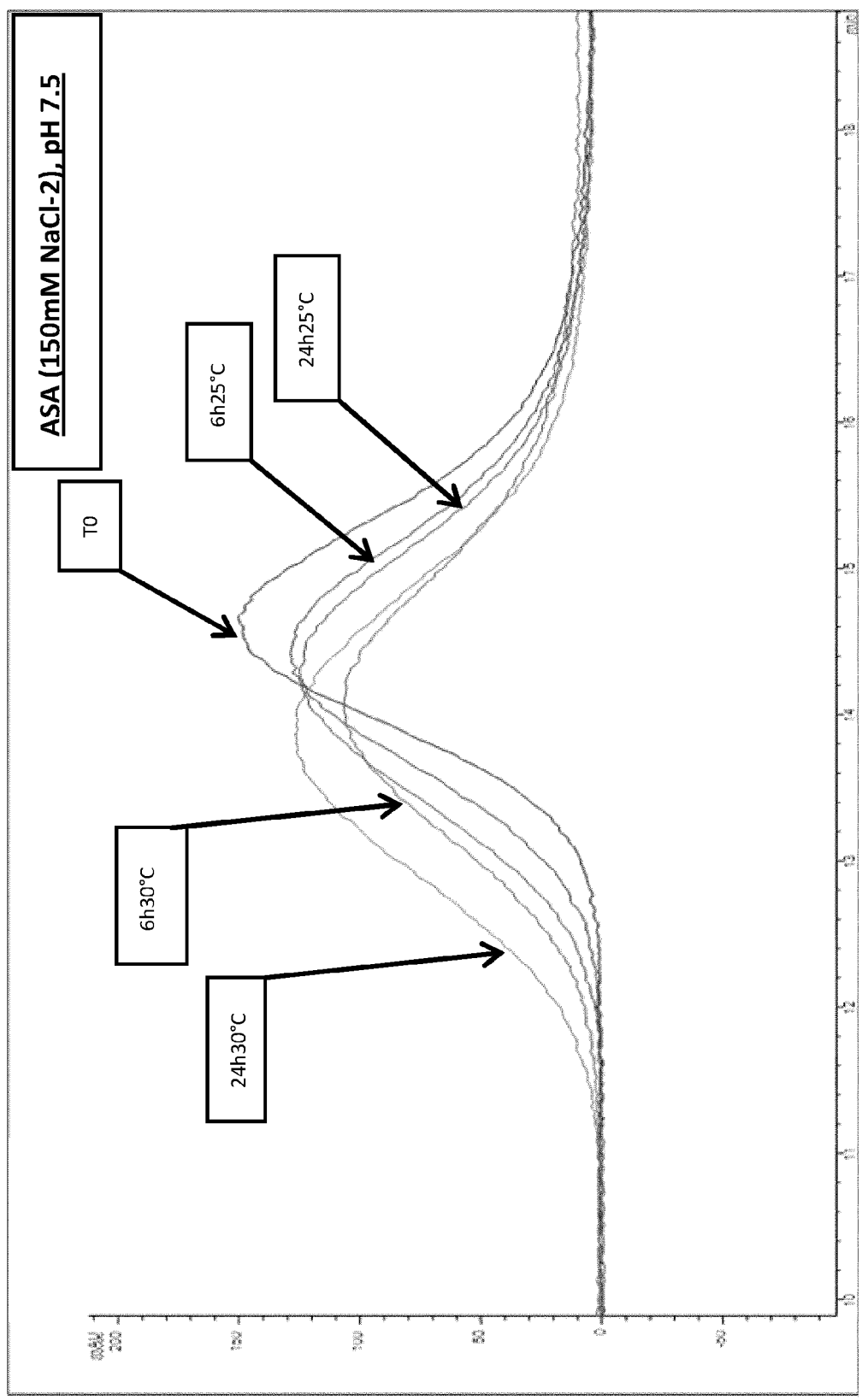
Figure 8B:
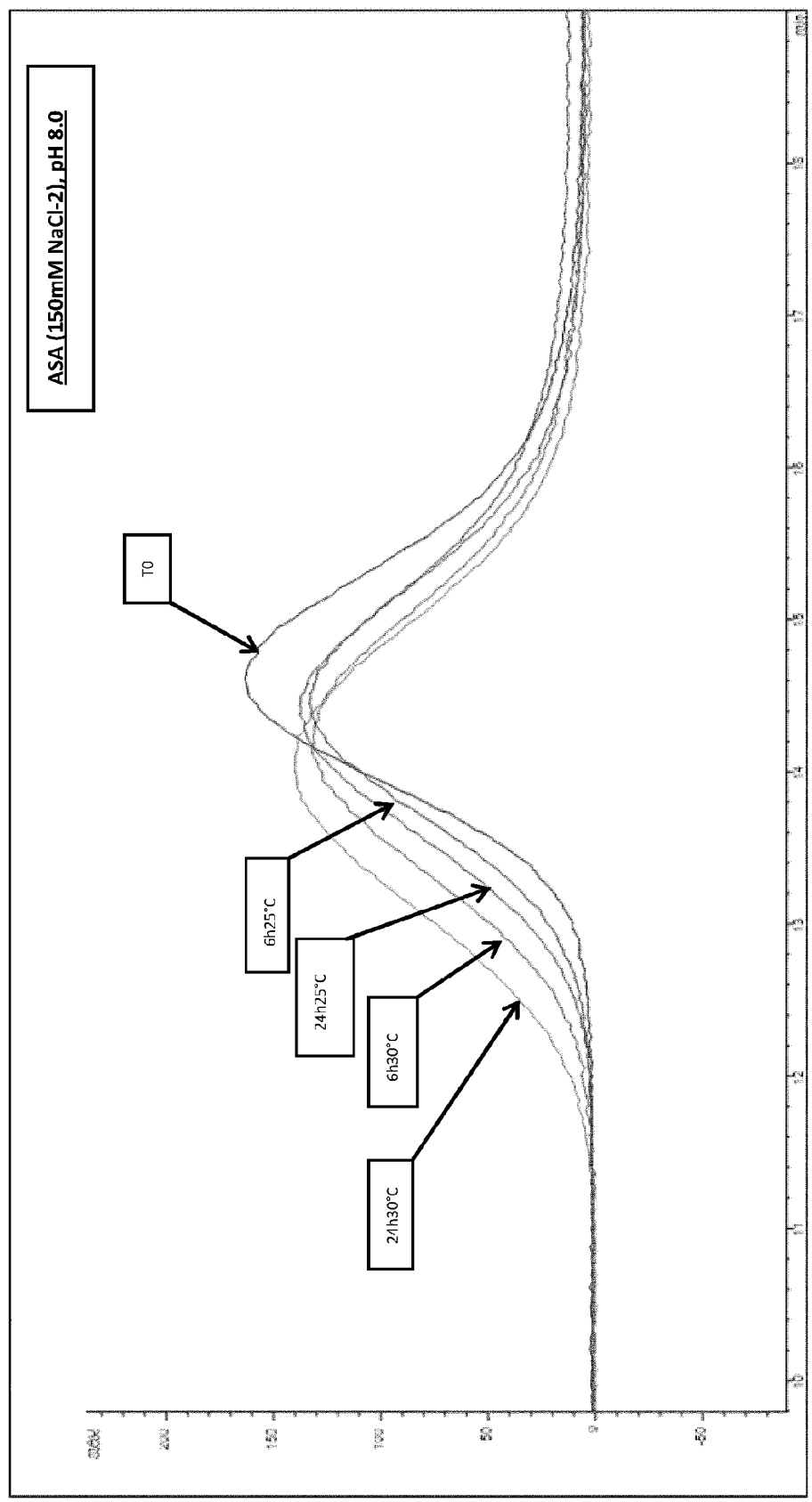
Figure 8C:
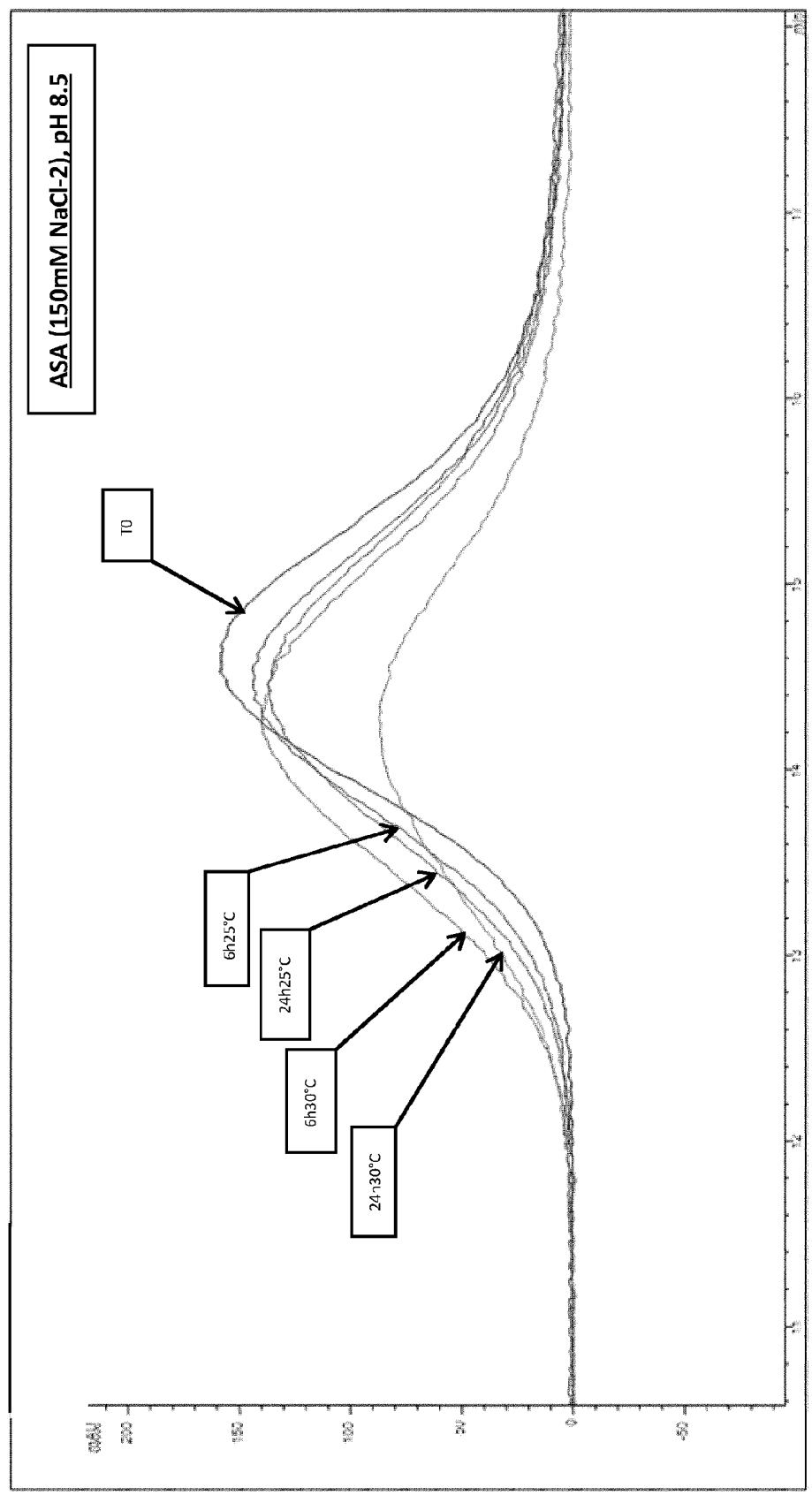
Figure 8D:
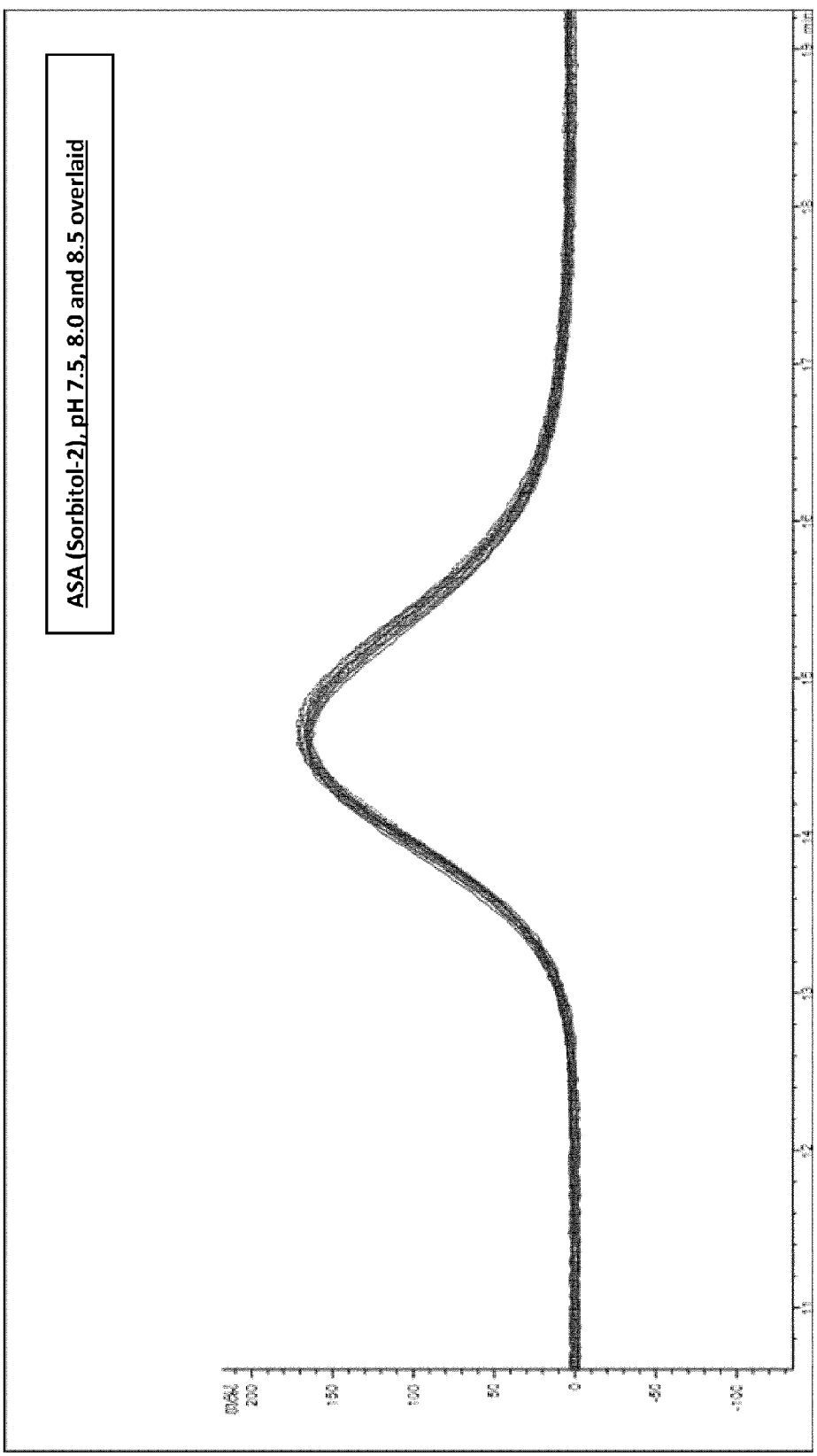
Figure 9:
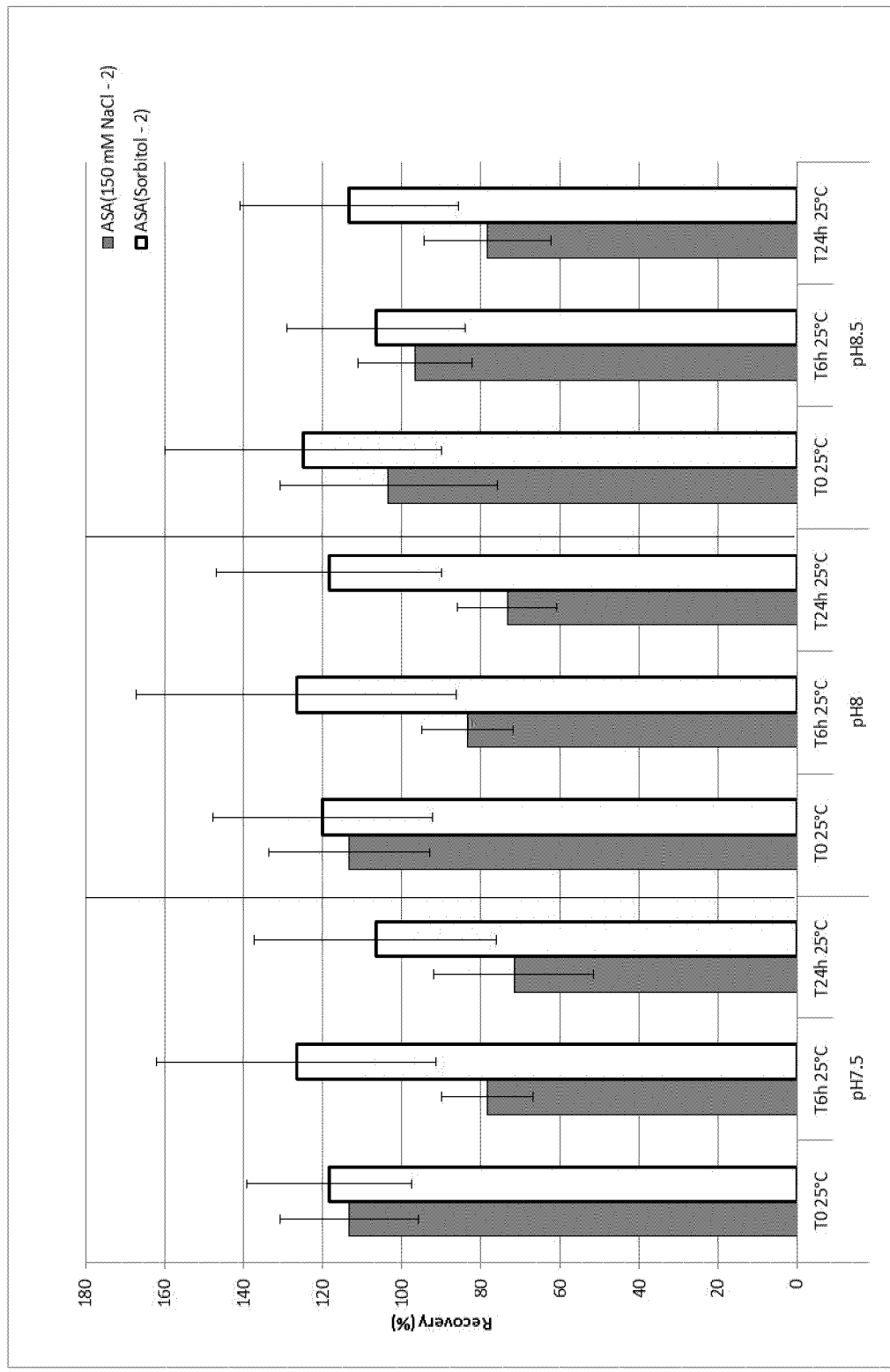

The findings of this experiment are presented in FIGS. 5 to 7.

The results demonstrate for the first time that the stability of solutions containing an Rv1196 related antigen, specifically M72, is sensitive to both pH and sodium chloride concentration. The impact of sodium chloride on antigen size and antigenicity is all the more notable as the pH is lower.

Antigen size and antigenicity are not stable at pH 6.1 even in the absence of sodium chloride. The addition of 50 mM sodium chloride at pH 6.1 led to a size increase from 35 nm (0 mM sodium chloride at T0) up to 58 nm (T0) or 79 nm after 24 hours at 25° C.

Antigen size and antigenicity are relatively stable over 24 hours at 25° C. at pH 7.5 or 8.5, particularly in the absence of sodium chloride or at a sodium chloride concentration of 50 mM. Nevertheless, increasing the concentration of sodium chloride to 150 mM or greater results in a clear increase in antigen size and reduction in antigenicity.

Consequently, the benefits of the present invention extend to sequences containing Rv1196 related antigens and not just to the Rv1196 antigen sequence itself.

Example 11

Prevention of "Salting Out" in Compositions Comprising M72, Immunostimulants and Using Sorbitol as a Tonicity Agent In order to compare the stability of immunogenic compositions containing 150 mM NaCl with compositions using sorbitol as a tonicity agent, a number of samples were monitored using SEC-HPLC and ELISA.

Method

Three different lyophilisation cakes were prepared, such that when combined with the appropriate adjuvant formulations from Examples 5 and 7 the desired pH would be obtained:

(a) M72 with Two N-Terminal his Residues—Target pH 8.5 in Reconstituted Vaccine
  15.75% (w/v) sucrose solution (prepared in water for injection) was added to water for injection to reach a sucrose concentration of 6.3%. 3% (w/v) Tween80 solution (prepared in water for injection) was then added to reach a concentration of 0.025%. Tris-HCl buffer 1 M pH 8.8 was then added to reach a 50 mM Tris buffer concentration. The mixture was magnetically stirred for 5 minutes at room temperature. Purified bulk antigen (M72 with two N-terminal His residues, SEQ ID No: 7, as prepared in Example 9) was then added to reach a protein concentration of 25 ug/ml. The mixture was magnetically stirred for 10 minutes at room temperature. The pH was checked and found to be 8.8.
  0.5 ml of the mixture obtained was filled in 3 ml glass vials then freeze dried.

(b) M72 with Two N-Terminal his Residues—Target pH 8.0 in Reconstituted Vaccine
  15.75% (w/v) sucrose solution (prepared in water for injection) was added to water for injection to reach a sucrose concentration of 6.3%. 3% (w/v) Tween80 solution (prepared in water for injection) was then added to reach a concentration of 0.025%. Tris-HCl buffer 1 M pH 8.8 was then added to reach a 20 mM Tris buffer concentration. The mixture was magnetically stirred for 5 minutes at room temperature. Purified bulk antigen (M72 with two N-terminal His residues, SEQ ID No: 7, as prepared in Example 9) was then added to reach a protein concentration of 25 ug/ml. The mixture was magnetically stirred for 10 minutes at room temperature. The pH was checked and found to be 8.8.
  0.5 ml of the mixture obtained was filled in 3 ml glass vials then freeze dried.

(c) M72 with Two N-Terminal his Residues—Target pH 7.5 in Reconstituted Vaccine
  15.75% (w/v) sucrose solution (prepared in water for injection) was added to water for injection to reach a sucrose concentration of 6.3%. 3% (w/v) Tween80 solution (prepared in water for injection) was then added to reach a concentration of 0.025%. Tris-HCl buffer 1 M pH 8.8 was then added to reach a 12.5 mM Tris buffer concentration. The mixture was magnetically stirred for 5 minutes at room temperature. Purified bulk antigen (M72 with two N-terminal His residues, SEQ ID No: 7, as prepared in Example 9) was then added to reach a protein concentration of 25 ug/ml. The mixture was magnetically stirred for 10 minutes at room temperature. The pH was checked and found to be 8.8.
  0.5 ml of the mixture obtained was filled in 3 ml glass vials then freeze dried.

The lyophilisation cakes described above were reconstituted with 625 ul of the adjuvant solutions prepared in Examples 5 and 7. Upon reconstitution with adjuvant solution, the following immunogenic compositions were obtained:

(i) M72 with Two N-Terminal his Residues—ASA (150 mM NaCl-2) pH 8.5
  10 ug antigen (20 ug/ml)
  5% w/v sucrose
  40 mM Tris
  0.02% w/v Tween80
  500 ug DOPC
  125 ug cholesterol
  25 ug 3D-MPL
  25 ug QS21
  150 mM NaCl 10 mM phosphate
pH 8.5
(ii) M72 with Two N-Terminal his Residues—ASA (150 mM NaCl-2) pH 8.0
10 ug antigen (20 ug/ml)
5% w/v sucrose
16 mM Tris
0.02% w/v Tween80
500 ug DOPC
125 ug cholesterol
25 ug 3D-MPL
25 ug QS21
150 mM NaCl
10 mM phosphate
pH 8.0
(iii) M72 with Two N-Terminal his Residues—ASA (150 mM NaCl-2) pH 7.5
10 ug antigen (20 ug/ml)
5% w/v sucrose
12.5 mM Tris
0.02% w/v Tween80
500 ug DOPC
125 ug cholesterol
25 ug 3D-MPL
25 ug QS21
150 mM NaCl
10 mM phosphate
pH 7.5
(iv) M72 with Two N-Terminal his Residues—ASA (Sorbitol-2) pH 8.5
10 ug antigen (20 ug/ml)
5% w/v sucrose
40 mM Tris
0.02% w/v Tween80
500 ug DOPC
125 ug cholesterol
25 ug 3D-MPL
25 ug QS21
5 mM NaCl
4.7% w/v sorbitol
10 mM phosphate
pH 8.5
(v) M72 with Two N-Terminal his Residues—ASA (Sorbitol-2) pH 8.0
10 ug antigen (20 ug/ml)
5% w/v sucrose
16 mM Tris
0.02% w/v Tween80
500 ug DOPC
125 ug cholesterol
25 ug 3D-MPL
25 ug QS21
5 mM NaCl
4.7% w/v sorbitol
10 mM phosphate
pH 8.0
(vi) M72 with Two N-Terminal his Residues—ASA (Sorbitol-2) pH 7.5
10 ug antigen (20 ug/ml)
5% w/v sucrose
12.5 mM Tris
0.02% w/v Tween80
500 ug DOPC
125 ug cholesterol
25 ug 3D-MPL
25 ug QS21
5 mM NaCl
4.7% w/v sorbitol
10 mM phosphate
pH 7.5

Sample Analysis

The reconstituted immunogenic compositions described above were characterised after storage at 25° C. or 30° C. (T0, T6 h and T24 h).

SEC-HPLC analysis was performed by injection on a TOSOH TSK-Gel5000Pwxl (ID 7.8 mm×30 cm) equilibrated in 20 mM Tris buffer pH 8.5, detection by UV at 210 nm and flow rate 0.5 ml/min.

Antigenicity was quantified by a sandwich ELISA in which the antigen is captured by a M72-specific rabbit polyclonal antibody and subsequently revealed by a M72 (Mtb39)-specific mouse monoclonal antibody. All measured values are presented relative to the expected antigenicity based on the purified bulk protein used to prepare the tested formulations.

Results

The results are shown in FIGS. 8a-8d and 9.

SEC-HPLC profiles are stable after reconstitution in low salt compositions using sorbitol as a tonicity agent at each pH (i.e. pH 7.5, 8.0 and 8.5). This may be contrasted with the SEC-HPLC profiles for immunogenic compositions containing 150 mM NaCl, which show clear changes between the initial profile obtained and those following storage at 25° C. or 30° C. This evolution becomes more intense when the pH of the 150 mM NaCl composition is lowered.

The same conclusions can be drawn in terms of antigenicity, with recoveries remaining largely stable after reconstitution in low salt compositions using sorbitol as a tonicity agent at each pH (i.e. pH 7.5, 8.0 and 8.5) up to 24 h at 30° C.

Example 12

Conductivity Determination for Immunogenic Compositions of the Invention

The conductivity of a range of immunogenic compositions according to the present invention was measured and compared to the conductivity of control sodium chloride solutions and with an immunogenic composition containing a conventional quantity of sodium chloride.

Method

A range of standards having sodium chloride concentrations of 0, 75, 100, 150, 250 and 300 mM were prepared from a stock solution of 1500 mM sodium chloride by dilution in water for injection.

Immunogenic compositions were prepared using M72 with two N-terminal His residues according to the procedures provided in Example 9. To investigate the contribution from the antigen itself and any residual materials in the purified bulk, placebo lyophilisation cakes were also prepared by excluding the antigen component.

Using a Malvern Zetasizer Nano and 1.5 ml of each sample in folded capillary cells, a voltage of 30 to 150 V (determined automatically by the instrument) was applied and the conductivity determined.

Results

| Conductivity of sodium chloride standard solutions | |
|---|---|
| Sodium chloride concentration mM | Conductivity mS/cm |
| 0 | 0.0 |
| 75 | 8.2 |
| 100 | 10.7 |
| 150 | 15.6 |
| 250 | 23.9 |
| 300 | 30.0 |

Figure 10:
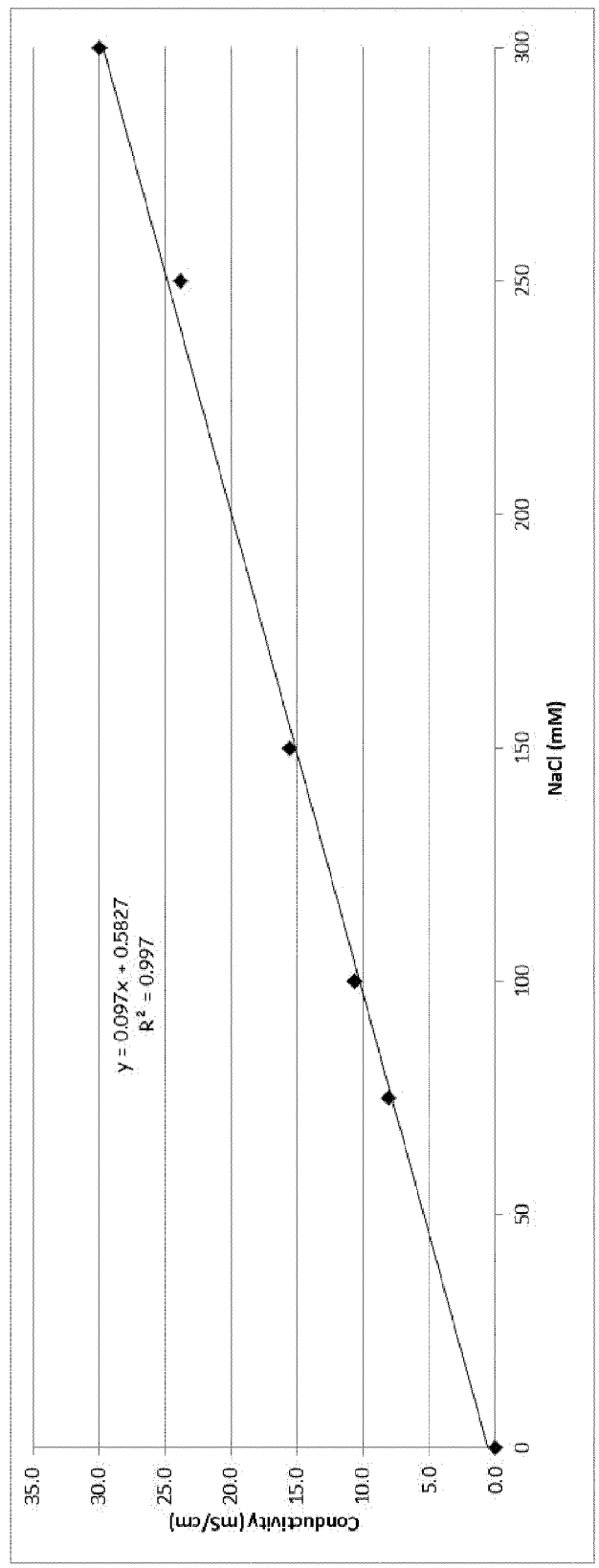

A standard curve, based on this data, is provided in FIG. 10.

| Conductivity of test solutions | | | |
|---|---|---|---|
| Description | Sodium chloride concentration mM | Conductivity mS/cm | Equivalent sodium chloride concentration mM |
| ASA(sorbitol-2) | 5 | 1.46 | 9 |
| Placebo pH 8.0/ASA(sorbitol-2) | 5 | 1.95 | 14 |
| M72 pH 8.0/ASA(sorbitol-2) | 5 | 1.96 | 14 |
| Placebo pH 8.5/ASA(sorbitol-2) | 5 | 2.36 | 18 |
| M72 pH 8.5/ASA(sorbitol-2) | 5 | 2.28 | 17 |
| ASA(150 mM NaCl-2) | 150 | 16 | 159 |
| Placebo pH 8.5/ASA(150 mM NaCl-2) | 150 | 14.8 | 147 |
| M72 pH 8.5/ASA(150 mM NaCl-2) | 150 | 15.3 | 152 |

As can be seen from the data above, the conductivity of solutions which utilise 150 mM NaCl is significantly greater than that of solutions which make minimal use of NaCl.

The impact of the antigen and any components in the purified bulk is minimal, as placebo preparations have comparable conductivity to their Rv1196 related antigen containing counterparts.

Example 13

Immunogenicity Testing of Immunogenic Compositions of the Invention

The aim of the this Example was to determine whether or not formulation changes to reduce the quantity of salt in immunogenic compositions of the invention, with a view to improving protein stability, had an impact on in vivo immunogenicity.

Method

Four immunogenic compositions were evaluated:
1. M72 with two N-terminal His residues pH 8.5/ASA (150 mM NaCl-2)
2. M72 with two N-terminal His residues pH 8.5/ASA (Sorbitol-2)
3. M72 with two N-terminal His residues pH 8/ASA (Sorbitol-2)
4. M72 with two N-terminal His residues pH 7.5/ASA (Sorbitol-2)

The immunogenicity of these antigen containing compositions was evaluated in C57BL/6 mice. For each of the four compositions, 30 C57BL/6 mice were injected 3 times intramuscularly, on days 0, 14 and 28 with 1 ug of antigen in 50 ul of adjuvant solution (prepared by the procedure provided in Example 11). The elicited M72 specific T cell responses (both CD4 & CD8) were measured 6 days post last immunisation (6dPIII).

For the determination of M72-specific cellular responses, peripheral blood lymphocytes from 30 mice/group were collected and pooled (six pools of five mice/group). A red blood cells lysis was performed before plating the cells in vitro. The cells were restimulated in vitro with a pool of overlapping peptides (15-mer peptides with an 11 amino acid overlap, at 1 ug/ml/peptide) covering the M72 sequence (without the N-terminal His residues). Cells remaining in medium (no peptide stimulation) were used to determine the background responses. Two hours after the co-culture with the peptide pool, brefeldin A was added to the wells (to inhibit cytokine excretion) and the cells were stored overnight at 4° C. The cells were subsequently stained for the following markers: CD4, CD8, IL-2, IFN-gamma and TNF-alpha.

Results

Figure 11:
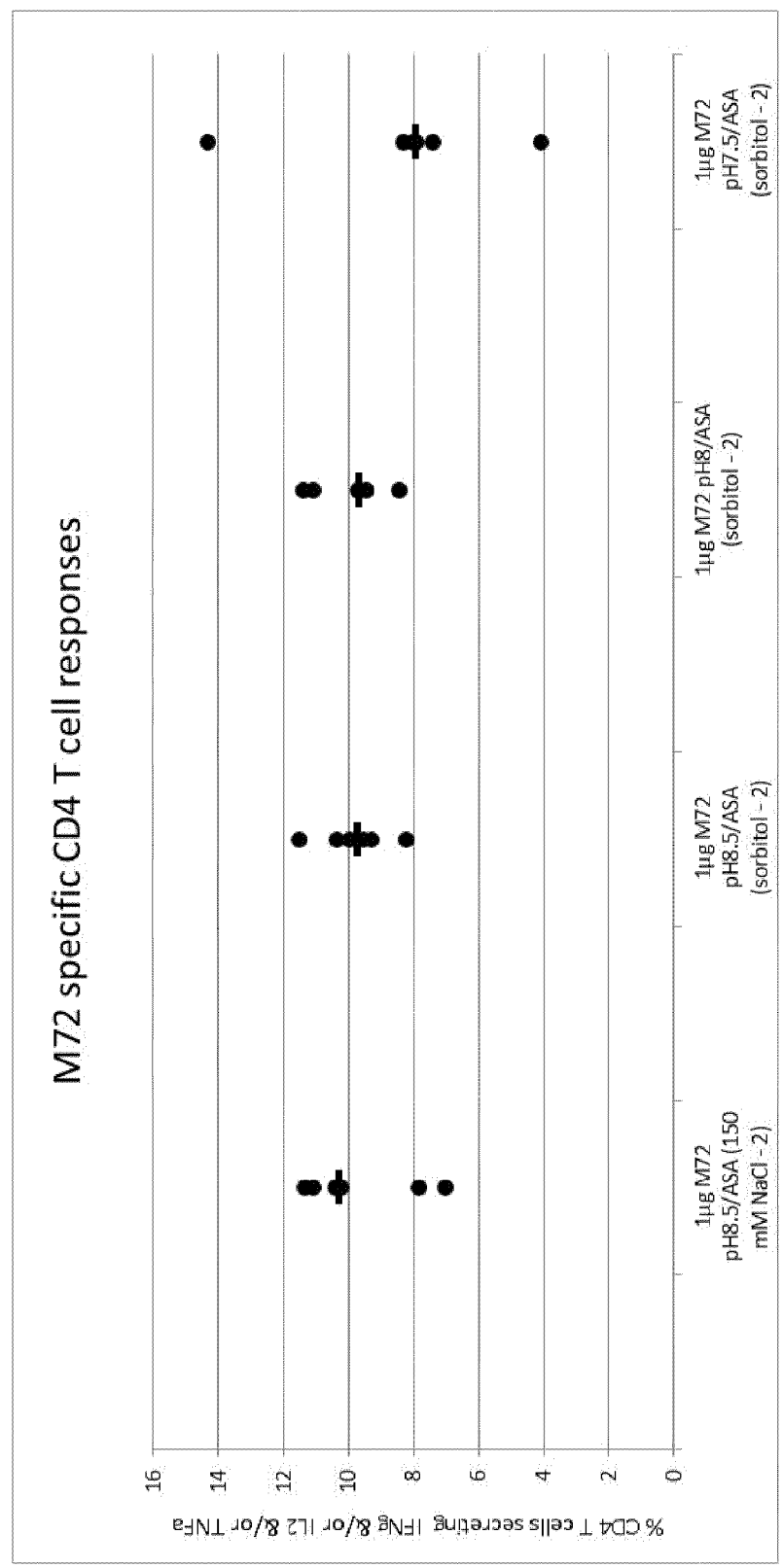
Figure 12:
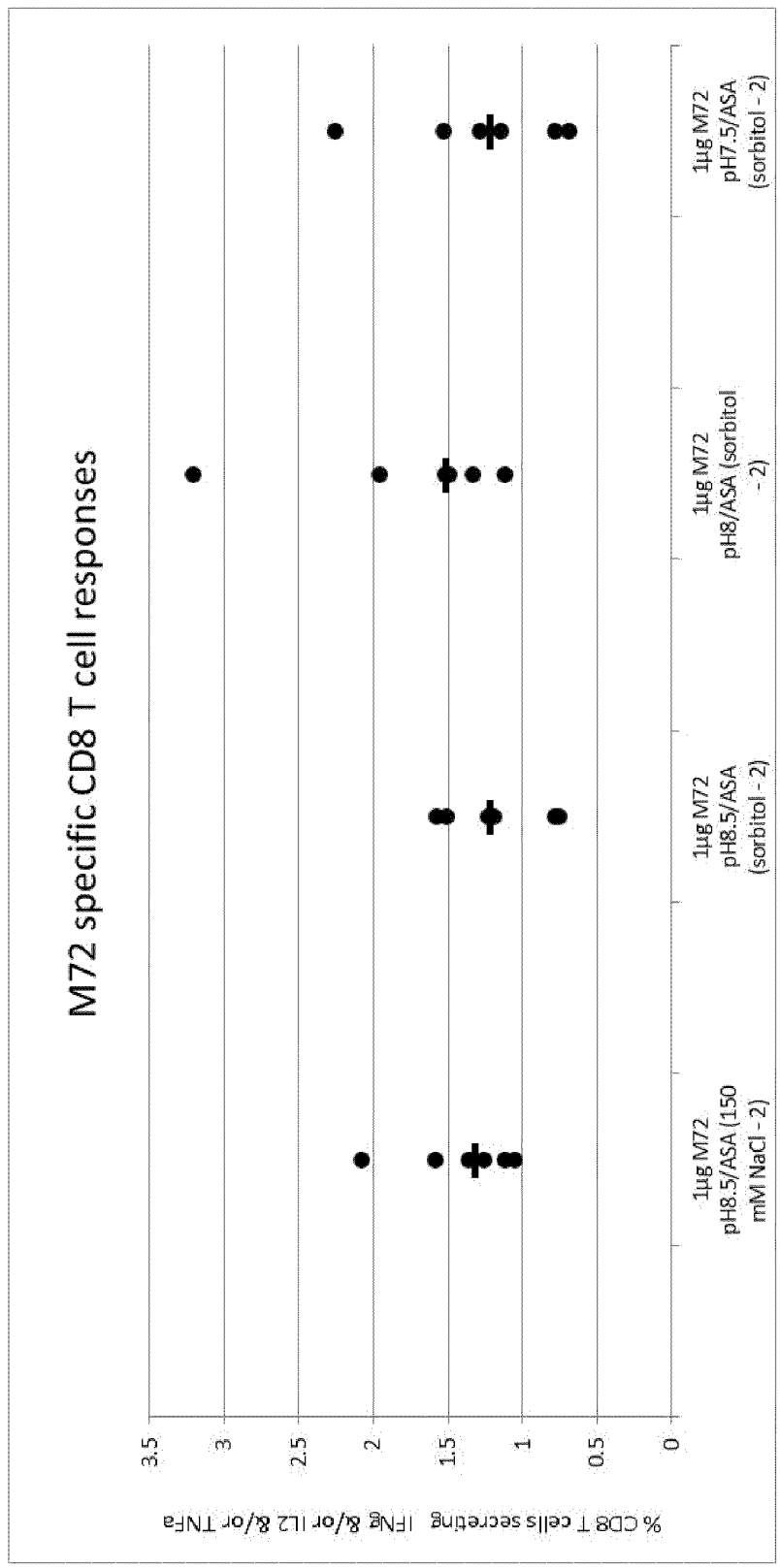
Figure 13:
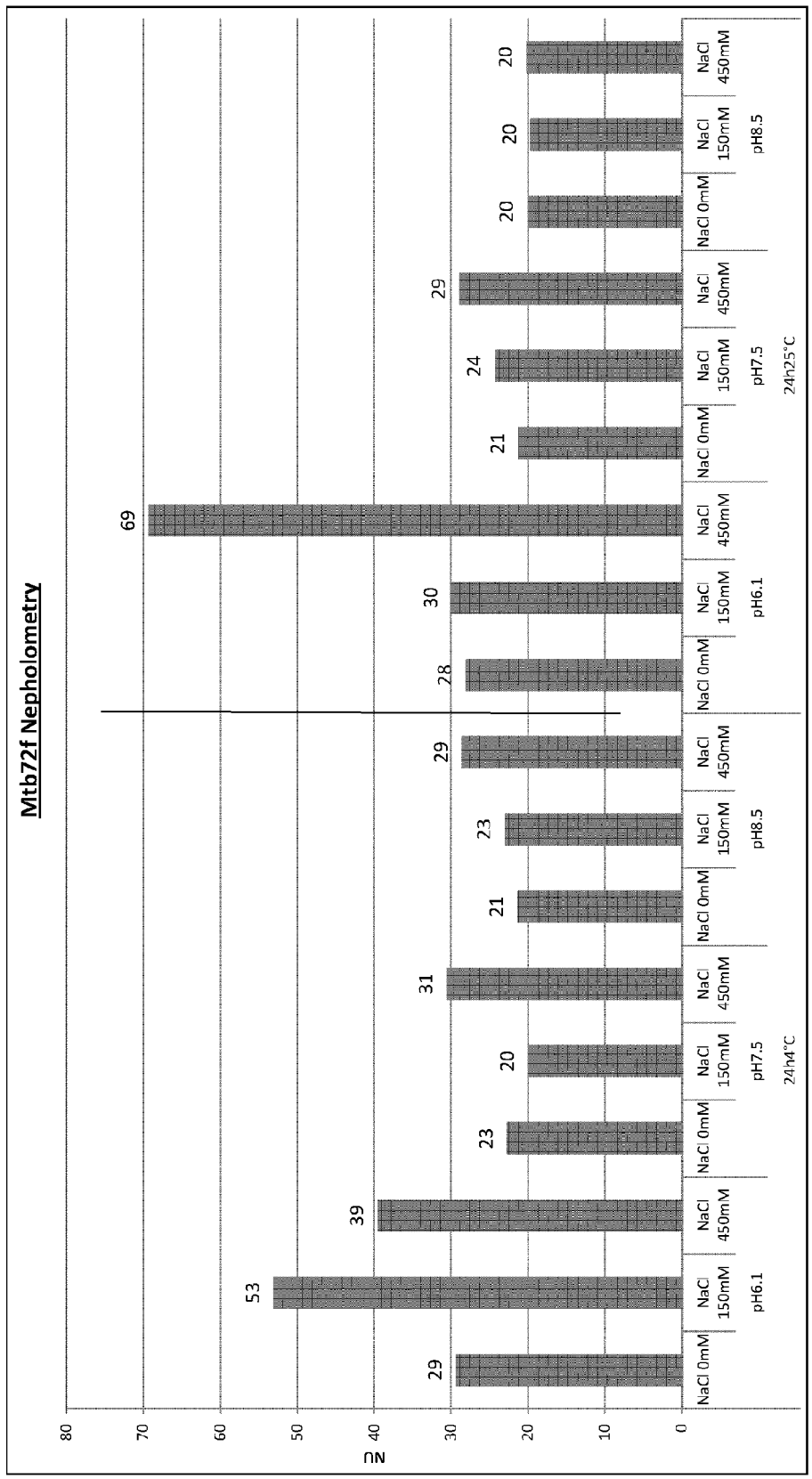
Figure 14:
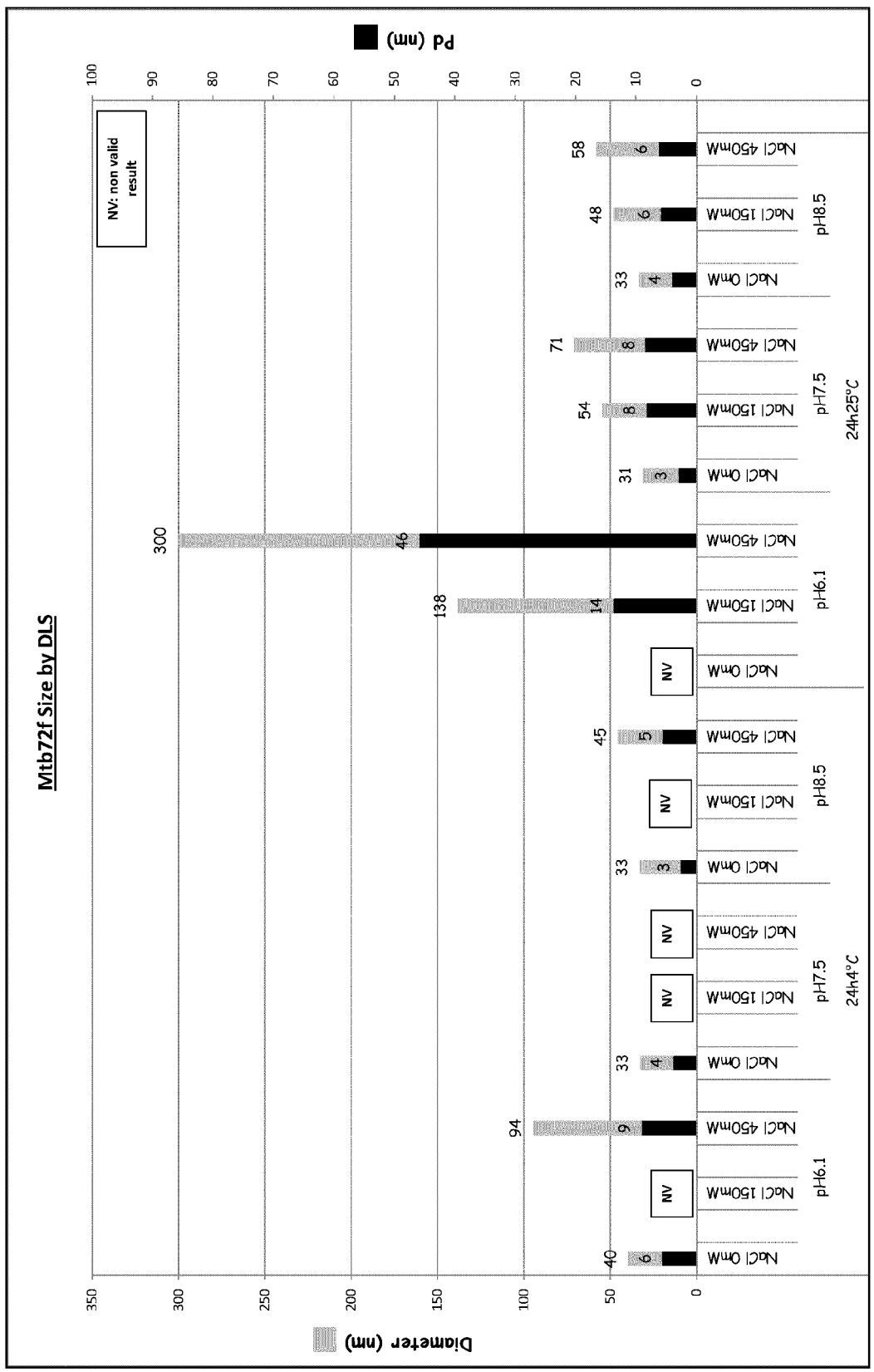

Each datapoint in FIGS. 11 and 12 represents the background subtracted M72-specific CD4 or CD8 T cell response, respectively, of a pool of peripheral blood lymphocytes from five mice six days after the third immunisation. The response is expressed as the percentage of CD4 T cells producing IFN-gamma and/or IL-2 and/or TNF-alpha in response to simulation with the M72 peptide pool. The bar represents the median of the responses for each group.

The results in FIGS. 11 and 12 show that comparable CD4 and CD8 T cell responses are induced following three immunisations with each of the test formulations. Consequently, it may be concluded that a reduction in the quantity of salts present in the immunogenic compositions of the present invention does not lead to a compromise in the induced T cell responses.

Example 14

Investigation of "Salting Out" in Compositions Comprising M72 with $CaCl_2$ or $MgSO_4$ at pH 6.1 and 8.0

To investigate impact of other salts on M72 antigen stability, solutions were prepared with a range of concentrations of $CaCl_2$ or $MgSO_4$ and at different pH levels. Visual inspection was used as a readout of stability.

Method

Purified bulk antigen (M72 with two N-terminal His residues, SEQ ID No: 7) was diluted to a concentration of 100 ug/ml in two different buffers (10 mM succinate buffer at pH 6.1 and 10 mM Tris buffer at pH 8.0) containing specified quantities of salts (0 mM; 150 mM or 300 mM NaCl; 40 mM, 80 mM or 160 mM $CaCl_2$; 87.5 mM, 175 mM or 430 mM $MgSO_4$).

Samples were analysed directly after preparation.

Using a Mettler Toledo conductivity meter and 6 ml of each sample in an unsiliconised glass vial, the conductivity was determined.

Results

| Group | Salt | Buffer | pH (theoretical) | Conductivity (mS/cm) (measured) | pH (measured) | Visual Observation |
|---|---|---|---|---|---|---|
| A | 0 mM | Succinate 10 mM | 6.1 | 1.1 | 6.3 | Clear |

-continued

| Group | Salt | Buffer | pH (theoretical) | Conductivity (mS/cm) (measured) | pH (measured) | Visual Observation |
|---|---|---|---|---|---|---|
| B | NaCl 150 mM | Succinate 10 mM | 6.1 | 13.4 | 6.1 | Clear |
| C | NaCl 300 mM | Succinate 10 mM | 6.1 | 20.0 | 6.1 | Clear |
| D | $CaCl_2$ 40 mM | Succinate 10 mM | 6.1 | 8.0 | 6.1 | Opalescent |
| E | $CaCl_2$ 80 mM | Succinate 10 mM | 6.1 | 11.2 | 5.8 | Opalescent + large particles |
| F | $CaCl_2$ 160 mM | Succinate 10 mM | 6.1 | 20.2 | 5.8 | Opalescent + large particles |
| G | $MgSO_4$ 87.5 mM | Succinate 10 mM | 6.1 | 7.7 | 6.1 | Opalescent |
| H | $MgSO_4$ 175 mM | Succinate 10 mM | 6.1 | 12.4 | 5.9 | Opalescent + very large particles |
| I | $MgSO_4$ 430 mM | Succinate 10 mM | 6.1 | 20.4 | 5.9 | Opalescent + very large particles |
| J | 0 mM | Tris 10 mM | 8.0 | 0.463 | 8.0 | Clear |
| K | NaCl 150 mM | Tris 10 mM | 8.0 | 12.13 | 8.0 | Clear |
| L | NaCl 300 mM | Tris 10 mM | 8.0 | 21.1 | 8.0 | Clear |
| M | $CaCl_2$ 40 mM | Tris 10 mM | 8.0 | 6.7 | 8.1 | Large particles |
| N | $CaCl_2$ 80 mM | Tris 10 mM | 8.0 | 10.8 | 8.0 | Opalescent + large particles |
| O | $CaCl_2$ 160 mM | Tris 10 mM | 8.0 | 19.7 | 8.0 | Opalescent + large particles |
| P | $MgSO_4$ 87.5 mM | Tris 10 mM | 8.0 | 7.5 | 8.0 | Large particles |
| Q | $MgSO_4$ 175 mM | Tris 10 mM | 8.0 | 10.9 | 8.2 | Opalescent + very large particles |
| R | $MgSO_4$ 430 mM | Tris 10 mM | 8.0 | 21.7 | 8.1 | Opalescent + very large particles |

The results demonstrate that solutions containing Rv1196 related antigens can be sensitive to salts other than sodium chloride. The impact of $CaCl_2$ or $MgSO_4$ appears to be more pronounced than for sodium chloride at comparable concentrations or conductivity.

Example 15

Investigation of "Salting Out" in Compositions Comprising Mtb72f with Different Salt Concentrations at pH 6.1, 7.5 and 8.5

The impact of sodium chloride concentration and pH on Mtb72f antigen stability, as assessed by size, was investigated.

Method

Purified bulk antigen (Mtb72f with 6 his residues, SEQ ID No: 11) was diluted to a concentration of 100 ug/ml in three different buffers (10 mM phosphate buffer at pH 6.1, 20 mM Tris buffer at pH 7.5 and 20 mM Tris buffer at pH 8.5) containing final sodium chloride concentrations of 0, 150 and 450 mM.

Samples were stored for 24 hours at 4° C. or 25° C. before analysis.

Nephelometry was performed using a Nepheloskan® Ascent, available from Thermo Fischer Scientific. Analysis was performed in UV transparent Costar® micro-plates available from Corning Inc (USA).

DLS was performed using a Dynapro Plate Reader from Wyatt Instruments. The instrument was operated using a laser wavelength of 830 nm and power of 50 mW. Scattered light was detected at 150° at a temperature of 22° C. The mean hydrodynamic diameter and polydispersity index (p1) are calculated by the instrument software.

Results

The findings of this experiment are presented in FIGS. 13 and 14.

Both DLS and nephlometry demonstrate a general trend that Mtb72f is sensitive to salt concentration and pH, in a similar manner to M72 as shown in previous examples. Consequently, the benefits of the present invention apply to Rv1196 related antigens and not just to the Rv1196 sequence itself.

In the case of a number of DLS samples, instrumentation was unable to determine a specific particle size (shown as NV in FIG. 14).

Example 16

Prevention of "Salting Out" in Compositions Comprising M72, Immunostimulants and Using Sorbitol as a Tonicity Agent In order to compare the stability of immunogenic compositions containing 150 mM NaCl with compositions using sorbitol as a tonicity agent, samples were monitored using an alternative ELISA.

Method

Lyophilisation cake was prepared as described in Example 11 (specifically method (a) such that when combined with the appropriate adjuvant formulations from Example 7a pH of 8.5 would be obtained.

The lyophilisation cake describe above were reconstituted with 625 ul of the adjuvant solutions prepared in Example 7.

Upon reconstitution with adjuvant solution, the following immunogenic compositions were obtained:

(i) M72 with Two N-Terminal his Residues—ASA (150 mM NaCl-2) pH 8.5
10 ug antigen (20 ug/ml)
5% w/v sucrose
40 mM Tris
0.02% w/v Tween80
500 ug DOPC
125 ug cholesterol
25 ug 3D-MPL
25 ug QS21
150 mM NaCl
10 mM phosphate
pH 8.5

(ii) M72 with Two N-Terminal his Residues—ASA (Sorbitol-2) pH 8.5
10 ug antigen (20 ug/ml)
5% w/v sucrose
40 mM Tris
0.02% w/v Tween80
500 ug DOPC
125 ug cholesterol
25 ug 3D-MPL
25 ug QS21
5 mM NaCl
4.7% w/v sorbitol
10 mM phosphate
pH 8.5

The reconstituted immunogenic compositions described above were characterised after storage at 30° C. (T24 h) and compared with an extemporaneously prepared sample (T0).

Antigenicity was quantified by an indirect sandwich ELISA in which the antigen is captured by a M72-specific rabbit polyclonal antibody and subsequently revealed by a M72(Mtb39)-specific mouse monoclonal antibody. Briefly, the plate is coated with anti-M72 rabbit polyclonal antibody at the dilution of 1/8000 in Dulbecco's Phosphate Buffered Saline overnight at 4° C. and after four washes the plates were blocked for 1 h at 37° C. with saturation buffer (PBS, 0.1% Tween 20, 1% BSA). After the washing step, protein standard (M72 purified bulk: 1950 ug/ml), internal control (M72: 1768 ug/ml) and samples are loaded in wells from the first column of the plate at a concentration of approximately 0.25 µg/ml and then a 2-fold serial dilution is performed in the saturation buffer (PBS, 0.025% Tween 20) from well 1 to 12 and incubated 1h30 at 37° C. After the washing step, the immune complex is then incubated 1 h at 37° C. with anti-M72 mouse monoclonal antibody at a dilution of 1/1000 in saturation buffer (PBS, 0.025% Tween 20). After four washes, a biotinylated rabbit anti-mouse polyclonal antibody was added at a dilution of 1/1000 in saturation buffer (PBS, 0.025% Tween 20). After four washes, the signal was amplified by adding Streptavidin-Horseradish Peroxidase diluted 1/4000 in saturation buffer (PBS, 0.025% Tween 20). After four washes, the signal was revealed by ortho phenylene diamine dihydrochlorid (OPDA) for 15 min at RT and the reaction is stopped by addition of HCl 1M. The coloration is proportional to the quantity of bound anti-M72 antibody, and is measured at 490 nm and 620 nm. All washing steps were performed using PBS, 0.025% Tween 20.

All measured values are presented relative to the expected antigenicity based on the purified bulk protein used to prepare the tested formulations.

Results

Figure 15:
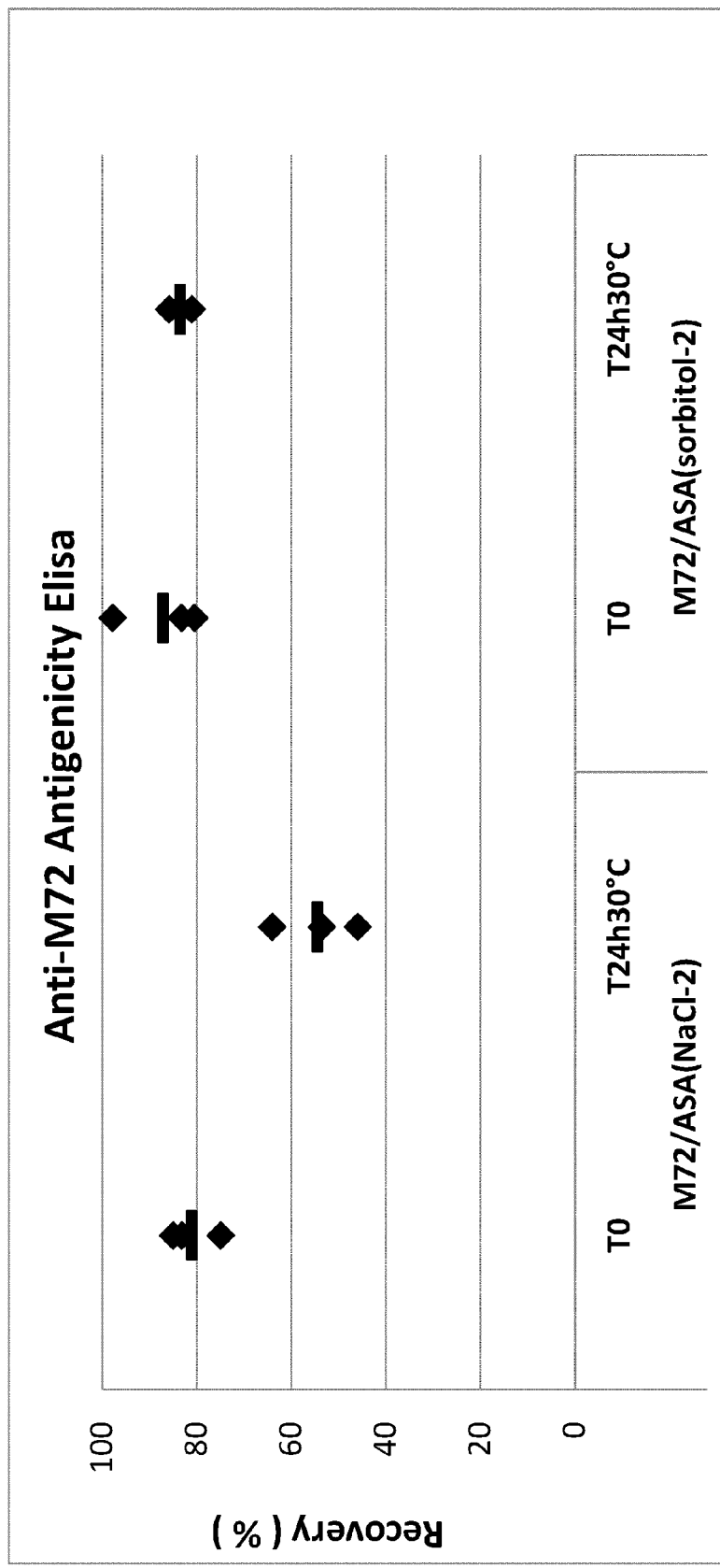

The results are shown in FIG. 15. Diamonds indicating the specific measurements for each of the three test samples, with a line indicating the average value.

Antigen recovery is largely stable after reconstitution in low salt compositions using sorbitol as a tonicity agent at pH 8.5 up to 24 h at 30° C. Recovery in ASA (sorbitol-2) was 83.5% after 24 hours (T0 87.1%, meaning 95.9% of the relative antigenicity was maintained), whereas recovery in ASA (NaCl-2) was 54.5% after 24 hours (T0 81.0%, meaning only 67.3% of the relative antigenicity was maintained after storage).

In summary, Example 8 demonstrates for the first time the detrimental impact resulting from pH and NaCl concentration on the stability of immunogenic compositions containing an Rv1196 related antigen. Example 14 extends this work to show that other salts may also have a detrimental impact on the stability of immunogenic compositions containing an Rv1196 related antigen, with Examples 10, 11, 12, 15 and 16 demonstrating that the effect is also applicable to other sequences.

Reformulation of the immunogenic compositions with a non-ionic tonicity agent addresses the antigen stability problems. Additionally, Examples 3, 4, 13 and 16 demonstrate the removal of substantially all NaCl from the immunogenic formulation and its replacement with sorbitol as a tonicity agent does not have a detrimental impact on the stimulation of T cell responses.

Stability of immunogenic compositions is key and may be particularly challenging when in isolated locations were refrigeration may not be readily accessible. By reducing the presence of salts in the immunogenic compositions, the present inventors have been able to reduce the extent of changes observed when the immunogenic compositions are stored.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All documents referred to herein, including patents and patent applications, are incorporated by reference in their entirety.

The invention claimed is:

1. An immunogenic composition comprising an Rv1196 related antigen, said composition further comprising a polyol,
   wherein the conductivity of said composition is 3 mS/cm or lower,
   wherein the osmolality of said composition is 250 to 750 mOsm/kg,
   wherein the pH of said composition is in the range 7.0 to 9.0, and
   wherein the Rv1196 related antigen comprises a sequence having at least 90% identity to SEQ ID No: 1; and wherein said immunogenic composition is pharmaceutically acceptable.

2. The immunogenic composition according to claim 1, wherein the conductivity of the composition is 2.5 mS/cm or lower.

3. The immunogenic composition according to claim 1, wherein the concentration of salts in said composition is 40 mM or lower.

4. The immunogenic composition according to claim 1, wherein the concentration of sodium chloride in said composition is 40 mM or lower.

5. The immunogenic composition according to claim 1, further comprising a non-ionic tonicity agent.

6. The immunogenic composition according to claim 5, wherein the non-ionic tonicity agent is a polyol.

7. The immunogenic composition according to claim 6, wherein the polyol is sorbitol and wherein the concentration of sorbitol is between about 4 and about 6% (w/v).

8. The immunogenic composition according to claim 6, wherein the polyol is sucrose and wherein the concentration of sucrose is between about 4 and about 6% (w/v).

9. The immunogenic composition according to claim 6, wherein the polyol is sorbitol and the pH of said composition is in the range 7.5 to 8.5.

10. The immunogenic composition according to claim 1 further comprising one or more immunostimulants.

11. The immunogenic composition according to claim 10, wherein said one or more immunostimulants comprise an immunostimulant selected from the group consisting of QS21 and 3-de-O-acylated monophoshoryllipid A.

12. The immunogenic composition according to claim 1 wherein the Rv1196 related antigen comprises a sequence having at least 95% identity to SEQ ID No: 1.

13. The immunogenic composition according to claim 1 wherein the RV1196 related antigen comprises the sequence of SEQ ID No: 1.

14. The immunogenic composition according to claim 10, wherein the immunogenic composition comprises a saponin which is QS21.

15. The immunogenic composition according to claim 10, wherein the immunogenic composition comprises 3-de-O-acylated monophoshoryl lipid A.

16. The immunogenic composition according to claim 1, wherein the composition is provided as a unit dose of between 50 ul and 1 ml and wherein the unit dose contains 1 to 100 ug of Rv1196 related protein.

\* \* \* \* \*

SEQUENCE LISTING

<160> NUMBER OF SEQ ID NOS: 17

<210> SEQ ID NO 1
<211> LENGTH: 391
<212> TYPE: PRT
<213> ORGANISM: Mycobacterium tuberculosis H37Rv

<400> SEQUENCE: 1

Met Val Asp Phe Gly Ala Leu Pro Pro Glu Ile Asn Ser Ala Arg Met

```
1               5                   10                  15
Tyr Ala Gly Pro Gly Ser Ala Ser Leu Val Ala Ala Gln Met Trp
            20                  25                  30
Asp Ser Val Ala Ser Asp Leu Phe Ser Ala Ala Ser Ala Phe Gln Ser
            35                  40                  45
Val Val Trp Gly Leu Thr Val Gly Ser Trp Ile Gly Ser Ser Ala Gly
50                  55                  60
Leu Met Val Ala Ala Ala Ser Pro Tyr Val Ala Trp Met Ser Val Thr
65                  70                  75                  80
Ala Gly Gln Ala Glu Leu Thr Ala Ala Gln Val Arg Val Ala Ala Ala
            85                  90                  95
Ala Tyr Glu Thr Ala Tyr Gly Leu Thr Val Pro Pro Val Ile Ala
            100                 105                 110
Glu Asn Arg Ala Glu Leu Met Ile Leu Ile Ala Thr Asn Leu Leu Gly
            115                 120                 125
Gln Asn Thr Pro Ala Ile Ala Val Asn Glu Ala Glu Tyr Gly Glu Met
            130                 135                 140
Trp Ala Gln Asp Ala Ala Ala Met Phe Gly Tyr Ala Ala Ala Thr Ala
145                 150                 155                 160
Thr Ala Thr Ala Thr Leu Leu Pro Phe Glu Glu Ala Pro Glu Met Thr
                    165                 170                 175
Ser Ala Gly Gly Leu Leu Glu Gln Ala Ala Val Glu Glu Ala Ser
            180                 185                 190
Asp Thr Ala Ala Ala Asn Gln Leu Met Asn Asn Val Pro Gln Ala Leu
            195                 200                 205
Gln Gln Leu Ala Gln Pro Thr Gln Gly Thr Thr Pro Ser Ser Lys Leu
            210                 215                 220
Gly Gly Leu Trp Lys Thr Val Ser Pro His Arg Ser Pro Ile Ser Asn
225                 230                 235                 240
Met Val Ser Met Ala Asn Asn His Met Ser Met Thr Asn Ser Gly Val
                    245                 250                 255
Ser Met Thr Asn Thr Leu Ser Ser Met Leu Lys Gly Phe Ala Pro Ala
            260                 265                 270
Ala Ala Ala Gln Ala Val Gln Thr Ala Ala Gln Asn Gly Val Arg Ala
            275                 280                 285
Met Ser Ser Leu Gly Ser Ser Leu Gly Ser Ser Gly Leu Gly Gly Gly
            290                 295                 300
Val Ala Ala Asn Leu Gly Arg Ala Ala Ser Val Gly Ser Leu Ser Val
305                 310                 315                 320
Pro Gln Ala Trp Ala Ala Ala Asn Gln Ala Val Thr Pro Ala Ala Arg
                    325                 330                 335
Ala Leu Pro Leu Thr Ser Leu Thr Ser Ala Ala Glu Arg Gly Pro Gly
            340                 345                 350
Gln Met Leu Gly Gly Leu Pro Val Gly Gln Met Gly Ala Arg Ala Gly
            355                 360                 365
Gly Gly Leu Ser Gly Val Leu Arg Val Pro Pro Arg Pro Tyr Val Met
            370                 375                 380
Pro His Ser Pro Ala Ala Gly
385                 390

<210> SEQ ID NO 2
<211> LENGTH: 1173
<212> TYPE: DNA
<213> ORGANISM: Mycobacterium tuberculosis H37Rv
```

<400> SEQUENCE: 2

```
atggtggatt tcgggcgtt accaccggag atcaactccg cgaggatgta cgccggcccg     60
ggttcggcct cgctggtggc cgcggctcag atgtgggaca gcgtggcgag tgacctgttt    120
tcggccgcgt cggcgtttca gtcggtggtc tggggtctga cggtggggtc gtggataggt    180
tcgtcggcgg gtctgatggt ggcggcggcc tcgccgtatg tggcgtggat gagcgtcacc    240
gcggggcagg ccgagctgac cgccgcccag gtccgggttg ctgcggcggc ctacgagacg    300
gcgtatgggc tgacggtgcc cccgccggtg atcgccgaga accgtgctga actgatgatt    360
ctgatagcga ccaacctctt ggggcaaaac accccggcga tcgcggtcaa cgaggccgaa    420
tacggcgaga tgtgggccca agacgccgcc gcgatgtttg gctacgccgc ggcgacggcg    480
acggcgacgg cgacgttgct gccgttcgag gaggcgccgg agatgaccag cgcgggtggg    540
ctcctcgagc aggccgccgc ggtcgaggag gcctccgaca ccgccgcggc gaaccagttg    600
atgaacaatg tgccccaggc gctgcaacag ctggcccagc ccacgcaggg caccacgcct    660
tcttccaagc tgggtggcct gtggaagacg gtctcgccgc atcggtcgcc gatcagcaac    720
atggtgtcga tggccaacaa ccacatgtcg atgaccaact cggtgtgtc gatgaccaac    780
accttgagct cgatgttgaa gggctttgct ccggcggcgg ccgcccaggc cgtgcaaacc    840
gcggcgcaaa acggggtccg ggcgatgagc tcgctgggca gctcgctggg ttcttcgggt    900
ctgggcggtg gggtggccgc caacttgggt cgggcggcct cggtcggttc gttgtcggtg    960
ccgcaggcct gggccgcggc caaccaggca gtcaccccgg cggcgcgggc gctgccgctg   1020
accagcctga ccagcgccgc ggaaagaggg cccgggcaga tgctgggcgg gctgccggtg   1080
gggcagatgg cgccagggc cggtggtggg ctcagtggtg tgctgcgtgt ccgccgcga   1140
ccctatgtga tgccgcattc tccggcggcc ggc                                1173
```

<210> SEQ ID NO 3
<211> LENGTH: 391
<212> TYPE: PRT
<213> ORGANISM: Mycobacterium tuberculosis F11

<400> SEQUENCE: 3

```
Met Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Lys Met Trp
            20                  25                  30

Asp Ser Val Ala Ser Asp Leu Phe Ser Ala Ala Ser Ala Phe Gln Ser
        35                  40                  45

Val Val Trp Gly Leu Thr Val Gly Ser Trp Ile Gly Ser Ser Ala Gly
    50                  55                  60

Leu Met Val Ala Ala Ser Pro Tyr Val Ala Trp Met Ser Val Thr
65                  70                  75                  80

Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Val Ile Ala
            100                 105                 110

Glu Asn Arg Ala Glu Leu Met Ile Leu Ile Ala Thr Asn Leu Leu Gly
        115                 120                 125

Gln Asn Thr Pro Ala Ile Ala Val Asn Glu Ala Glu Tyr Gly Glu Met
    130                 135                 140

Trp Ala Gln Asp Ala Ala Ala Met Phe Gly Tyr Ala Ala Ala Thr Ala
```

```
            145                 150                 155                 160
Thr Ala Thr Ala Thr Leu Leu Pro Phe Glu Glu Ala Pro Glu Met Thr
                    165                 170                 175

Ser Ala Gly Gly Leu Leu Glu Gln Ala Ala Val Glu Glu Ala Ser
                180                 185                 190

Asp Thr Ala Ala Ala Asn Gln Leu Met Asn Asn Val Pro Gln Ala Leu
            195                 200                 205

Gln Gln Leu Ala Gln Pro Thr Gln Gly Thr Thr Pro Ser Ser Lys Leu
    210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
            260                 265                 270

Ala Ala Ala Gln Ala Val Gln Thr Ala Ala Gln Asn Gly Val Arg Ala
        275                 280                 285

Met Ser Ser Leu Gly Ser Ser Leu Gly Ser Ser Gly Leu Gly Gly Gly
    290                 295                 300

Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly
            340                 345                 350

Gln Met Leu Gly Gly Leu Pro Val Gly Gln Met Gly Ala Arg Ala Gly
        355                 360                 365

Gly Gly Leu Ser Gly Val Leu Arg Val Pro Pro Arg Pro Tyr Val Met
    370                 375                 380

Pro His Ser Pro Ala Ala Gly
385                 390

<210> SEQ ID NO 4
<211> LENGTH: 1173
<212> TYPE: DNA
<213> ORGANISM: Mycobacterium tuberculosis F11

<400> SEQUENCE: 4
atggtggatt cggggcgtt accaccggag atcaactccg cgaggatgta tgccggcccg    60
ggttcggcct cgctggtggc cgccgcgaag atgtgggaca cgtggcgag tgacctgttt   120
tcggccgcgt cggcgtttca gtcggtggtc tggggtctga cggtgggtc gtggataggt   180
tcgtcggcgg gtctgatggt ggcggcgcc tcgccgtatg tggcgtggat gagcgtcacc   240
gcggggcagg ccgagctgac cgccgcccag gtccgggttg ctgcggcggc ctacgagacg   300
gcgtatgggc tgacggtgcc cccgccggtg atcgccgaga ccgtgctga actgatgatt   360
ctgatagcga ccaacctctt ggggcaaaac accccggcga tcgcggtcaa cgaggccgaa   420
tacggcgaga tgtgggccca agacgccgcc gcgatgtttg gctacgccgc ggcgacggcg   480
acggcgacgg cgacgttgct gccgttcgag gaggcgccgg agatgaccag gcgggtgggg   540
ctcctcgagc aggccgccgc ggtcgaggag gcctccgaca ccgccgcggc gaaccagttg   600
atgaacaatg tgccccaggc gctgcaacag ctggcccagc ccacgcaggg caccacgcct   660
tcttccaagc tgggtggcct gtggaagacg gtctcgccgc atcggtcgcc gatcagcaac   720
```

-continued

```
atggtgtcga tggccaacaa ccacatgtcg atgaccaact cgggtgtgtc gatgaccaac      780
accttgagct cgatgttgaa gggctttgct ccggcggcgg ccgcccaggc cgtgcaaacc      840
gcggcgcaaa acggggtccg ggcgatgagc tcgctgggca gctcgctggg ttcttcgggt      900
ctgggcggtg ggtggccgc caacttgggt cgggcggcct cggtcggttc gttgtcggtg      960
ccgcaggcct gggccgcggc caaccaggca gtcaccccgg cggcgcgggc gctgccgctg     1020
accagcctga ccagcgccgc ggaaagaggg cccgggcaga tgctgggcgg gctgccggtg     1080
gggcagatgg gcgccagggc cggtggtggg ctcagtggtg tgctgcgtgt tccgccgcga     1140
ccctatgtga tgccgcattc tccggcggcc ggc                                  1173
```

<210> SEQ ID NO 5
<211> LENGTH: 723
<212> TYPE: PRT
<213> ORGANISM: Artificial Sequence
<220> FEATURE:
<223> OTHER INFORMATION: M72 fusion protein

<400> SEQUENCE: 5

```
Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Arg
            20                  25                  30

Ser Gly Gly Gly Ser Pro Thr Val His Ile Gly Pro Thr Ala Phe Leu
        35                  40                  45

Gly Leu Gly Val Val Asp Asn Asn Gly Asn Gly Ala Arg Val Gln Arg
    50                  55                  60

Val Val Gly Ser Ala Pro Ala Ala Ser Leu Gly Ile Ser Thr Gly Asp
65                  70                  75                  80

Val Ile Thr Ala Val Asp Gly Ala Pro Ile Asn Ser Ala Thr Ala Met
                85                  90                  95

Ala Asp Ala Leu Asn Gly His His Pro Gly Asp Val Ile Ser Val Thr
            100                 105                 110

Trp Gln Thr Lys Ser Gly Gly Thr Arg Thr Gly Asn Val Thr Leu Ala
        115                 120                 125

Glu Gly Pro Pro Ala Glu Phe Met Val Asp Phe Gly Ala Leu Pro Pro
    130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
            180                 185                 190

Trp Ile Gly Ser Ser Ala Gly Leu Met Val Ala Ala Ser Pro Tyr
        195                 200                 205

Val Ala Trp Met Ser Val Thr Ala Gly Gln Ala Glu Leu Thr Ala Ala
    210                 215                 220

Gln Val Arg Val Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
                245                 250                 255

Ile Ala Thr Asn Leu Leu Gly Gln Asn Thr Pro Ala Ile Ala Val Asn
            260                 265                 270

Glu Ala Glu Tyr Gly Glu Met Trp Ala Gln Asp Ala Ala Ala Met Phe
        275                 280                 285
```

```
Gly Tyr Ala Ala Ala Thr Ala Thr Ala Thr Leu Leu Pro Phe
    290                 295                 300

Glu Glu Ala Pro Glu Met Thr Ser Ala Gly Gly Leu Leu Glu Gln Ala
305                 310                 315                 320

Ala Ala Val Glu Glu Ala Ser Asp Thr Ala Ala Asn Gln Leu Met
            325                 330                 335

Asn Asn Val Pro Gln Ala Leu Gln Gln Leu Ala Gln Pro Thr Gln Gly
            340                 345                 350

Thr Thr Pro Ser Ser Lys Leu Gly Gly Leu Trp Lys Thr Val Ser Pro
        355                 360                 365

His Arg Ser Pro Ile Ser Asn Met Val Ser Met Ala Asn Asn His Met
    370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Gln Ala Val Gln Thr Ala
                405                 410                 415

Ala Gln Asn Gly Val Arg Ala Met Ser Ser Leu Gly Ser Ser Leu Gly
            420                 425                 430

Ser Ser Gly Leu Gly Gly Val Ala Ala Asn Leu Gly Arg Ala Ala
        435                 440                 445

Ser Val Gly Ser Leu Ser Val Pro Gln Ala Trp Ala Ala Ala Asn Gln
    450                 455                 460

Ala Val Thr Pro Ala Ala Arg Ala Leu Pro Leu Thr Ser Leu Thr Ser
465                 470                 475                 480

Ala Ala Glu Arg Gly Pro Gly Gln Met Leu Gly Gly Leu Pro Val Gly
                485                 490                 495

Gln Met Gly Ala Arg Ala Gly Gly Leu Ser Gly Val Leu Arg Val
            500                 505                 510

Pro Pro Arg Pro Tyr Val Met Pro His Ser Pro Ala Ala Gly Asp Ile
        515                 520                 525

Ala Pro Pro Ala Leu Ser Gln Asp Arg Phe Ala Asp Phe Pro Ala Leu
    530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
                565                 570                 575

Gly Ile Val Ile Asp Pro Asn Gly Val Val Leu Thr Asn Asn His Val
            580                 585                 590

Ile Ala Gly Ala Thr Asp Ile Asn Ala Phe Ser Val Gly Ser Gly Gln
        595                 600                 605

Thr Tyr Gly Val Asp Val Val Gly Tyr Asp Arg Thr Gln Asp Val Ala
    610                 615                 620

Val Leu Gln Leu Arg Gly Ala Gly Gly Leu Pro Ser Ala Ala Ile Gly
625                 630                 635                 640

Gly Gly Val Ala Val Gly Glu Pro Val Val Ala Met Gly Asn Ser Gly
                645                 650                 655

Gly Gln Gly Gly Thr Pro Arg Ala Val Pro Gly Arg Val Val Ala Leu
            660                 665                 670

Gly Gln Thr Val Gln Ala Ser Asp Ser Leu Thr Gly Ala Glu Glu Thr
        675                 680                 685

Leu Asn Gly Leu Ile Gln Phe Asp Ala Ala Ile Gln Pro Gly Asp Ala
    690                 695                 700
```

Gly Gly Pro Val Val Asn Gly Leu Gly Gln Val Gly Met Asn Thr
705                 710                 715                 720

Ala Ala Ser

<210> SEQ ID NO 6
<211> LENGTH: 2172
<212> TYPE: DNA
<213> ORGANISM: Artificial Sequence
<220> FEATURE:
<223> OTHER INFORMATION: Coding sequence for M72 fusion

<400> SEQUENCE: 6

```
atgacggccg cgtccgataa cttccagctg tcccagggtg ggcagggatt cgccattccg      60
atcgggcagg cgatggcgat cgcgggccag atccgatcgg gtgggggggtc acccaccgtt    120
catatcgggc ctaccgcctt cctcggcttg ggtgttgtcg acaacaacgg caacggcgca    180
cgagtccaac gcgtggtcgg gagcgctccg gcggcaagtc tcggcatctc caccggcgac    240
gtgatcaccg cggtcgacgg cgctccgatc aactcggcca ccgcgatggc ggacgcgctt    300
aacgggcatc atcccggtga cgtcatctcg gtgacctggc aaaccaagtc gggcggcacg    360
cgtacaggga acgtgacatt ggccgaggga ccccccgccg aattcatggt ggatttcggg    420
gcgttaccac cggagatcaa ctccgcgagg atgtacgccg cccgggttc ggcctcgctg    480
gtggccgcgg ctcagatgtg ggacagcgtg gcgagtgacc tgttttcggc cgcgtcggcg    540
tttcagtcgg tggtctgggg tctgacggtg gggtcgtgga taggttcgtc ggcgggtctg    600
atggtggcgg cggcctcgcc gtatgtggcg tggatgagcg tcaccgcggg gcaggccgag    660
ctgaccgccg cccaggtccg ggttgctgcg gcggcctacg agacggcgta tgggctgacg    720
gtgcccccgc cggtgatcgc cgagaaccgt gctgaactga tgattctgat agcgaccaac    780
ctcttggggc aaaacacccc ggcgatcgcg gtcaacgagg ccgaatacgg cgagatgtgg    840
gcccaagacg ccgccgcgat gtttggctac gccgcggcga cggcgacggc gacggcgacg    900
ttgctgccgt cgaggaggc gccggagatg accagcgcgg tgggctcct cgagcaggcc    960
gccgcggtcg aggaggcctc cgacaccgcc gcggcgaacc agttgatgaa caatgtgccc   1020
caggcgctgc aacagctggc ccagcccacg cagggcacca cgcccttcttc caagctgggt   1080
ggcctgtgga gacggtctc gccgcatcgg tcgccgatca gcaacatggt gtcgatggcc   1140
aacaaccaca tgtcgatgac caactcgggt gtgtcgatga ccaacaccct tgagctcgatg   1200
ttgaagggct tgctccggc ggcggccgcc caggccgtgc aaaccgcggc gcaaacggg   1260
gtccggggcga tgagctcgct gggcagctcg ctgggttctt cgggtctggg cggtggggtg   1320
gccgccaact tgggtcgggc ggcctcggtc ggttcgttgt cggtgccgca ggcctgggcc   1380
gcggccaacc aggcagtcac cccggcgcg cgggcgctgc cgctgaccag cctgaccagc   1440
gccgcggaaa gagggcccgg gcagatgctg ggcgggctgc cggtggggca gatgggcgcc   1500
agggccggtg gtgggctcag tgtgtgctg cgtgttccgc cgcgacccta tgtgatgccg   1560
cattctccgg cagccggcga tatcgccccg ccggccttgt cgcaggaccg gttcgccgac   1620
ttccccgcgc tgccctcga cccgtccgcg atggtcgccc aagtggggcc acaggtggtc   1680
aacatcaaca ccaaactggg ctacaacaac gccgtgggcg ccgggaccgg catcgtcatc   1740
gatcccaacg tgtcgtgct gaccaacaac cacgtgatcg cggcgccac cgacatcaat   1800
gcgttcagcg tcggctccgg ccaaacctac ggcgtcgatg tggtcgggta tgaccgcacc   1860
caggatgtcg cggtgctgca gctgcgcggt gccggtggcc tgccgtcggc ggcgatcggt   1920
```

```
ggcggcgtcg cggttggtga gcccgtcgtc gcgatgggca acagcggtgg gcagggcgga    1980
acgccccgtg cggtgcctgg cagggtggtc gcgctcggcc aaaccgtgca ggcgtcggat    2040
tcgctgaccg gtgccgaaga gacattgaac gggttgatcc agttcgatgc cgcgatccag    2100
cccggtgatg cgggcgggcc cgtcgtcaac ggcctaggac aggtggtcgg tatgaacacg    2160
gccgcgtcct ag                                                        2172
```

<210> SEQ ID NO 7
<211> LENGTH: 725
<212> TYPE: PRT
<213> ORGANISM: Artificial Sequence
<220> FEATURE:
<223> OTHER INFORMATION: M72 fusion with 2 additional his residues

<400> SEQUENCE: 7

```
Met His His Thr Ala Ala Ser Asp Asn Phe Gln Leu Ser Gln Gly Gly
1               5                   10                  15

Gln Gly Phe Ala Ile Pro Ile Gly Gln Ala Met Ala Ile Ala Gly Gln
            20                  25                  30

Ile Arg Ser Gly Gly Gly Ser Pro Thr Val His Ile Gly Pro Thr Ala
        35                  40                  45

Phe Leu Gly Leu Gly Val Val Asp Asn Asn Gly Asn Gly Ala Arg Val
    50                  55                  60

Gln Arg Val Val Gly Ser Ala Pro Ala Ala Ser Leu Gly Ile Ser Thr
65                  70                  75                  80

Gly Asp Val Ile Thr Ala Val Asp Gly Ala Pro Ile Asn Ser Ala Thr
                85                  90                  95

Ala Met Ala Asp Ala Leu Asn Gly His His Pro Gly Asp Val Ile Ser
            100                 105                 110

Val Thr Trp Gln Thr Lys Ser Gly Gly Thr Arg Thr Gly Asn Val Thr
        115                 120                 125

Leu Ala Glu Gly Pro Pro Ala Glu Phe Met Val Asp Phe Gly Ala Leu
    130                 135                 140

Pro Pro Glu Ile Asn Ser Ala Arg Met Tyr Ala Gly Pro Gly Ser Ala
145                 150                 155                 160

Ser Leu Val Ala Ala Ala Gln Met Trp Asp Ser Val Ala Ser Asp Leu
                165                 170                 175

Phe Ser Ala Ala Ser Ala Phe Gln Ser Val Val Trp Gly Leu Thr Val
            180                 185                 190

Gly Ser Trp Ile Gly Ser Ser Ala Gly Leu Met Val Ala Ala Ala Ser
        195                 200                 205

Pro Tyr Val Ala Trp Met Ser Val Thr Ala Gly Gln Ala Glu Leu Thr
    210                 215                 220

Ala Ala Gln Val Arg Val Ala Ala Ala Tyr Glu Thr Ala Tyr Gly Leu
225                 230                 235                 240

Leu Thr Val Pro Pro Pro Val Ile Ala Glu Asn Arg Ala Glu Leu Met
                245                 250                 255

Ile Leu Ile Ala Thr Asn Leu Leu Gly Gln Asn Thr Pro Ala Ile Ala
            260                 265                 270

Val Asn Glu Ala Glu Tyr Gly Glu Met Trp Ala Gln Asp Ala Ala Ala
        275                 280                 285

Met Phe Gly Tyr Ala Ala Ala Thr Ala Thr Ala Thr Ala Thr Leu Leu
    290                 295                 300

Pro Phe Glu Glu Ala Pro Glu Met Thr Ser Ala Gly Gly Leu Leu Glu
305                 310                 315                 320
```

```
Gln Ala Ala Ala Val Glu Ala Ser Asp Thr Ala Ala Asn Gln
            325                 330                 335

Leu Met Asn Asn Val Pro Gln Ala Leu Gln Gln Leu Ala Gln Pro Thr
            340                 345                 350

Gln Gly Thr Thr Pro Ser Ser Lys Leu Gly Gly Leu Trp Lys Thr Val
        355                 360                 365

Ser Pro His Arg Ser Pro Ile Ser Asn Met Val Ser Met Ala Asn Asn
370                 375                 380

His Met Ser Met Thr Asn Ser Gly Val Ser Met Thr Asn Thr Leu Ser
385                 390                 395                 400

Ser Met Leu Lys Gly Phe Ala Pro Ala Ala Ala Gln Ala Val Gln
                405                 410                 415

Thr Ala Ala Gln Asn Gly Val Arg Ala Met Ser Ser Leu Gly Ser Ser
            420                 425                 430

Leu Gly Ser Ser Gly Leu Gly Gly Val Ala Ala Asn Leu Gly Arg
            435                 440                 445

Ala Ala Ser Val Gly Ser Leu Ser Val Pro Gln Ala Trp Ala Ala Ala
        450                 455                 460

Asn Gln Ala Val Thr Pro Ala Ala Arg Ala Leu Pro Leu Thr Ser Leu
465                 470                 475                 480

Thr Ser Ala Ala Glu Arg Gly Pro Gly Gln Met Leu Gly Gly Leu Pro
                485                 490                 495

Val Gly Gln Met Gly Ala Arg Ala Gly Gly Leu Ser Gly Val Leu
                500                 505                 510

Arg Val Pro Pro Arg Pro Tyr Val Met Pro His Ser Pro Ala Ala Gly
            515                 520                 525

Asp Ile Ala Pro Pro Ala Leu Ser Gln Asp Arg Phe Ala Asp Phe Pro
530                 535                 540

Ala Leu Pro Leu Asp Pro Ser Ala Met Val Ala Gln Val Gly Pro Gln
545                 550                 555                 560

Val Val Asn Ile Asn Thr Lys Leu Gly Tyr Asn Asn Ala Val Gly Ala
            565                 570                 575

Gly Thr Gly Ile Val Ile Asp Pro Asn Gly Val Val Leu Thr Asn Asn
            580                 585                 590

His Val Ile Ala Gly Ala Thr Asp Ile Asn Ala Phe Ser Val Gly Ser
            595                 600                 605

Gly Gln Thr Tyr Gly Val Asp Val Val Gly Tyr Asp Arg Thr Gln Asp
            610                 615                 620

Val Ala Val Leu Gln Leu Arg Gly Ala Gly Gly Leu Pro Ser Ala Ala
625                 630                 635                 640

Ile Gly Gly Gly Val Ala Val Gly Glu Pro Val Val Ala Met Gly Asn
                645                 650                 655

Ser Gly Gly Gln Gly Gly Thr Pro Arg Ala Val Pro Gly Arg Val Val
            660                 665                 670

Ala Leu Gly Gln Thr Val Gln Ala Ser Asp Ser Leu Thr Gly Ala Glu
            675                 680                 685

Glu Thr Leu Asn Gly Leu Ile Gln Phe Asp Ala Ala Ile Gln Pro Gly
            690                 695                 700

Asp Ala Gly Gly Pro Val Val Asn Gly Leu Gly Gln Val Val Gly Met
705                 710                 715                 720

Asn Thr Ala Ala Ser
            725
```

<210> SEQ ID NO 8
<211> LENGTH: 2178
<212> TYPE: DNA
<213> ORGANISM: Artificial Sequence
<220> FEATURE:
<223> OTHER INFORMATION: Coding sequence for M72 fusion with 2 additonal his residues

<400> SEQUENCE: 8

```
atgcatcaca cggccgcgtc cgataacttc cagctgtccc agggtgggca gggattcgcc      60
attccgatcg ggcaggcgat ggcgatcgcg ggccagatcc gatcgggtgg ggggtcaccc     120
accgttcata tcgggcctac cgccttcctc ggcttgggtg ttgtcgacaa caacggcaac     180
ggcgcacgag tccaacgcgt ggtcgggagc gctccggcgg caagtctcgg catctccacc     240
ggcgacgtga tcaccgcggt cgacggcgct ccgatcaact cggccaccgc gatggcggac     300
gcgcttaacg ggcatcatcc cggtgacgtc atctcggtga cctggcaaac caagtcgggc     360
ggcacgcgta cagggaacgt gacattggcc gagggacccc cggccgaatt catggtggat     420
ttcggggcgt taccaccgga gatcaactcc gcgaggatgt acgccggccc gggttcggcc     480
tcgctggtgg ccgcggctca gatgtgggac agcgtggcga gtgacctgtt ttcggccgcg     540
tcggcgtttc agtcggtggt ctggggtctg acggtggggt cgtggatagg ttcgtcggcg     600
ggtctgatgg tggcggcggc ctcgccgtat gtggcgtgga tgagcgtcac cgcggggcag     660
gccgagctga ccgccgccca ggtccgggtt gctgcggcgg cctacgagac ggcgtatggg     720
ctgacggtgc ccccgccggt gatcgccgag aacgtgctg aactgatgat tctgatagcg     780
accaacctct ggggcaaaaa cacccccggcg atcgcggtca acgaggccga atacggcgag     840
atgtgggccc aagacgccgc cgcgatgttt ggctacgccg cggcgacggc gacggcgacg     900
gcgacgttgc tgccgttcga ggaggcgccg gagatgacca cgcgggtgg gctcctcgag     960
caggccgccg cggtcgagga ggcctccgac accgccgcgg cgaaccagtt gatgaacaat    1020
gtgcccagg cgctgcaaca gctggcccag cccacgcagg gcaccacgcc ttcttccaag    1080
ctgggtggcc tgtggaagac ggtctcgccg catcggtcgc cgatcagcaa catggtgtcg    1140
atggccaaca accacatgtc gatgaccaac tcgggtgtgt cgatgaccaa caccttgagc    1200
tcgatgttga agggctttgc tccggcggcg gccgcccagg ccgtgcaaac gcggcgcaa    1260
aacggggtcc gggcgatgag ctcgctgggc agctcgctgg gttcttcggg tctgggcggt    1320
ggggtggccg ccaacttggg tcgggcggcc tcggtcggtt cgttgtcggt gccgcaggcc    1380
tgggccgcgg ccaaccaggc agtcacccg gcggcgcggg cgctgccgct gaccagcctg    1440
accagcgccg cggaaagagg gcccgggcag atgctgggcg gctgccggt ggggcagatg    1500
ggcgccaggg ccgtggtggg gctcagtggt gtgctgcgtg ttccgccgcg acctatgtg    1560
atgccgcatt ctccggcagc cggcgatatc gccccgccgg ccttgtcgca ggaccggttc    1620
gccgacttcc ccgcgctgcc cctcgacccg tccgcgatgg tcgcccaagt ggggccacag    1680
gtggtcaaca tcaacaccaa actgggctac aacaacgccg tgggcgccgg gaccggcatc    1740
gtcatcgatc ccaacggtgt cgtgctgacc aacaaccacg tgatcgcggg cgccaccgac    1800
atcaatgcgt tcagcgtcgg ctccggccaa acctacggcg tcgatgtggt cgggtatgac    1860
cgcacccagg atgtcgcggt gctgcagctg cgcggtgccg gtggcctgcc gtcggcggcg    1920
atcggtggcg gcgtcgcggt tggtgagccc gtcgtcgcga tggcaacag cggtgggcag    1980
ggcggaacgc cccgtgcggt gcctggcagg gtggtcgcgc tcggccaaac cgtgcaggcg    2040
```

-continued

```
tcggattcgc tgaccggtgc cgaagagaca ttgaacgggt tgatccagtt cgatgccgcg    2100
atccagcccg gtgatgcggg cgggcccgtc gtcaacggcc taggacaggt ggtcggtatg    2160
aacacggccg cgtcctag                                                  2178
```

<210> SEQ ID NO 9
<211> LENGTH: 723
<212> TYPE: PRT
<213> ORGANISM: Artificial Sequence
<220> FEATURE:
<223> OTHER INFORMATION: Mtb72f fusion

<400> SEQUENCE: 9

```
Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Arg
            20                  25                  30

Ser Gly Gly Gly Ser Pro Thr Val His Ile Gly Pro Thr Ala Phe Leu
        35                  40                  45

Gly Leu Gly Val Val Asp Asn Asn Gly Asn Gly Ala Arg Val Gln Arg
    50                  55                  60

Val Val Gly Ser Ala Pro Ala Ala Ser Leu Gly Ile Ser Thr Gly Asp
65                  70                  75                  80

Val Ile Thr Ala Val Asp Gly Ala Pro Ile Asn Ser Ala Thr Ala Met
                85                  90                  95

Ala Asp Ala Leu Asn Gly His His Pro Gly Asp Val Ile Ser Val Thr
            100                 105                 110

Trp Gln Thr Lys Ser Gly Gly Thr Arg Thr Gly Asn Val Thr Leu Ala
        115                 120                 125

Glu Gly Pro Pro Ala Glu Phe Met Val Asp Phe Gly Ala Leu Pro Pro
    130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
            180                 185                 190

Trp Ile Gly Ser Ser Ala Gly Leu Met Val Ala Ala Ser Pro Tyr
        195                 200                 205

Val Ala Trp Met Ser Val Thr Ala Gly Gln Ala Glu Leu Thr Ala Ala
    210                 215                 220

Gln Val Arg Val Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
                245                 250                 255

Ile Ala Thr Asn Leu Leu Gly Gln Asn Thr Pro Ala Ile Ala Val Asn
            260                 265                 270

Glu Ala Glu Tyr Gly Glu Met Trp Ala Gln Asp Ala Ala Ala Met Phe
        275                 280                 285

Gly Tyr Ala Ala Ala Thr Ala Thr Ala Thr Leu Leu Pro Phe
    290                 295                 300

Glu Glu Ala Pro Glu Met Thr Ser Ala Gly Gly Leu Leu Glu Gln Ala
305                 310                 315                 320

Ala Ala Val Glu Glu Ala Ser Asp Thr Ala Ala Asn Gln Leu Met
                325                 330                 335
```

```
Asn Asn Val Pro Gln Ala Leu Gln Gln Leu Ala Gln Pro Thr Gln Gly
            340                 345                 350

Thr Thr Pro Ser Ser Lys Leu Gly Gly Leu Trp Lys Thr Val Ser Pro
        355                 360                 365

His Arg Ser Pro Ile Ser Asn Met Val Ser Met Ala Asn Asn His Met
    370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Gln Ala Val Gln Thr Ala
                405                 410                 415

Ala Gln Asn Gly Val Arg Ala Met Ser Ser Leu Gly Ser Ser Leu Gly
            420                 425                 430

Ser Ser Gly Leu Gly Gly Val Ala Ala Asn Leu Gly Arg Ala Ala
            435                 440                 445

Ser Val Gly Ser Leu Ser Val Pro Gln Ala Trp Ala Ala Asn Gln
    450                 455                 460

Ala Val Thr Pro Ala Ala Arg Ala Leu Pro Leu Thr Ser Leu Thr Ser
465                 470                 475                 480

Ala Ala Glu Arg Gly Pro Gly Gln Met Leu Gly Gly Leu Pro Val Gly
                485                 490                 495

Gln Met Gly Ala Arg Ala Gly Gly Leu Ser Gly Val Leu Arg Val
            500                 505                 510

Pro Pro Arg Pro Tyr Val Met Pro His Ser Pro Ala Ala Gly Asp Ile
                515                 520                 525

Ala Pro Pro Ala Leu Ser Gln Asp Arg Phe Ala Asp Phe Pro Ala Leu
                530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
                565                 570                 575

Gly Ile Val Ile Asp Pro Asn Gly Val Val Leu Thr Asn Asn His Val
            580                 585                 590

Ile Ala Gly Ala Thr Asp Ile Asn Ala Phe Ser Val Gly Ser Gly Gln
            595                 600                 605

Thr Tyr Gly Val Asp Val Val Gly Tyr Asp Arg Thr Gln Asp Val Ala
            610                 615                 620

Val Leu Gln Leu Arg Gly Ala Gly Gly Leu Pro Ser Ala Ala Ile Gly
625                 630                 635                 640

Gly Gly Val Ala Val Gly Glu Pro Val Val Ala Met Gly Asn Ser Gly
                645                 650                 655

Gly Gln Gly Gly Thr Pro Arg Ala Val Pro Gly Arg Val Val Ala Leu
            660                 665                 670

Gly Gln Thr Val Gln Ala Ser Asp Ser Leu Thr Gly Ala Glu Glu Thr
            675                 680                 685

Leu Asn Gly Leu Ile Gln Phe Asp Ala Ala Ile Gln Pro Gly Asp Ser
    690                 695                 700

Gly Gly Pro Val Val Asn Gly Leu Gly Gln Val Val Gly Met Asn Thr
705                 710                 715                 720

Ala Ala Ser

<210> SEQ ID NO 10
<211> LENGTH: 2172
<212> TYPE: DNA
<213> ORGANISM: Artificial Sequence
```

<220> FEATURE:
<223> OTHER INFORMATION: Coding sequence for Mtb72f fusion

<400> SEQUENCE: 10

```
atgacggccg cgtccgataa cttccagctg tcccagggtg ggcagggatt cgccattccg     60
atcgggcagg cgatggcgat cgcgggccag atccgatcgg gtgggggtc acccaccgtt    120
catatcgggc ctaccgcctt cctcggcttg ggtgttgtcg acaacaacgg caacggcgca    180
cgagtccaac gcgtggtcgg gagcgctccg gcggcaagtc tcggcatctc caccggcgac    240
gtgatcaccg cggtcgacgg cgctccgatc aactcggcca ccgcgatggc ggacgcgctt    300
aacgggcatc atcccggtga cgtcatctcg gtgacctggc aaaccaagtc gggcggcacg    360
cgtacaggga acgtgacatt ggccgaggga cccccggccg aattcatggt ggatttcggg    420
gcgttaccac cggagatcaa ctccgcgagg atgtacgccg gcccgggttc ggcctcgctg    480
gtggccgcgg ctcagatgtg ggacagcgtg gcgagtgacc tgttttcggc cgcgtcggcg    540
tttcagtcgg tggtctgggg tctgacggtg gggtcgtgga taggttcgtc ggcgggtctg    600
atggtggcgg cggcctcgcc gtatgtggcg tggatgagcg tcaccgcggg gcaggccgag    660
ctgaccgccg cccaggtccg ggttgctgcg gcggcctacg agacggcgta tgggctgacg    720
gtgccccccgc cggtgatcgc cgagaaccgt gctgaactga tgattctgat agcgaccaac    780
ctcttgggc aaaacacccc ggcgatcgcg gtcaacgagg ccgaatacgg cgagatgtgg    840
gcccaagacg ccgccgcgat gtttggctac ccgcgcgcga cggcgacggc gacggcgacg    900
ttgctgccgt cgaggaggc gccggagatg accagcgcgg gtgggctcct cgagcaggcc    960
gccgcggtcg aggaggcctc cgacaccgcc gcggcgaacc agttgatgaa caatgtgccc   1020
caggcgctgc aacagctggc ccagcccacg cagggcacca cgcccttcttc caagctgggt   1080
ggcctgtgga agacggtctc gccgcatcgg tcgccgatca gcaacatggt gtcgatggcc   1140
aacaaccaca tgtcgatgac caactcgggt gtgtcgatga ccaacaccctt gagctcgatg   1200
ttgaagggct ttgctccggc ggcggccgcc caggccgtgc aaaccgcggc gcaaaacggg   1260
gtccggggcga tgagctcgct gggcagctcg ctgggttctt cgggtctggg cggtgggtg   1320
gccgccaact gggtcgggc ggcctcggtc ggttcgttgt cggtgccgca ggcctgggcc   1380
gcggccaacc aggcagtcac cccggcggcg cgggcgctgc cgctgaccag cctgaccagc   1440
gccgcggaaa agggcccgg gcagatgctg gcgggctgc cggtggggca gatgggcgcc   1500
agggccggtg gtgggctcag tggtgtgctg cgtgttccgc cgcgacccta tgtgatgccg   1560
cattctccgg cagccggcga tatcgccccg ccggccttgt cgcaggaccg gttcgccgac   1620
ttccccgcgc tgcccctcga cccgtccgcg atggtcgcc aagtggggcc acaggtggtc   1680
aacatcaaca ccaaactggg ctacaacaac gccgtgggcg ccgggaccgg catcgtcatc   1740
gatcccaacg tgtcgtgct gaccaacaac cacgtgatcg cggcgccac cgacatcaat   1800
gcgttcagcc tcggctccgg ccaaaacctac ggcgtcgatg tggtcgggta tgaccgcacc   1860
caggatgtcg cggtgctgca gctgcgcggt gccggtggcc tgccgtcggc ggcgatcggt   1920
ggcggcgtcg cggttggtga ccccgtcgtc gcgatgggca acagcggtgg gcagggcgga   1980
acgccccgtg cggtgcctgg cagggtggtc gcgctcggca aaaccgtgca ggcgtcggat   2040
tcgctgaccg gtgccgaaga gacattgaac gggttgatcc agttcgatgc cgcgatccag   2100
cccggtgatt cgggcgggcc cgtcgtcaac ggcctaggac aggtggtcgg tatgaacacg   2160
gccgcgtcct ag                                                        2172
```

<210> SEQ ID NO 11
<211> LENGTH: 729
<212> TYPE: PRT
<213> ORGANISM: Artificial Sequence
<220> FEATURE:
<223> OTHER INFORMATION: Mtb72f fusion with 6 additional his residues

<400> SEQUENCE: 11

```
Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
                20                  25                  30

Ile Ala Gly Gln Ile Arg Ser Gly Gly Ser Pro Thr Val His Ile
            35                  40                  45

Gly Pro Thr Ala Phe Leu Gly Leu Gly Val Val Asp Asn Asn Gly Asn
        50                  55                  60

Gly Ala Arg Val Gln Arg Val Val Gly Ser Ala Pro Ala Ala Ser Leu
65                  70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Ala Gln Met Trp Asp Ser Val
                165                 170                 175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
    210                 215                 220

Ala Glu Leu Thr Ala Ala Gln Val Arg Val Ala Ala Ala Ala Tyr Glu
225                 230                 235                 240

Thr Ala Tyr Gly Leu Thr Val Pro Pro Pro Val Ile Ala Glu Asn Arg
                245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
        275                 280                 285

Asp Ala Ala Ala Met Phe Gly Tyr Ala Ala Ala Thr Ala Thr Ala Thr
    290                 295                 300

Ala Thr Leu Leu Pro Phe Glu Glu Ala Pro Glu Met Thr Ser Ala Gly
305                 310                 315                 320

Gly Leu Leu Glu Gln Ala Ala Ala Val Glu Glu Ala Ser Asp Thr Ala
                325                 330                 335

Ala Ala Asn Gln Leu Met Asn Asn Val Pro Gln Ala Leu Gln Gln Leu
            340                 345                 350

Ala Gln Pro Thr Gln Gly Thr Thr Pro Ser Ser Lys Leu Gly Gly Leu
        355                 360                 365
```

```
Trp Lys Thr Val Ser Pro His Arg Ser Pro Ile Ser Asn Met Val Ser
    370                 375                 380
Met Ala Asn Asn His Met Ser Met Thr Asn Ser Gly Val Ser Met Thr
385                 390                 395                 400
Asn Thr Leu Ser Ser Met Leu Lys Gly Phe Ala Pro Ala Ala Ala Ala
                405                 410                 415
Gln Ala Val Gln Thr Ala Ala Gln Asn Gly Val Arg Ala Met Ser Ser
            420                 425                 430
Leu Gly Ser Ser Leu Gly Ser Ser Gly Leu Gly Gly Val Ala Ala
        435                 440                 445
Asn Leu Gly Arg Ala Ala Ser Val Gly Ser Leu Ser Val Pro Gln Ala
    450                 455                 460
Trp Ala Ala Ala Asn Gln Ala Val Thr Pro Ala Ala Arg Ala Leu Pro
465                 470                 475                 480
Leu Thr Ser Leu Thr Ser Ala Ala Glu Arg Gly Pro Gly Gln Met Leu
                485                 490                 495
Gly Gly Leu Pro Val Gly Gln Met Gly Ala Arg Ala Gly Gly Gly Leu
            500                 505                 510
Ser Gly Val Leu Arg Val Pro Pro Arg Pro Tyr Val Met Pro His Ser
        515                 520                 525
Pro Ala Ala Gly Asp Ile Ala Pro Pro Ala Leu Ser Gln Asp Arg Phe
    530                 535                 540
Ala Asp Phe Pro Ala Leu Pro Leu Asp Pro Ser Ala Met Val Ala Gln
545                 550                 555                 560
Val Gly Pro Gln Val Val Asn Ile Asn Thr Lys Leu Gly Tyr Asn Asn
                565                 570                 575
Ala Val Gly Ala Gly Thr Gly Ile Val Ile Asp Pro Asn Gly Val Val
            580                 585                 590
Leu Thr Asn Asn His Val Ile Ala Gly Ala Thr Asp Ile Asn Ala Phe
        595                 600                 605
Ser Val Gly Ser Gly Gln Thr Tyr Gly Val Asp Val Val Gly Tyr Asp
    610                 615                 620
Arg Thr Gln Asp Val Ala Val Leu Gln Leu Arg Gly Ala Gly Gly Leu
625                 630                 635                 640
Pro Ser Ala Ala Ile Gly Gly Val Ala Val Gly Glu Pro Val Val
                645                 650                 655
Ala Met Gly Asn Ser Gly Gly Gln Gly Thr Pro Arg Ala Val Pro
            660                 665                 670
Gly Arg Val Val Ala Leu Gly Gln Thr Val Gln Ala Ser Asp Ser Leu
        675                 680                 685
Thr Gly Ala Glu Glu Thr Leu Asn Gly Leu Ile Gln Phe Asp Ala Ala
    690                 695                 700
Ile Gln Pro Gly Asp Ser Gly Gly Pro Val Val Asn Gly Leu Gly Gln
705                 710                 715                 720
Val Val Gly Met Asn Thr Ala Ala Ser
                725

<210> SEQ ID NO 12
<211> LENGTH: 2190
<212> TYPE: DNA
<213> ORGANISM: Artificial Sequence
<220> FEATURE:
<223> OTHER INFORMATION: Coding sequence for M72 fusion with 6 additonal
      his residues

<400> SEQUENCE: 12
```

```
atgcatcacc atcaccatca cacggccgcg tccgataact tccagctgtc ccagggtggg      60
cagggattcg ccattccgat cgggcaggcg atggcgatcg cgggccagat ccgatcgggt     120
gggggtcac ccaccgttca tatcgggcct accgccttcc tcggcttggg tgttgtcgac     180
aacaacggca acggcgcacg agtccaacgc gtggtcggga gcgctccggc ggcaagtctc     240
ggcatctcca ccggcgacgt gatcaccgcg gtcgacggcg ctccgatcaa ctcggccacc     300
gcgatggcg acgcgcttaa cgggcatcat cccggtgacg tcatctcggt gacctggcaa     360
accaagtcgg gcggcacgcg tacagggaac gtgacattgg ccgagggacc cccggccgaa     420
ttcatggtg atttcggggc gttaccaccg gagatcaact ccgcgaggat gtacgccggc     480
ccgggttcgg cctcgctggt ggccgcggct cagatgtggg acagcgtggc gagtgacctg     540
ttttcggccg cgtcggcgtt tcagtcgtg gtctggggtc tgacggtggg gtcgtggata     600
ggttcgtcgg cgggtctgat ggtggcggcg gcctcgccgt atgtggcgtg gatgagcgtc     660
accgcggggc aggccgagct gaccgccgcc caggtccggg ttgctgcggc ggcctacgag     720
acggcgtatg ggctgacggt gcccccgccg gtgatcgccg agaaccgtgc tgaactgatg     780
attctgatag cgaccaacct cttggggcaa acaccccgg cgatcgcggt caacgaggcc      840
gaatacggcg agatgtgggc ccaagacgcc gccgcgatgt ttggctacgc cgcggcgacg     900
gcgacggcga cggcgacgtt gctgccgttc gaggaggcgc cggagatgac cagcgcgggt     960
gggctcctcg agcaggccgc cgcggtcgag gaggcctccg acaccgccgc ggcgaaccag    1020
ttgatgaaca atgtgcccca ggcgctgcaa cagctggccc agcccacgca gggcaccacg    1080
ccttcttcca agctgggtgg cctgtggaag acggtctcgc cgcatcggtc gccgatcagc    1140
aacatggtgt cgatggccaa caaccacatg tcgatgacca actcgggtgt gtcgatgacc    1200
aacaccttga gctcgatgtt gaagggcttt gctccggcgg cggccgccca ggccgtgcaa    1260
accgcggcgc aaaacggggt ccgggcgatg agctcgctgg gcagctcgct gggttcttcg    1320
ggtctgggcg gtggggtggc cgccaacttg ggtcgggcgg cctcggtcgg ttcgttgtcg    1380
gtgccgcagg cctgggccgc ggccaaccag gcagtcaccc cggcggcgcg ggcgctgccg    1440
ctgaccagcc tgaccagcgc cgcggaaaga gggcccgggc agatgctggg cgggctgccg    1500
gtggggcaga tgggcgccag ggccggtggt gggctcagtg gtgtgctgcg tgttccgccg    1560
cgaccctatg tgatgccgca ttctccggca gccggcgata tcgccccgcc ggccttgtcg    1620
caggaccggt tcgccgactt ccccgcgctg cccctcgacc cgtccgcgat ggtcgcccaa    1680
gtggggccac aggtggtcaa catcaacacc aaactgggct acaacaacgc cgtgggcgcc    1740
gggaccggca tcgtcatcga tcccaacggt gtcgtgctga ccaacaacca cgtgatcgcg    1800
ggcgccaccg acatcaatgc gttcagcgtc ggctccggcc aaacctacgg cgtcgatgtg    1860
gtcgggtatg accgcaccca ggatgtcgcg gtgctgcagc tgcgcggtgc cggtggcctg    1920
ccgtcggcgg cgatcggtgg cggcgtcgcg gttggtgagc cgtcgtcgc gatgggcaac    1980
agcggtgggc agggcggaac gccccgtgcg gtgcctggca gggtggtcgc gctcggccaa    2040
accgtgcagg cgtcggattc gctgaccggt gccgaagaga cattgaacgg gttgatccag    2100
ttcgatgccg cgatccagcc cggtgattcg gcgggcccg tcgtcaacgg cctaggacag    2160
gtggtcggta tgaacacggc cgcgtcctag                                     2190
```

<210> SEQ ID NO 13
<211> LENGTH: 20
<212> TYPE: DNA

-continued

```
<213> ORGANISM: Artificial Sequence
<220> FEATURE:
<223> OTHER INFORMATION: Cpg Oligo 1 - CpG 1826

<400> SEQUENCE: 13
tccatgacgt tcctgacgtt                                              20

<210> SEQ ID NO 14
<211> LENGTH: 18
<212> TYPE: DNA
<213> ORGANISM: Artificial Sequence
<220> FEATURE:
<223> OTHER INFORMATION: CpG Oligo 2 - CpG 1758

<400> SEQUENCE: 14
tctcccagcg tgcgccat                                                18

<210> SEQ ID NO 15
<211> LENGTH: 30
<212> TYPE: DNA
<213> ORGANISM: Artificial Sequence
<220> FEATURE:
<223> OTHER INFORMATION: CpG Oligo 3

<400> SEQUENCE: 15
accgatgacg tcgccggtga cggcaccacg                                   30

<210> SEQ ID NO 16
<211> LENGTH: 24
<212> TYPE: DNA
<213> ORGANISM: Artificial Sequence
<220> FEATURE:
<223> OTHER INFORMATION: CpG Oligo 4 - CpG 2006

<400> SEQUENCE: 16
tcgtcgtttt gtcgttttgt cgtt                                         24

<210> SEQ ID NO 17
<211> LENGTH: 20
<212> TYPE: DNA
<213> ORGANISM: Artificial Sequence
<220> FEATURE:
<223> OTHER INFORMATION: CpG Oligo 5 - CpG 1686

<400> SEQUENCE: 17
tccatgacgt tcctgatgct                                              20
```